United States Patent
Sexton et al.

(10) Patent No.: US 10,042,959 B2
(45) Date of Patent: Aug. 7, 2018

(54) SYSTEMS AND METHODS FOR CAPTURE OF RELATIONSHIPS WITHIN INFORMATION

(71) Applicant: Ayasdi, Inc., Menlo Park, CA (US)

(72) Inventors: Harlan Sexton, Palo Alto, CA (US); Jennifer Kloke, Mountain View, CA (US)

(73) Assignee: Ayasdi, Inc., Menlo Park, CA (US)

( * ) Notice: Subject to any disclaimer, the term of this patent is extended or adjusted under 35 U.S.C. 154(b) by 438 days.

(21) Appl. No.: 14/639,954

(22) Filed: Mar. 5, 2015

(65) Prior Publication Data

US 2015/0254370 A1 Sep. 10, 2015

Related U.S. Application Data

(60) Provisional application No. 61/948,490, filed on Mar. 5, 2014.

(51) Int. Cl.
| | |
|---|---|
| G06F 17/00 | (2006.01) |
| G06F 17/30 | (2006.01) |
| G16H 50/70 | (2018.01) |

(52) U.S. Cl.
CPC .. *G06F 17/30958* (2013.01); *G06F 17/30241* (2013.01); *G06F 17/30572* (2013.01); *G16H 50/70* (2018.01)

(58) Field of Classification Search
CPC .............. G06F 17/30; G06F 17/30601; G06F 17/30958; G06F 11/34; G06F 17/2247; G06F 17/227
See application file for complete search history.

(56) References Cited

U.S. PATENT DOCUMENTS

| | | | |
|---|---|---|---|
| 4,878,170 | A | 10/1989 | Zeevi |
| 7,756,342 | B2 | 7/2010 | Bachmann |
| 7,831,381 | B2 | 11/2010 | Thota |
| 2003/0120421 | A1 | 6/2003 | Daubert |
| 2005/0198328 | A1 | 9/2005 | Lee |

(Continued)

OTHER PUBLICATIONS

International Application No. PCDUS2016/031065, International Search Report and Written Opinion dated Aug. 31, 2016.
International Application No. PCT/US2015/019066, International Search Report and Written Opinion dated Jun. 11, 2015.

(Continued)

*Primary Examiner* — Truong Vo
(74) *Attorney, Agent, or Firm* — Sheppard, Mullin, Richter & Hampton LLP

(57) ABSTRACT

Exemplary systems and methods to improve capture of relationships within information are provided. In various embodiments, a system comprises a landmark module configured to choose a set of landmarks from data in a finite metric space, the set of landmarks being a subset of points in the finite metric space, a nearest neighbor module configured to compute, for each landmark, a predetermined number of nearest neighbor landmarks in the set of landmarks, a graph construction module configured to identify at least one pair of landmarks that are nearest neighbors to each other, an edge generator module configured to add an edge between the at least one pair of landmarks, and a non-landmark projection module configured to project non-landmark points based on the landmarks and one or more edges thereby enabling at least one shape to indicate relationships in the data.

21 Claims, 42 Drawing Sheets

(56) References Cited

U.S. PATENT DOCUMENTS

| | | |
|---|---|---|
| 2006/0251324 A1 | 11/2006 | Bachmann |
| 2009/0043504 A1 | 2/2009 | Bandyopadhyay |
| 2010/0254582 A1* | 10/2010 | Liu .................... G06K 9/4638 382/131 |
| 2010/0313157 A1 | 12/2010 | Carlsson et al. |
| 2011/0261049 A1 | 10/2011 | Cardno et al. |
| 2013/0101221 A1 | 4/2013 | Fujiki et al. |
| 2013/0144916 A1 | 6/2013 | Lum et al. |
| 2013/0185624 A1 | 7/2013 | Appleyard et al. |
| 2013/0187922 A1 | 7/2013 | Sexton |
| 2013/0259353 A1 | 10/2013 | Hewett |
| 2013/0297543 A1 | 11/2013 | Treiser |
| 2014/0229768 A1 | 8/2014 | Bernstein et al. |
| 2014/0278479 A1 | 9/2014 | Wang et al. |
| 2014/0330867 A1 | 11/2014 | Sarkar et al. |
| 2014/0337390 A1 | 11/2014 | Kumar |
| 2015/0106578 A1 | 4/2015 | Warfield et al. |
| 2016/0034561 A1 | 2/2016 | Sexton et al. |
| 2016/0246871 A1 | 8/2016 | Singh et al. |

OTHER PUBLICATIONS

Nicolau, Monica et al., "Topology Based Data Analysis Identifies a Subgroup of Breast Cancers with a Unique Mutational Profile and Excellent Survival," Proceedings of the National Academy of Sciences of the United States of America, vol. 108, No. 17, pp. 7265-7270, Apr. 26, 2011.

European Patent Application No. 15757741.2, Search Report dated Jun. 28, 2017.

International Application No. PCT/US2016/066233, International Search Report and Written Opinion dated Apr. 7, 2017.

\* cited by examiner

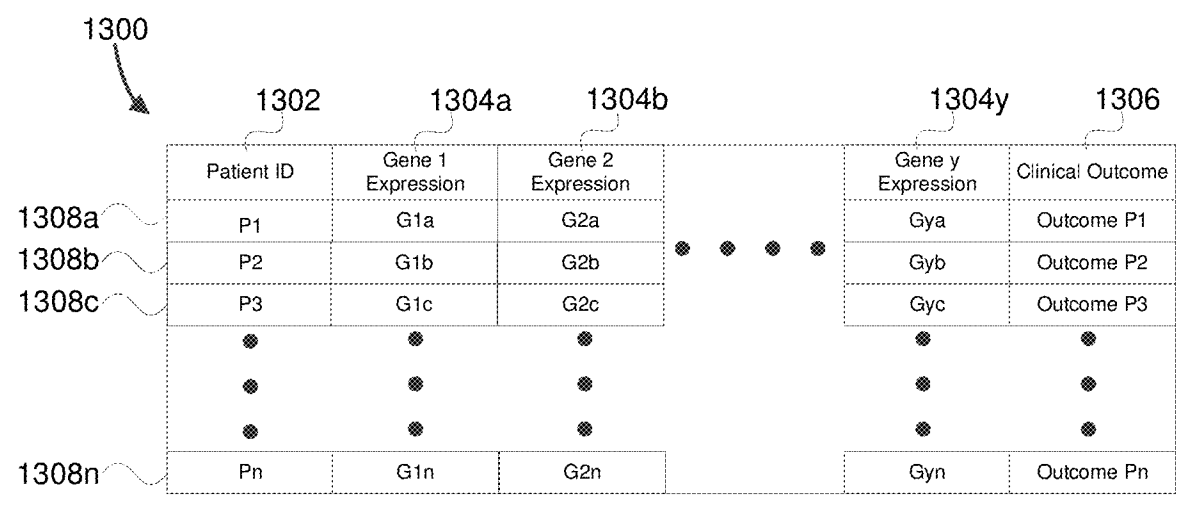

| Patient ID | Gene 1 Expression | Gene 2 Expression | ... | Gene y Expression | Clinical Outcome |
|---|---|---|---|---|---|
| P1 | G1a | G2a | ● | Gya | Outcome P1 |
| P2 | G1b | G2b | ● | Gyb | Outcome P2 |
| P3 | G1c | G2c | ● | Gyc | Outcome P3 |
| ● | ● | ● | ● | ● | ● |
| ● | ● | ● | ● | ● | ● |
| ● | ● | ● | ● | ● | ● |
| Pn | G1n | G2n | | Gyn | Outcome Pn |

FIG. 13

| Landmark | Distance (d) from P1 | Distance (d) from P2 |
|---|---|---|
| R1 | 3 | 5 |
| R2 | 5 | 7 |
| R3 | 7 | 9 |
| R4 | 6 | 8 |

| Data Point | d to nearest Landmark |
|---|---|
| P1 | 3 |
| P2 | 5 |
| P3 | 4 |

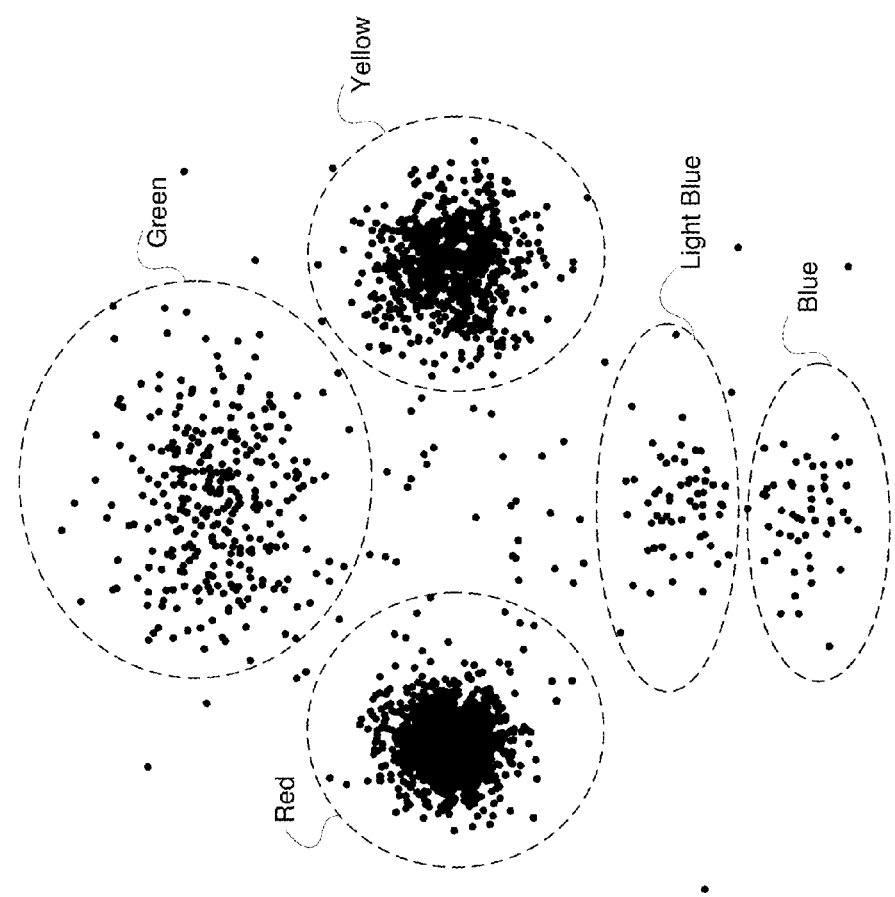

SYSTEMS AND METHODS FOR CAPTURE OF RELATIONSHIPS WITHIN INFORMATION

CROSS REFERENCE TO RELATED APPLICATIONS

This application claims priority to U.S. provisional patent application Ser. No. 61/948,490, entitled "Systems and Methods for Landmarked Stochastic Neighbor Embedding," filed Mar. 5, 2014, which is hereby incorporated by reference herein.

BACKGROUND

1. Field of the Invention

Embodiments of the present invention are directed to projecting received information to a reference space and more particularly to generating a function based on information within a metric space to project the information to a reference space to capture relationships.

2. Related Art

As the collection and storage data has increased, there is an increased need to analyze and make sense of large amounts of data. Examples of large datasets may be found in financial services companies, oil expiration, biotech, and academia. Unfortunately, previous methods of analysis of large multidimensional datasets tend to be insufficient (if possible at all) to identify important relationships and may be computationally inefficient.

In one example, previous methods of analysis often use clustering. Clustering is often too blunt an instrument to identify important relationships in the data. Similarly, previous methods of linear regression, projection pursuit, principal component analysis, and multidimensional scaling often do not reveal important relationships. Existing linear algebraic and analytic methods are too sensitive to large scale distances and, as a result, lose detail.

Further, even if the data is analyzed, sophisticated experts are often necessary to interpret and understand the output of previous methods. Although some previous methods allow graphs depicting some relationships in the data, the graphs are not interactive and require considerable time for a team of such experts to understand the relationships. Further, the output of previous methods does not allow for exploratory data analysis where the analysis can be quickly modified to discover new relationships. Rather, previous methods require the formulation of a hypothesis before testing.

SUMMARY OF THE INVENTION(S)

Exemplary systems and methods to improve capture of relationships within information are provided. In various embodiments, a system comprises a landmark module, a nearest neighbor module, a graph construction module, an edge generator module, and a non-landmark projection module. The landmark module may be configured to choose a set of landmarks from data in a finite metric space. The set of landmarks may be a subset of points in the finite metric space. The nearest neighbor module may be configured to compute, for each landmark, a predetermined number of nearest neighbor landmarks in the set of landmarks. The graph construction module may be configured to identify at least one pair of landmarks that are nearest neighbors to each other. The edge generator module may be configured to add an edge between the at least one pair of landmarks. The non-landmark projection module may be configured to project non-landmark points based on the landmarks and one or more edges thereby enabling at least one shape to indicate relationships in the data.

The system may further comprise an input module configured to receive the data to be analyzed. In some embodiments, the system may further comprise a filter module configured to apply one or more metric functions to the received data to generate the finite metric space. The landmark module may be configured to randomly choose landmarks from the finite metric space.

In various embodiments, the system further comprises a visualization module configured to generate a visualization of the landmarks, one or more edges, and non-landmark points. The landmarks, one or more edges, and non-landmark points may characterize a reference space. The system may further comprise a resolution module configured to cluster the data based on groupings in the reference space, the groupings being generated by a cover function on the reference space.

The system may comprise a visualization module configured to generate a visualization depicting nodes, each node associated with a subset of received data based on a grouping of the data from the cover function on the reference space, and edges for connecting nodes that share at least some of the same received data. The edge generator module may further be configured to identify components in the reference space, each component including a subset of landmarks wherein the subset of landmarks from one component do not share any paths with a subset of landmarks of another component. In some embodiments, the edge generator module may be further configured to compute a component strength between a first and second component of the identified component, the strength being based, at least in part, on scoring a number of nearest neighbors of each landmark in the first component, the nearest neighbors residing in the second component, and generating a component pair score using the scoring of the number of nearest neighbors of each landmark in the first component that reside in the second component.

The edge generator module may further be configured to generate one or more edges between landmarks of components associated with the highest component pair score as compared to other components associated with lower component pair scores. In some embodiments, the edge generator module may further be configured to compute the component strength between the first and second component based, at least in part, on scoring a number of nearest neighbors of each landmark in the second component that reside in the first component, wherein the component pair score is based, at least in part, on the scoring of the number of nearest neighbors of each landmark in the second component that reside in the first component.

An exemplary method comprises selecting a set of landmarks from data in a finite metric space, the set of landmarks being a subset of points in the finite metric space, computing, for each landmark, a predetermined number of nearest neighbor landmarks in the set of landmarks, identifying at least one pair of landmarks that are nearest neighbors to each other, adding an edge between the at least one pair of landmarks, and projecting non-landmark points based on the landmarks and one or more edges thereby enabling at least one shape to indicate relationships in the data.

An exemplary computer readable medium may comprise instructions. The instructions may be executable by a processor to perform a method. The method may comprise selecting a set of landmarks from data in a finite metric space, the set of landmarks being a subset of points in the finite metric space, computing, for each landmark, a predetermined number of nearest neighbor landmarks in the set of landmarks, identifying at least one pair of landmarks that are nearest neighbors to each other, adding an edge between the at least one pair of landmarks, and projecting non-landmark points based on the landmarks and one or more edges thereby enabling at least one shape to indicate relationships in the data.

Exemplary systems and methods for visualization of data analysis are provided. In various embodiments, a method comprises accessing a database, analyzing the database to identify clusters of data, generating an interactive visualization comprising a plurality of nodes and a plurality of edges wherein a first node of the plurality of nodes represents a cluster and an edge of the plurality of edges represents an intersection of nodes of the plurality of nodes, selecting and dragging the first node in response to a user action, and reorienting the interactive visualization in response to the user action of selecting and dragging the first node.

In various embodiments, the method further comprises saving the data in the database associated with the selected first node. The method may comprise selecting a second node and displaying information regarding the first and second node. In some embodiments, the method may comprise receiving a selection of data identifiers of the database and highlighting some of the plurality of nodes associated with the selection.

The first node and a second node of the interactive visualization may be colored differently based on a selected first function. In one example, the first function is a filter. The method may further comprise receiving a second function selection and changing the color of the first and second nodes based on the second function selection.

In various embodiments, the method further comprises receiving an interval value and an overlap percentage, re-analyzing the database based on the interval value and the overlap percentage, and regenerating the interactive visualization based on the re-analysis. Further, the method may comprise displaying movement of the interactive visualization after generation, the movement being based on visual optimization of the plurality of nodes.

In some embodiments, the method may further comprise displaying statistical information about the first node and a selected second node. The analysis of the database may be a topological analysis. In some embodiments, the analysis of the database is a nonlinear data analysis.

An exemplary system comprises a processor, an input module, an analysis module, and a visualization module. The input module may be configured to access a database. The analysis module may be configured to analyze the database to identify clusters of data. The visualization module may be configured to generate an interactive visualization comprising a plurality of nodes and a plurality of edges, wherein a first node of the plurality of nodes represents a cluster and an edge of the plurality of edges represents an intersection between nodes of the plurality of nodes, to select and drag the first node in response to a user action, and to reorient the interactive visualization in response to the user action of selecting and dragging the first node.

An exemplary computer readable medium may comprise instructions. The instructions may be executable by a processor to perform a method. The method may comprise accessing a database, analyzing the database to identify clusters of data, generating an interactive visualization comprising a plurality of nodes and a plurality of edges wherein a first node of the plurality of nodes represents a cluster and an edge of the plurality of edges represents an intersection of nodes of the plurality of nodes, selecting and dragging the first node in response to a user action, and reorienting the interactive visualization in response to a user action of selecting and dragging the first node.

Exemplary systems and methods for predictive visualization of patients are provided. In various embodiments, a system comprises a map and a location engine. The map includes a plurality of groupings and interconnections of the groupings, each grouping having one or more patient members that share biological similarities, each interconnection interconnecting groupings that share at least one common patient member, the map identifying a set of groupings and a set of interconnections having a medical characteristic of a set of medical characteristics. The location engine may be configured to determine whether a new patient shares the biological similarities with the one or more patient members of each grouping thereby enabling association of the new patient with one or more of the set of medical characteristics.

The biological similarities may represent similarities of measurements of gene expressions or similarities of sequencing.

In some embodiments, the map is generated by an analysis server configured to receive biological data associated with the one or more patient members, apply a filtering function to generate a reference space, generate a cover of the reference space based on a resolution, the cover including cover data associated with the filtered biological data, cluster the cover data based on a metric, and display the groupings and the interconnections based on the clusters. The filtering function may be a density estimation function. The metric may be a Pearson correlation.

The location engine configured to determine whether the new patient shares the biological similarities with the one or more patient members of each grouping may comprise the patient location engine configured to determine a distance between biological data of each patient member and new biological data of the new patient, compare distances between the patient members of each grouping and the distances determined for the new patient, and determine a location of the new patient relative to at least one of the member patients.

In some embodiments, the location engine may be further configured to compare distances to one or more of the patient members closest to the new patient's filtered biological data with a diameter of at least one grouping and to indicate that the new patient is associated with the grouping based on the comparison. In various embodiments, the location engine is further configured to determine if the distance to one or more of the patient members closest to the new patient's filtered biological data is greater than a diameter of each grouping and to indicate that the new patient is not associated with each grouping based on the comparison.

The medical characteristic may comprise a clinical outcome.

An exemplary method comprises receiving biological data of a new patient, determining distances between biological data of patient members of map and new biological data from the new patient, the map including a plurality of groupings and interconnections of the groupings, each grouping having one or more of the patient members that share biological similarities, each interconnection interconnecting groupings that share at least one common patient member, the map identifying a set of groupings and a set of interconnections having a medical characteristic of a set of medical characteristics, comparing distances between the one or more patient members and the distances determined for the new patient, and determining a location of the new patient relative to the member patients of the map based on the comparison, thereby enabling association of the new patient with one or more of the set of medical characteristics.

An exemplary computer readable medium may comprise instructions. The instructions may be executable by a processor to perform a method. The method may comprise receiving biological data of a new patient, determining distances between biological data of patient members of map and new biological data from the new patient, the map including a plurality of groupings and interconnections of the groupings, each grouping having one or more of the patient members that share biological similarities, each interconnection interconnecting groupings that share at least one common patient member, the map identifying a set of groupings and a set of interconnections having a medical characteristic of a set of medical characteristics, comparing distances between the one or more patient members and the distances determined for the new patient, and determining a location of the new patient relative to the member patients of the map based on the comparison, thereby enabling association of the new patient with one or more of the set of medical characteristics.

BRIEF DESCRIPTION OF THE DRAWINGS

FIG. 13 is an exemplary data structure including biological data for a number of patients that may be used to generate the cancer map visualization in some embodiments.

FIG. 34 depicts a visualization of a scatter plot of points (i.e., ground truth).

DETAILED DESCRIPTION OF THE DRAWINGS

Some embodiments described herein may be a part of the subject of Topological Data Analysis (TDA). TDA is an area of research which has produced methods for studying point cloud data sets from a geometric point of view. Other data analysis techniques use "approximation by models" of various types. For example, regression methods model the data as the graph of a function in one or more variables. Unfortunately, certain qualitative properties (which one can readily observe when the data is two-dimensional) may be of a great deal of importance for understanding, and these features may not be readily represented within such models.

Figure 1A:
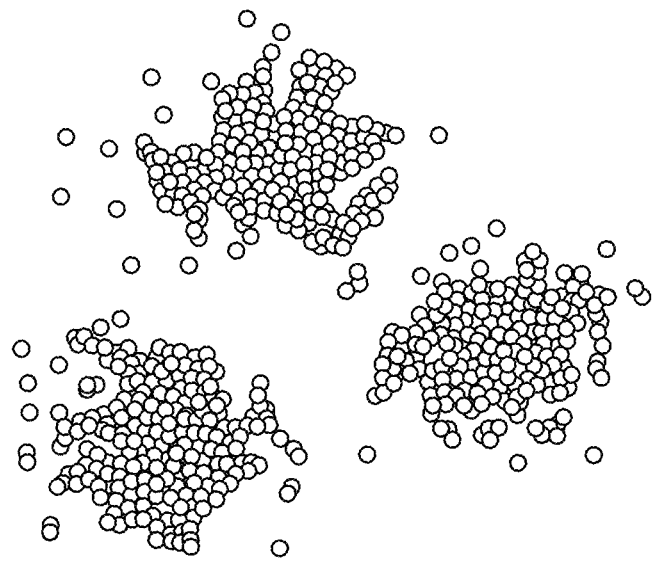
FIG. 1a is an example graph representing data that appears to be divided into three disconnected groups.

FIG. 1a is an example graph representing data that appears to be divided into three disconnected groups. In this example, the data for this graph may be associated with various physical characteristics related to different population groups or biomedical data related to different forms of a disease. Seeing that the data breaks into groups in this fashion can give insight into the data, once one understands what characterizes the groups.

Figure 1B:
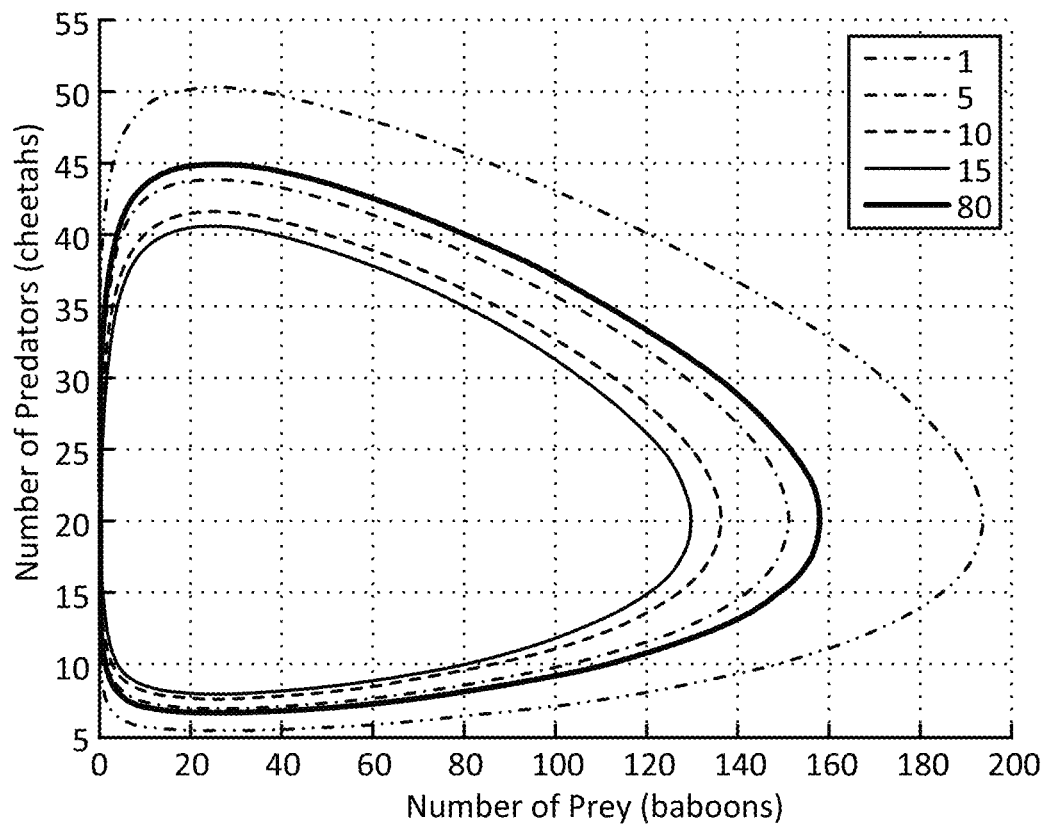
FIG. 1b is an example graph representing data set obtained from a Lotka-Volterra equation modeling the populations of predators and prey over time.

FIG. 1b is an example graph representing data set obtained from a Lotka-Volterra equation modeling the populations of predators and prey over time. From FIG. 1b, one observation about this data is that it is arranged in a loop. The loop is not exactly circular, but it is topologically a circle. The exact form of the equations, while interesting, may not be of as much importance as this qualitative observation which reflects the fact that the underlying phenomenon is recurrent or periodic. When looking for periodic or recurrent phenomena, methods may be developed which can detect the presence of loops without defining explicit models. For example, periodicity may be detectable without having to first develop a fully accurate model of the dynamics.

Figure 1C:
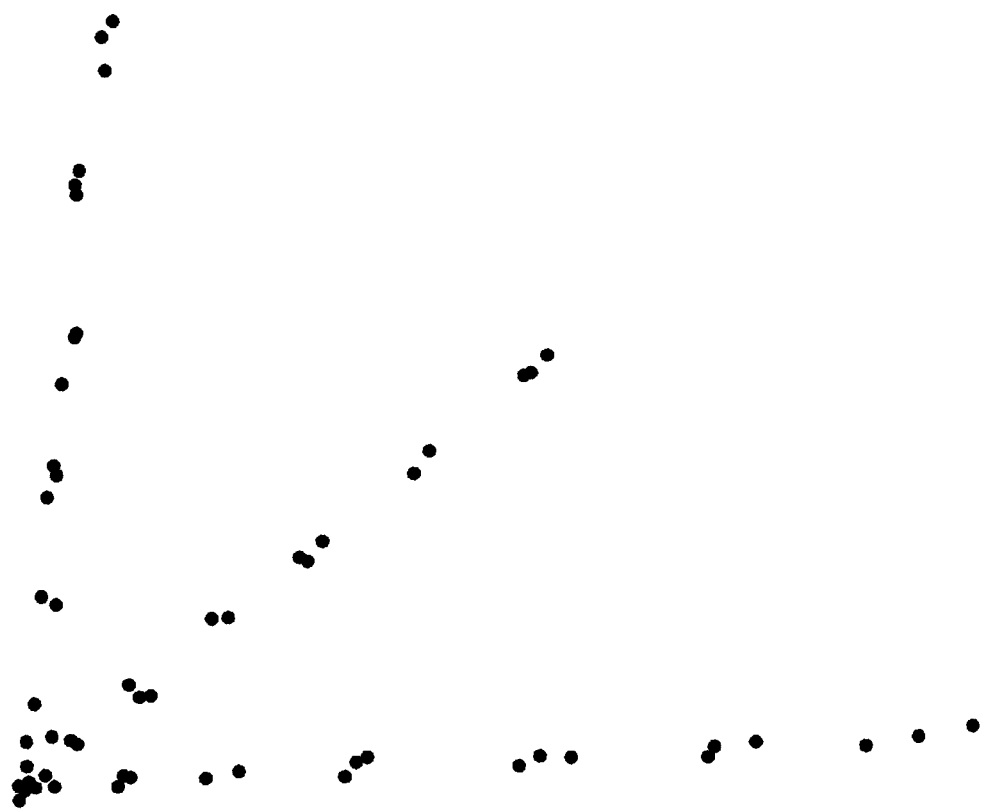
FIG. 1c is an example graph of data sets whereby the data does not break up into disconnected groups, but instead has a structure in which there are lines (or flares) emanating from a central group.

FIG. 1c is an example graph of data sets whereby the data does not break up into disconnected groups, but instead has a structure in which there are lines (or flares) emanating from a central group. In this case, the data also suggests the presence of three distinct groups, but the connectedness of the data does not reflect this. This particular data that is the basis for the example graph in FIG. 1c arises from a study of single nucleotide polymorphisms (SNPs).

In each of the examples above, aspects of the shape of the data are relevant in reflecting information about the data. Connectedness (the simplest property of shape) reflects the presence of a discrete classification of the data into disparate groups. The presence of loops, another simple aspect of shape, often reflect periodic or recurrent behavior. Finally, in the third example, the shape containing flares suggests a classification of the data descriptive of ways in which phenomena can deviate from the norm, which would typically be represented by the central core. These examples support the idea that the shape of data (suitably defined) is an important aspect of its structure, and that it is therefore important to develop methods for analyzing and understanding its shape. The part of mathematics which concerns itself with the study of shape is called topology, and topological data analysis attempts to adapt methods for studying shape which have been developed in pure mathematics to the study of the shape of data, suitably defined.

One question is how notions of geometry or shape are translated into information about point clouds, which are, after all, finite sets? What we mean by shape or geometry can come from a dissimilarity function or metric (e.g., a non-negative, symmetric, real-valued function d on the set of pairs of points in the data set which may also satisfy the triangle inequality, and $d(x; y)=0$ if and only if $x=y$). Such functions exist in profusion for many data sets. For example, when the data comes in the form of a numerical matrix, where the rows correspond to the data points and the columns are the fields describing the data, the n-dimensional Euclidean distance function is natural when there are n fields. Similarly, in this example, there are Pearson correlation distances, cosine distances, and other choices.

When the data is not Euclidean, for example if one is considering genomic sequences, various notions of distance may be defined using measures of similarity based on Basic Local Alignment Search Tool (BLAST) type similarity scores. Further, a measure of similarity can come in non-numeric forms, such as social networks of friends or similarities of hobbies, buying patterns, tweeting, and/or professional interests. In any of these ways the notion of shape may be formulated via the establishment of a useful notion of similarity of data points.

One of the advantages of TDA is that it may depend on nothing more than such a notion, which is a very primitive or low-level model. It may rely on many fewer assumptions than standard linear or algebraic models, for example. Further, the methodology may provide new ways of visualizing and compressing data sets, which facilitate understanding and monitoring data. The methodology may enable study of interrelationships among disparate data sets and/or multiscale/multiresolution study of data sets. Moreover, the methodology may enable interactivity in the analysis of data, using point and click methods.

TDA may be a very useful complement to more traditional methods, such as Principal Component Analysis (PCA), multidimensional scaling, and hierarchical clustering. These existing methods are often quite useful, but suffer from significant limitations. PCA, for example, is an essentially linear procedure and there are therefore limits to its utility in highly non-linear situations. Multidimensional scaling is a method which is not intrinsically linear, but can in many situations wash out detail, since it may overweight large distances. In addition, when metrics do not satisfy an intrinsic flatness condition, it may have difficulty in faithfully representing the data. Hierarchical clustering does exhibit multiscale behavior, but represents data only as disjoint clusters, rather than retaining any of the geometry of the data set. In all four cases, these limitations matter for many varied kinds of data.

We now summarize example properties of an example construction, in some embodiments, which may be used for representing the shape of data sets in a useful, understandable fashion as a finite graph:

The input may be a collection of data points equipped in some way with a distance or dissimilarity function, or other description. This can be given implicitly when the data is in the form of a matrix, or explicitly as a matrix of distances or even the generating edges of a mathematical network.

One construction may also use one or more lens functions (i.e. real valued functions on the data). Lens function(s) may depend directly on the metric. For example, lens function(s) might be the result of a density estimator or a measure of centrality or data depth. Lens function(s) may, in some embodiments, depend on a particular representation of the data, as when one uses the first one or two coordinates of a principal component or multidimensional scaling analysis. In some embodiments, the lens function(s) may be columns which expert knowledge identifies as being intrinsically interesting, as in cholesterol levels and BMI in a study of heart disease.

In some embodiments, the construction may depend on a choice of two or more processing parameters, resolution, and gain. Increase in resolution typically results in more nodes and an increase in the gain increases the number of edges in a visualization and/or graph in a reference space as further described herein.

The output may be, for example, a visualization (e.g., a display of connected nodes or "network") or simplicial complex. One specific combinatorial formulation in one embodiment may be that the vertices form a finite set, and then the additional structure may be a collection of edges (unordered pairs of vertices) which are pictured as connections in this network.

In various embodiments, a system for handling, analyzing, and visualizing data using drag and drop methods as opposed to text based methods is described herein. Philosophically, data analytic tools are not necessarily regarded as "solvers," but rather as tools for interacting with data. For example, data analysis may consist of several iterations of a process in which computational tools point to regions of interest in a data set. The data set may then be examined by people with domain expertise concerning the data, and the data set may then be subjected to further computational analysis. In some embodiments, methods described herein provide for going back and forth between mathematical constructs, including interactive visualizations (e.g., graphs), on the one hand and data on the other.

In one example of data analysis in some embodiments described herein, an exemplary clustering tool is discussed which may be more powerful than existing technology, in that one can find structure within clusters and study how clusters change over a period of time or over a change of scale or resolution.

An exemplary interactive visualization tool (e.g., a visualization module which is further described herein) may produce combinatorial output in the form of a graph which can be readily visualized. In some embodiments, the exemplary interactive visualization tool may be less sensitive to changes in notions of distance than current methods, such as multidimensional scaling.

Some embodiments described herein permit manipulation of the data from a visualization. For example, portions of the data which are deemed to be interesting from the visualization can be selected and converted into database objects, which can then be further analyzed. Some embodiments described herein permit the location of data points of interest within the visualization, so that the connection between a given visualization and the information the visualization represents may be readily understood.

Figure 2:
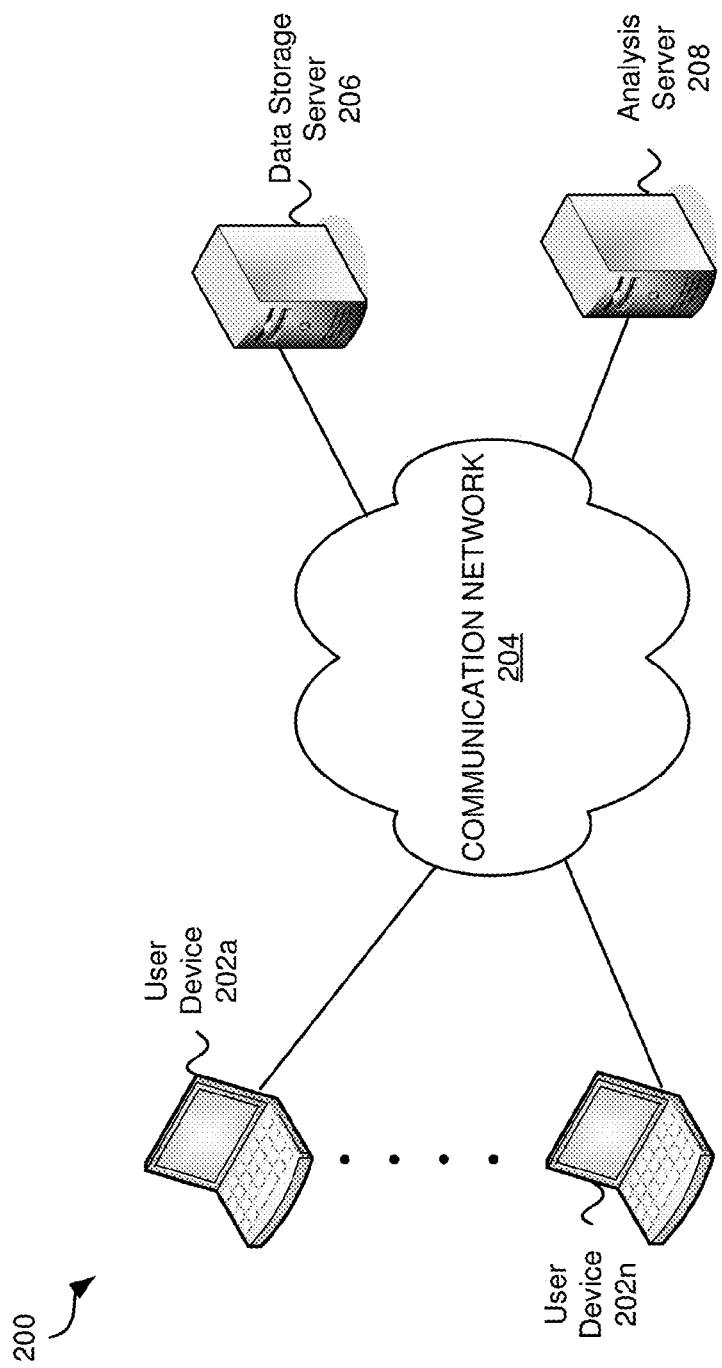
FIG. 2 is an exemplary environment in which embodiments may be practiced.

FIG. 2 is an exemplary environment 200 in which embodiments may be practiced. In various embodiments, data analysis and interactive visualization may be performed locally (e.g., with software and/or hardware on a local digital device), across a network (e.g., via cloud computing), or a combination of both. In many of these embodiments, a data structure is accessed to obtain the data for the analysis, the analysis is performed based on properties and parameters selected by a user, and an interactive visualization is generated and displayed. There are many advantages between performing all or some activities locally and many advantages of performing all or some activities over a network.

Environment 200 comprises user devices 202a-202n, a communication network 204, data storage server 206, and analysis server 208. Environment 200 depicts an embodiment wherein functions are performed across a network. In this example, the user(s) may take advantage of cloud computing by storing data in a data storage server 206 over a communication network 204. The analysis server 208 may perform analysis and generation of an interactive visualization.

User devices 202a-202n may be any digital devices. A digital device is any device that comprises memory and a processor. Digital devices are further described in FIG. 2. The user devices 202a-202n may be any kind of digital device that may be used to access, analyze and/or view data including, but not limited to a desktop computer, laptop, notebook, or other computing device.

In various embodiments, a user, such as a data analyst, may generate a database or other data structure with the user device 202a to be saved to the data storage server 206. The user device 202a may communicate with the analysis server 208 via the communication network 204 to perform analysis, examination, and visualization of data within the database.

The user device 202a may comprise a client program for interacting with one or more applications on the analysis server 208. In other embodiments, the user device 202a may communicate with the analysis server 208 using a browser or other standard program. In various embodiments, the user device 202a communicates with the analysis server 208 via a virtual private network. Those skilled in the art will appreciate that that communication between the user device 202a, the data storage server 206, and/or the analysis server 208 may be encrypted or otherwise secured.

The communication network 204 may be any network that allows digital devices to communicate. The communication network 204 may be the Internet and/or include LAN and WANs. The communication network 204 may support wireless and/or wired communication.

The data storage server 206 is a digital device that is configured to store data. In various embodiments, the data storage server 206 stores databases and/or other data structures. The data storage server 206 may be a single server or a combination of servers. In one example the data storage server 206 may be a secure server wherein a user may store data over a secured connection (e.g., via https). The data may be encrypted and backed-up. In some embodiments, the data storage server 206 is operated by a third-party such as Amazon's S3 service.

The database or other data structure may comprise large high-dimensional datasets. These datasets are traditionally very difficult to analyze and, as a result, relationships within the data may not be identifiable using previous methods. Further, previous methods may be computationally inefficient.

The analysis server 208 is a digital device that may be configured to analyze data. In various embodiments, the analysis server may perform many functions to interpret, examine, analyze, and display data and/or relationships within data. In some embodiments, the analysis server 208 performs, at least in part, topological analysis of large datasets applying metrics, filters, and resolution parameters chosen by the user. The analysis is further discussed in FIG. 8 herein.

The analysis server 208 may generate an interactive visualization of the output of the analysis. The interactive visualization allows the user to observe and explore relationships in the data. In various embodiments, the interactive visualization allows the user to select nodes comprising data that has been clustered. The user may then access the underlying data, perform further analysis (e.g., statistical analysis) on the underlying data, and manually reorient the graph(s) (e.g., structures of nodes and edges described herein) within the interactive visualization. The analysis server 208 may also allow for the user to interact with the data, see the graphic result. The interactive visualization is further discussed in FIGS. 9-11.

In some embodiments, the analysis server 208 interacts with the user device(s) 202*a*-202*n* over a private and/or secure communication network. The user device 202*a* may comprise a client program that allows the user to interact with the data storage server 206, the analysis server 208, another user device (e.g., user device 202*n*), a database, and/or an analysis application executed on the analysis server 208.

Those skilled in the art will appreciate that all or part of the data analysis may occur at the user device 202*a*. Further, all or part of the interaction with the visualization (e.g., graphic) may be performed on the user device 202*a*.

Although two user devices 202*a* and 202*n* are depicted, those skilled in the art will appreciate that there may be any number of user devices in any location (e.g., remote from each other). Similarly, there may be any number of communication networks, data storage servers, and analysis servers.

Cloud computing may allow for greater access to large datasets (e.g., via a commercial storage service) over a faster connection. Further, those skilled in the art will appreciate that services and computing resources offered to the user(s) may be scalable.

Figure 3:
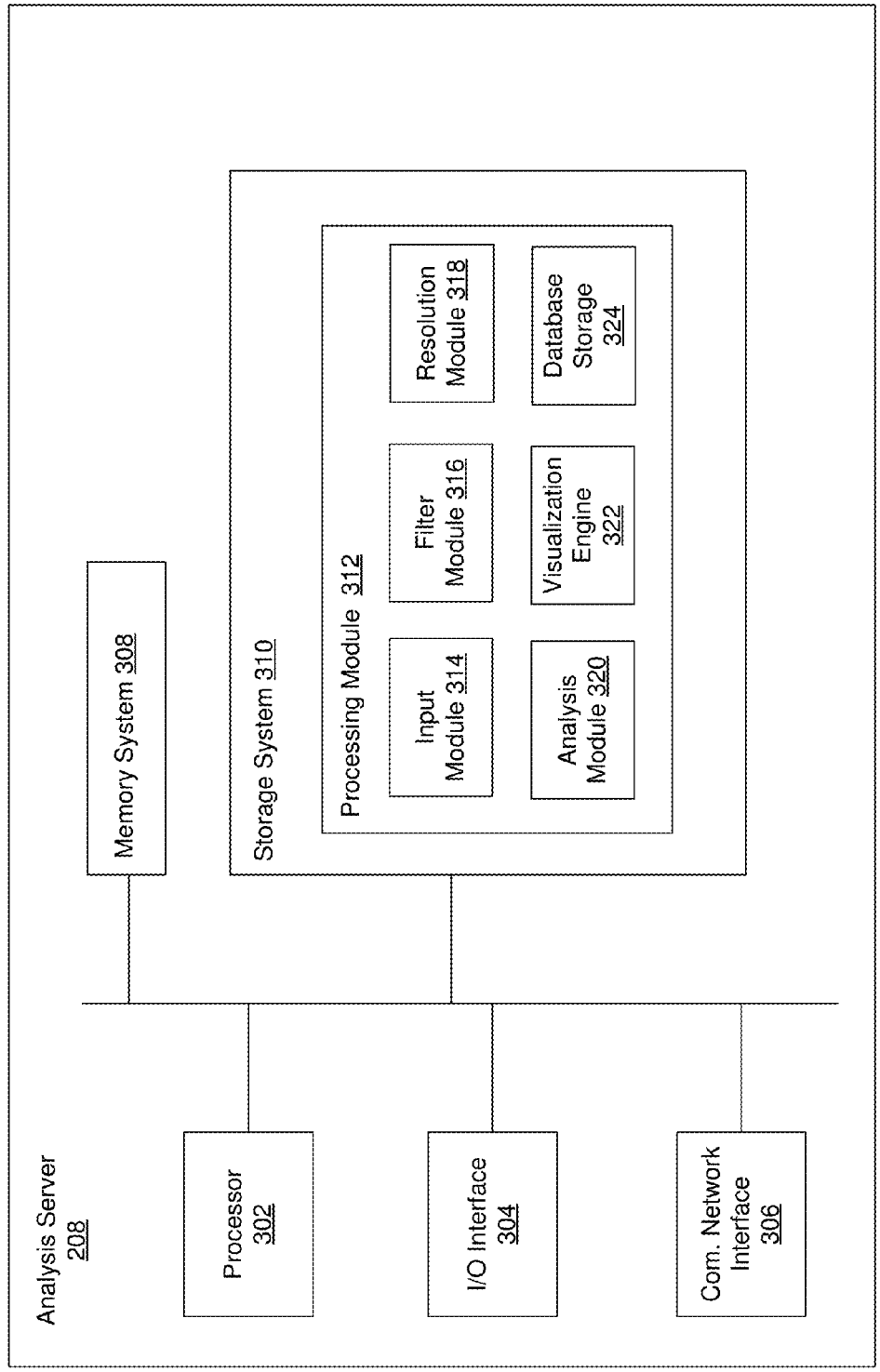
FIG. 3 is a block diagram of an exemplary analysis server.

FIG. 3 is a block diagram of an exemplary analysis server 208. In exemplary embodiments, the analysis server 208 comprises a processor 302, input/output (I/O) interface 304, a communication network interface 306, a memory system 308, a storage system 310, and a processing module 312. The processor 302 may comprise any processor or combination of processors with one or more cores.

The input/output (I/O) device 304 may comprise interfaces for various I/O devices such as, for example, a keyboard, mouse, and display device. The exemplary communication network interface 306 is configured to allow the analysis server 208 to communication with the communication network 204 (see FIG. 2). The communication network interface 306 may support communication over an Ethernet connection, a serial connection, a parallel connection, and/or an ATA connection. The communication network interface 306 may also support wireless communication (e.g., 802.11 a/b/g/n, WiMax, LTE, WiFi). It will be apparent to those skilled in the art that the communication network interface 306 can support many wired and wireless standards.

The memory system 308 may be any kind of memory including RAM, ROM, or flash, cache, virtual memory, etc. In various embodiments, working data is stored within the memory system 308. The data within the memory system 308 may be cleared or ultimately transferred to the storage system 310.

The storage system 310 includes any storage configured to retrieve and store data. Some examples of the storage system 310 include flash drives, hard drives, optical drives, and/or magnetic tape. Each of the memory system 308 and the storage system 310 comprises a computer-readable medium, which stores instructions (e.g., software programs) executable by processor 302.

The storage system 310 comprises a plurality of modules utilized by embodiments of discussed herein. A module may be hardware, software (e.g., including instructions executable by a processor), or a combination of both. In one embodiment, the storage system 310 comprises a processing module 312 which comprises an input module 314, a filter module 316, a resolution module 318, an analysis module 320, a visualization engine 322, and database storage 324. Alternative embodiments of the analysis server 208 and/or the storage system 310 may comprise more, less, or functionally equivalent components and modules.

The input module 314 may be configured to receive commands and preferences from the user device 202*a*. In various examples, the input module 314 receives selections from the user which will be used to perform the analysis. The output of the analysis may be an interactive visualization.

The input module 314 may provide the user a variety of interface windows allowing the user to select and access a database, choose fields associated with the database, choose a metric, choose one or more filters, and identify resolution parameters for the analysis. In one example, the input module 314 receives a database identifier and accesses a large multi-dimensional database. The input module 314 may scan the database and provide the user with an interface window allowing the user to identify an ID field. An ID field is an identifier for each data point. In one example, the identifier is unique. The same column name may be present in the table from which filters are selected. After the ID field is selected, the input module 314 may then provide the user with another interface window to allow the user to choose one or more data fields from a table of the database.

Although interactive windows may be described herein, those skilled in the art will appreciate that any window, graphical user interface, and/or command line may be used to receive or prompt a user or user device 202*a* for information.

The filter module 316 may subsequently provide the user with an interface window to allow the user to select a metric to be used in analysis of the data within the chosen data fields. The filter module 316 may also allow the user to select and/or define one or more filters.

The resolution module 218 may allow the user to select a resolution, including filter parameters. In one example, the user enters a number of intervals and a percentage overlap for a filter.

The analysis module 320 may perform data analysis based on the database and the information provided by the user. In various embodiments, the analysis module 320 performs an algebraic topological analysis to identify structures and relationships within data and clusters of data. Those skilled in the art will appreciate that the analysis module 320 may use parallel algorithms or use generalizations of various statistical techniques (e.g., generalizing the bootstrap to zig-zag methods) to increase the size of data sets that can be processed. The analysis is further discussed in FIG. 8. Those skilled in the art will appreciate that the analysis module 320 is not limited to algebraic topological analysis but may perform any analysis.

The visualization engine 322 generates an interactive visualization including the output from the analysis module 320. The interactive visualization allows the user to see all or part of the analysis graphically. The interactive visualization also allows the user to interact with the visualization. For example, the user may select portions of a graph from within the visualization to see and/or interact with the underlying data and/or underlying analysis. The user may then change the parameters of the analysis (e.g., change the metric, filter(s), or resolution(s)) which allows the user to visually identify relationships in the data that may be otherwise undetectable using prior means. The interactive visualization is further described in FIGS. 9-11.

The database storage 324 is configured to store all or part of the database that is being accessed. In some embodiments, the database storage 324 may store saved portions of the database. Further, the database storage 324 may be used to store user preferences, parameters, and analysis output thereby allowing the user to perform many different functions on the database without losing previous work.

Those skilled in the art will appreciate that that all or part of the processing module 312 may be at the user device 202a or the database storage server 206. In some embodiments, all or some of the functionality of the processing module 312 may be performed by the user device 202a.

In various embodiments, systems and methods discussed herein may be implemented with one or more digital devices. In some examples, some embodiments discussed herein may be implemented by a computer program (instructions) executed by a processor. The computer program may provide a graphical user interface. Although such a computer program is discussed, those skilled in the art will appreciate that embodiments may be performed using any of the following, either alone or in combination, including, but not limited to, a computer program, multiple computer programs, firmware, and/or hardware.

A module and/or engine may include any processor or combination of processors. In some examples, a module and/or engine may include or be a part of a processor, digital signal processor (DSP), application specific integrated circuit (ASIC), an integrated circuit, and/or the like. In various embodiments, the module and/or engine may be software or firmware.

Figure 4:
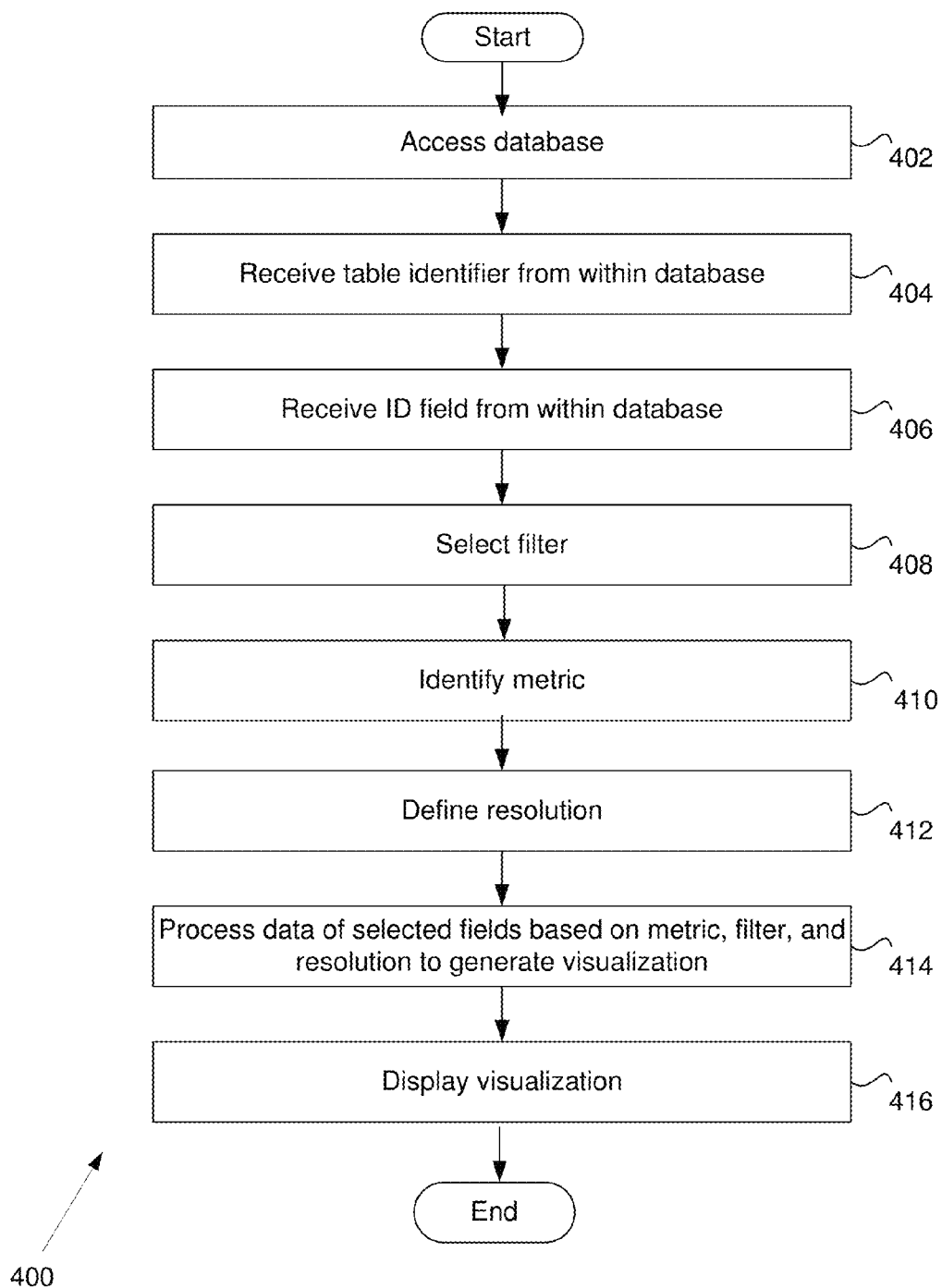
FIG. 4 is a flow chart depicting an exemplary method of dataset analysis and visualization in some embodiments.

FIG. 4 is a flow chart 400 depicting an exemplary method of dataset analysis and visualization in some embodiments. In step 402, the input module 314 accesses a database. The database may be any data structure containing data (e.g., a very large dataset of multidimensional data). In some embodiments, the database may be a relational database. In some examples, the relational database may be used with MySQL, Oracle, Micosoft SQL Server, Aster nCluster, Teradata, and/or Vertica. Those skilled in the art will appreciate that the database may not be a relational database.

In some embodiments, the input module 314 receives a database identifier and a location of the database (e.g., the data storage server 206) from the user device 202a (see FIG. 2). The input module 314 may then access the identified database. In various embodiments, the input module 314 may read data from many different sources, including, but not limited to MS Excel files, text files (e.g., delimited or CSV), Matlab .mat format, or any other file.

In some embodiments, the input module 314 receives an IP address or hostname of a server hosting the database, a username, password, and the database identifier. This information (herein referred to as "connection information") may be cached for later use. Those skilled in the art will appreciate that the database may be locally accessed and that all, some, or none of the connection information may be required. In one example, the user device 202a may have full access to the database stored locally on the user device 202a so the IP address is unnecessary. In another example, the user device 202a may already have loaded the database and the input module 314 merely begins by accessing the loaded database.

In various embodiments, the identified database stores data within tables. A table may have a "column specification" which stores the names of the columns and their data types. A "row" in a table, may be a tuple with one entry for each column of the correct type. In one example, a table to store employee records might have a column specification such as:

employee_id primary key int (this may store the employee's ID as an integer, and uniquely identifies a row)
    age int
    gender char(1) (gender of the employee may be a single character either M or F)
    salary double (salary of an employee may be a floating point number)
    name varchar (name of the employee may be a variable-length string)

In this example, each employee corresponds to a row in this table. Further, the tables in this exemplary relational database are organized into logical units called databases. An analogy to file systems is that databases can be thought of as folders and files as tables. Access to databases may be controlled by the database administrator by assigning a username/password pair to authenticate users.

Once the database is accessed, the input module 314 may allow the user to access a previously stored analysis or to begin a new analysis. If the user begins a new analysis, the input module 314 may provide the user device 202a with an interface window allowing the user to identify a table from within the database. In one example, the input module 314 provides a list of available tables from the identified database.

In step 404, the input module 314 receives a table identifier identifying a table from within the database. The input module 314 may then provide the user with a list of available ID fields from the table identifier. In step 406, the input module 314 receives the ID field identifier from the user and/or user device 202a. The ID field is, in some embodiments, the primary key.

Having selected the primary key, the input module 314 may generate a new interface window to allow the user to select data fields for analysis. In step 408, the input module 314 receives data field identifiers from the user device 202a. The data within the data fields may be later analyzed by the analysis module 320.

In step 410, the filter module 316 identifies a metric. In some embodiments, the filter module 316 and/or the input module 314 generates an interface window allowing the user of the user device 202a options for a variety of different metrics and filter preferences. The interface window may be a drop down menu identifying a variety of distance metrics to be used in the analysis. Metric options may include, but are not limited to, Euclidean, DB Metric, variance normalized Euclidean, and total normalized Euclidean. The metric and the analysis are further described herein.

In step 412, the filter module 316 selects one or more filters. In some embodiments, the user selects and provides filter identifier(s) to the filter module 316. The role of the filters in the analysis is also further described herein. The filters, for example, may be user defined, geometric, or based on data which has been pre-processed. In some embodiments, the data based filters are numerical arrays which can assign a set of real numbers to each row in the table or each point in the data generally.

A variety of geometric filters may be available for the user to choose. Geometric filters may include, but are not limited to:
    Density
    L1 Eccentricity
    L-infinity Eccentricity
    Witness based Density
    Witness based Eccentricity Eccentricity as distance from a fixed point
Approximate Kurtosis of the Eccentricity In step 414, the resolution module 218 defines the resolution to be used with a filter in the analysis. The resolution may comprise a number of intervals and an overlap parameter. In various embodiments, the resolution module 218 allows the user to adjust the number of intervals and overlap parameter (e.g., percentage overlap) for one or more filters.

In step 416, the analysis module 320 processes data of selected fields based on the metric, filter(s), and resolution(s) to generate the visualization. This process is discussed in FIG. 8.

In step 418, the visualization module 322 displays the interactive visualization. In various embodiments, the visualization may be rendered in two or three dimensional space. The visualization module 322 may use an optimization algorithm for an objective function which is correlated with good visualization (e.g., the energy of the embedding). The visualization may show a collection of nodes corresponding to each of the partial clusters in the analysis output and edges connecting them as specified by the output. The interactive visualization is further discussed in FIGS. 9-11.

Although many examples discuss the input module 314 as providing interface windows, those skilled in the art will appreciate that all or some of the interface may be provided by a client on the user device 202a. Further, in some embodiments, the user device 202a may be running all or some of the processing module 212.

Figure 5:
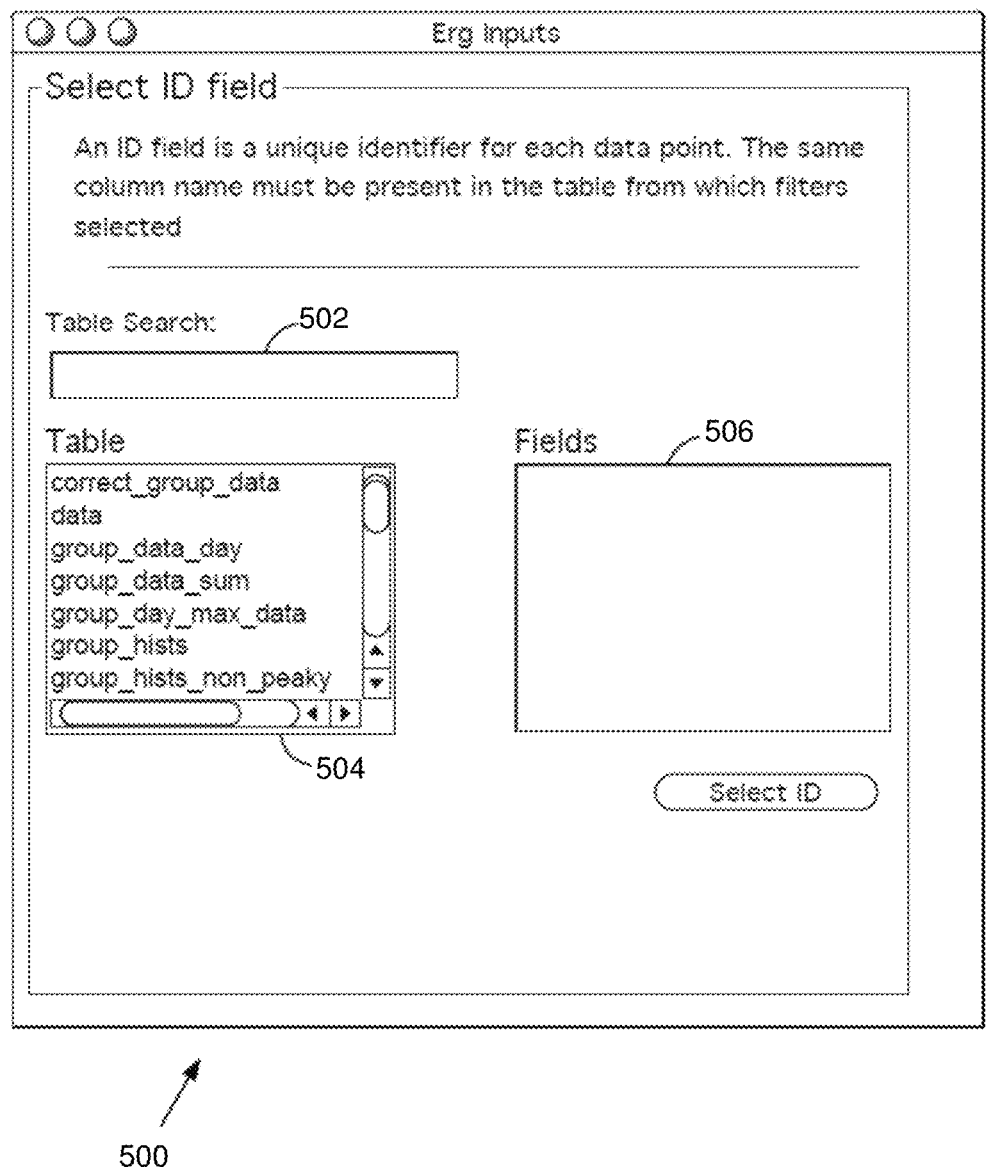
FIG. 5 is an exemplary ID field selection interface window in some embodiments.
Figure 6A:
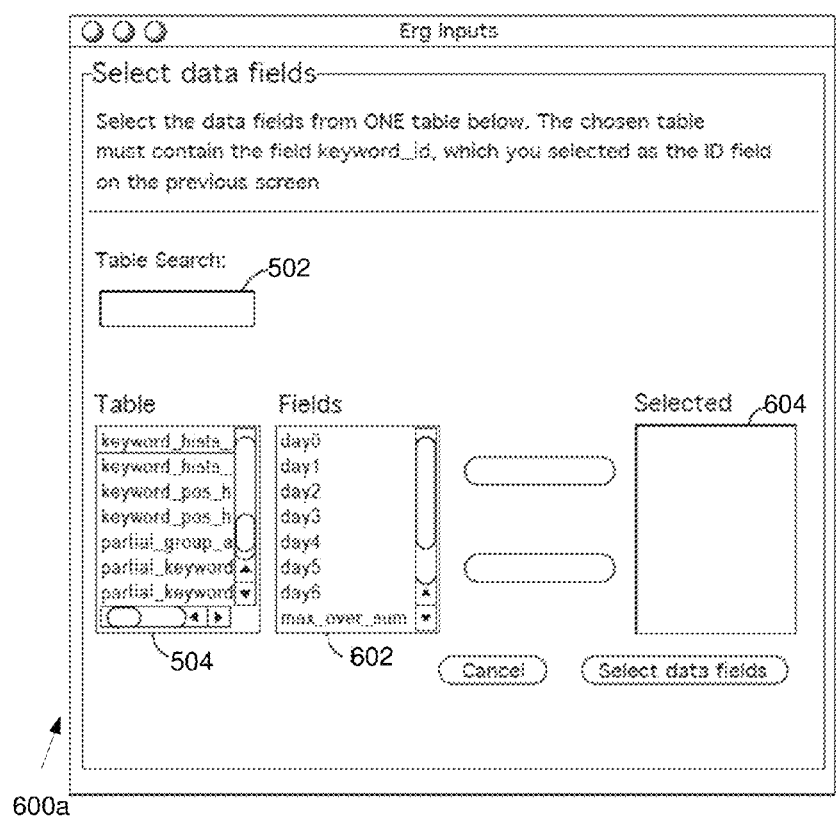
FIG. 6a is an exemplary data field selection interface window in some embodiments.
Figure 6B:
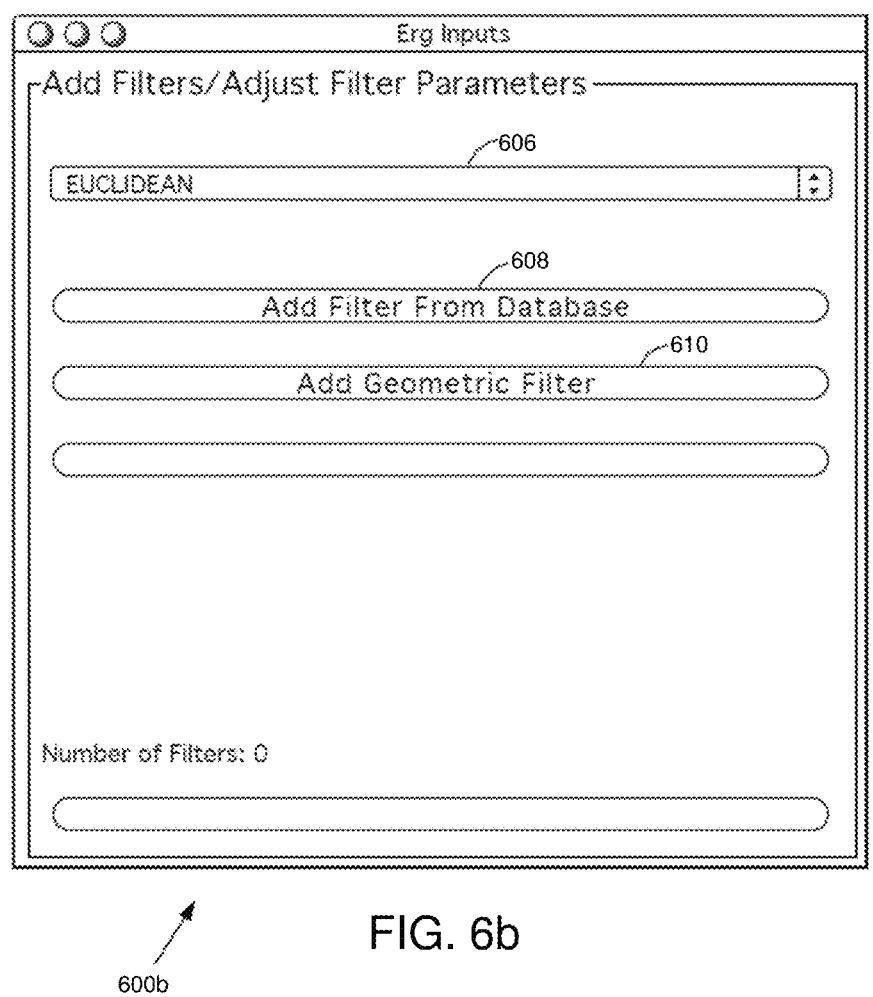
FIG. 6b is an exemplary metric and filter selection interface window in some embodiments.
Figure 7:
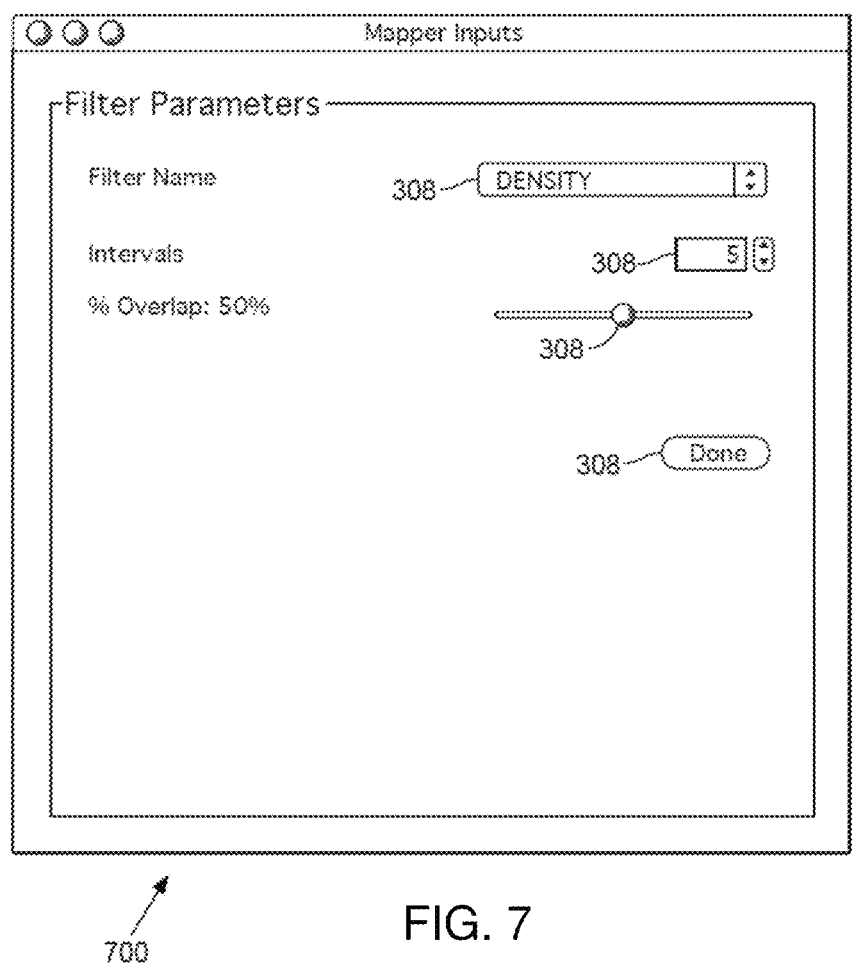
FIG. 7 is an exemplary filter parameter interface window in some embodiments.

FIGS. 5-7 depict various interface windows to allow the user to make selections, enter information (e.g., fields, metrics, and filters), provide parameters (e.g., resolution), and provide data (e.g., identify the database) to be used with analysis. Those skilled in the art will appreciate that any graphical user interface or command line may be used to make selections, enter information, provide parameters, and provide data.

FIG. 5 is an exemplary ID field selection interface window 500 in some embodiments. The ID field selection interface window 500 allows the user to identify an ID field. The ID field selection interface window 500 comprises a table search field 502, a table list 504, and a fields selection window 506.

In various embodiments, the input module 314 identifies and accesses a database from the database storage 324, user device 202a, or the data storage server 206. The input module 314 may then generate the ID field selection interface window 500 and provide a list of available tables of the selected database in the table list 504. The user may click on a table or search for a table by entering a search query (e.g., a keyword) in the table search field 502. Once a table is identified (e.g., clicked on by the user), the fields selection window 506 may provide a list of available fields in the selected table. The user may then choose a field from the fields selection window 506 to be the ID field. In some embodiments, any number of fields may be chosen to be the ID field(s).

FIG. 6a is an exemplary data field selection interface window 600a in some embodiments. The data field selection interface window 600a allows the user to identify data fields. The data field selection interface window 600a comprises a table search field 502, a table list 504, a fields selection window 602, and a selected window 604.

In various embodiments, after selection of the ID field, the input module 314 provides a list of available tables of the selected database in the table list 504. The user may click on a table or search for a table by entering a search query (e.g., a keyword) in the table search field 502. Once a table is identified (e.g., clicked on by the user), the fields selection window 506 may provide a list of available fields in the selected table. The user may then choose any number of fields from the fields selection window 602 to be data fields. The selected data fields may appear in the selected window 604. The user may also deselect fields that appear in the selected window 604.

Those skilled in the art will appreciate that the table selected by the user in the table list 504 may be the same table selected with regard to FIG. 5. In some embodiments, however, the user may select a different table. Further, the user may, in various embodiments, select fields from a variety of different tables.

FIG. 6b is an exemplary metric and filter selection interface window 600b in some embodiments. The metric and filter selection interface window 600b allows the user to identify a metric, add filter(s), and adjust filter parameters. The metric and filter selection interface window 600b comprises a metric pull down menu 606, an add filter from database button 608, and an add geometric filter button 610.

In various embodiments, the user may click on the metric pull down menu 606 to view a variety of metric options. Various metric options are described herein. In some embodiments, the user may define a metric. The user defined metric may then be used with the analysis.

In one example, finite metric space data may be constructed from a data repository (i.e., database, spreadsheet, or Matlab file). This may mean selecting a collection of fields whose entries will specify the metric using the standard Euclidean metric for these fields, when they are floating point or integer variables. Other notions of distance, such as graph distance between collections of points, may be supported.

The analysis module 320 may perform analysis using the metric as a part of a distance function. The distance function can be expressed by a formula, a distance matrix, or other routine which computes it. The user may add a filter from a database by clicking on the add filter from database button 608. The metric space may arise from a relational database, a Matlab file, an Excel spreadsheet, or other methods for storing and manipulating data. The metric and filter selection interface window 600b may allow the user to browse for other filters to use in the analysis. The analysis and metric function are further described in FIG. 8.

The user may also add a geometric filter 610 by clicking on the add geometric filter button 610. In various embodiments, the metric and filter selection interface window 600b may provide a list of geometric filters from which the user may choose.

FIG. 7 is an exemplary filter parameter interface window 700 in some embodiments. The filter parameter interface window 700 allows the user to determine a resolution for one or more selected filters (e.g., filters selected in the metric and filter selection interface window 600). The filter parameter interface window 700 comprises a filter name menu 702, an interval field 704, an overlap bar 706, and a done button 708.

The filter parameter interface window 700 allows the user to select a filter from the filter name menu 702. In some embodiments, the filter name menu 702 is a drop down box indicating all filters selected by the user in the metric and filter selection interface window 600. Once a filter is chosen, the name of the filter may appear in the filter name menu 702. The user may then change the intervals and overlap for one, some, or all selected filters.

The interval field 704 allows the user to define a number of intervals for the filter identified in the filter name menu

702. The user may enter a number of intervals or scroll up or down to get to a desired number of intervals. Any number of intervals may be selected by the user. The function of the intervals is further discussed in FIG. 8.

The overlap bar 706 allows the user to define the degree of overlap of the intervals for the filter identified in the filter name menu 702. In one example, the overlap bar 706 includes a slider that allows the user to define the percentage overlap for the interval to be used with the identified filter. Any percentage overlap may be set by the user.

Once the intervals and overlap are defined for the desired filters, the user may click the done button. The user may then go back to the metric and filter selection interface window 600 and see a new option to run the analysis. In some embodiments, the option to run the analysis may be available in the filter parameter interface window 700. Once the analysis is complete, the result may appear in an interactive visualization which is further described in FIGS. 9-11.

Those skilled in the art will appreciate that that interface windows in FIGS. 4-7 are exemplary. The exemplary interface windows are not limited to the functional objects (e.g., buttons, pull down menus, scroll fields, and search fields) shown. Any number of different functional objects may be used. Further, as described herein, any other interface, command line, or graphical user interface may be used.

Figure 8:
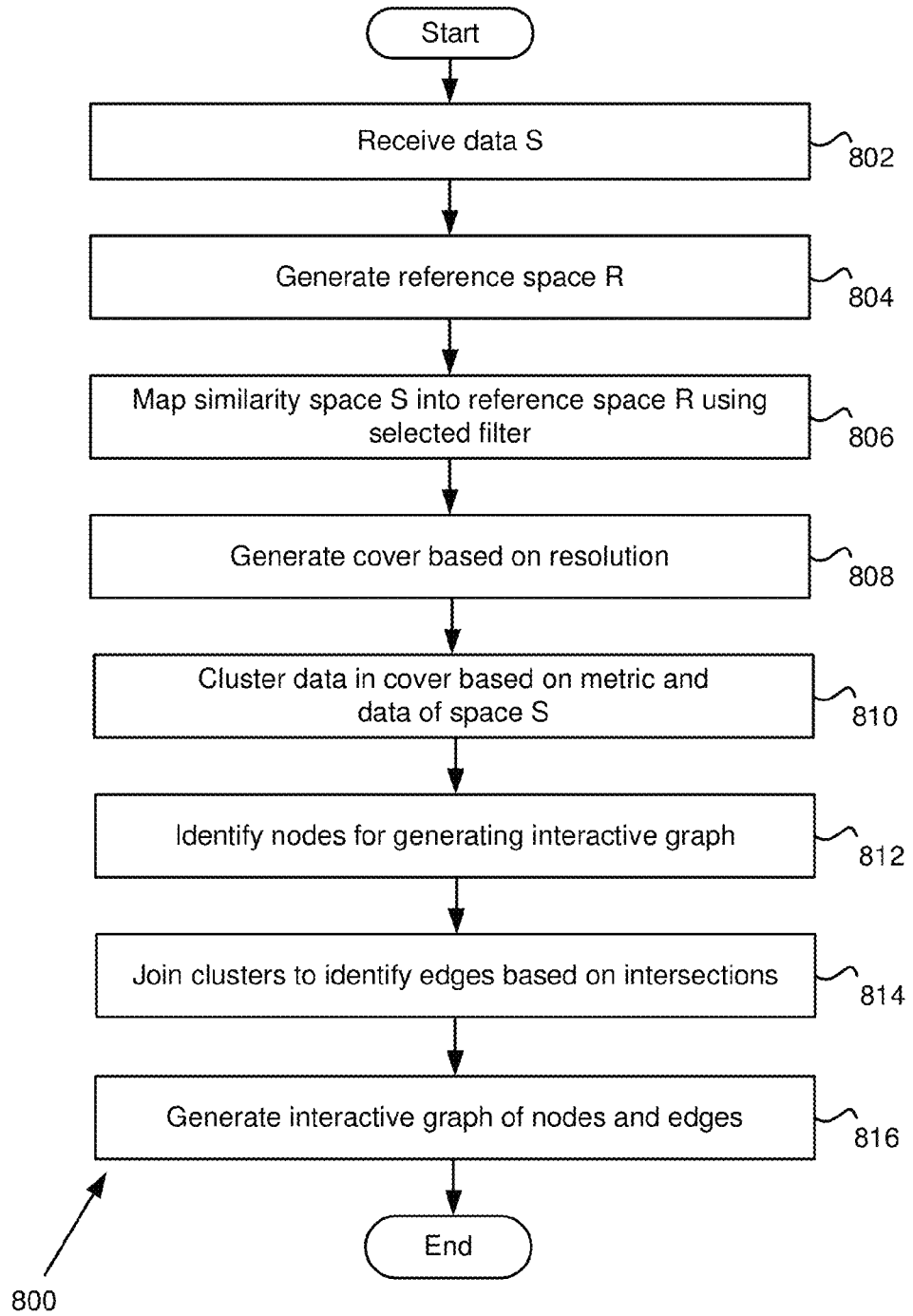
FIG. 8 is a flowchart for data analysis and generating a visualization in some embodiments.

FIG. 8 is a flowchart 800 for data analysis and generating an interactive visualization in some embodiments. In various embodiments, the processing on data and user-specified options is motivated by techniques from topology and, in some embodiments, algebraic topology. These techniques may be robust and general. In one example, these techniques apply to almost any kind of data for which some qualitative idea of "closeness" or "similarity" exists. The techniques discussed herein may be robust because the results may be relatively insensitive to noise in the data, user options, and even to errors in the specific details of the qualitative measure of similarity, which, in some embodiments, may be generally refer to as "the distance function" or "metric." Those skilled in the art will appreciate that while the description of the algorithms below may seem general, the implementation of techniques described herein may apply to any level of generality.

In step 802, the input module 314 receives data S. In one example, a user identifies a data structure and then identifies ID and data fields. Data S may be based on the information within the ID and data fields. In various embodiments, data S is treated as being processed as a finite "similarity space," where data S has a real-valued function d defined on pairs of points s and t in S, such that:

$$d(s,s)=0$$

$$d(s,t)=d(t,s)$$

$$d(s,t)>=0$$

These conditions may be similar to requirements for a finite metric space, but the conditions may be weaker. In various examples, the function is a metric.

Those skilled in the art will appreciate that data S may be a finite metric space, or a generalization thereof, such as a graph or weighted graph. In some embodiments, data S be specified by a formula, an algorithm, or by a distance matrix which specifies explicitly every pairwise distance.

In step 804, the input module 314 generates reference space R. In one example, reference space R may be a well-known metric space (e.g., such as the real line). The reference space R may be defined by the user. In step 806, the analysis module 320 generates a map ref( ) from S into R. The map ref( ) from S into R may be called the "reference map."

In one example, a reference of map from S is to a reference metric space R. R may be Euclidean space of some dimension, but it may also be the circle, torus, a tree, or other metric space. The map can be described by one or more filters (i.e., real valued functions on S). These filters can be defined by geometric invariants, such as the output of a density estimator, a notion of data depth, or functions specified by the origin of S as arising from a data set.

In step 808, the resolution module 218 generates a cover of R based on the resolution received from the user (e.g., filter(s), intervals, and overlap—see FIG. 7). The cover of R may be a finite collection of open sets (in the metric of R) such that every point in R lies in at least one of these sets. In various examples, R is k-dimensional Euclidean space, where k is the number of filter functions. More precisely in this example, R is a box in k-dimensional Euclidean space given by the product of the intervals [min_k, max_k], where min_k is the minimum value of the k-th filter function on S, and max_k is the maximum value.

For example, suppose there are 2 filter functions, F1 and F2, and that F1's values range from −1 to +1, and F2's values range from 0 to 5. Then the reference space is the rectangle in the x/y plane with corners (−1,0), (1,0), (−1, 5), (1, 5), as every point s of S will give rise to a pair (F1(s), F2(s)) that lies within that rectangle.

In various embodiments, the cover of R is given by taking products of intervals of the covers of [min_k,max_k] for each of the k filters. In one example, if the user requests 2 intervals and a 50% overlap for F1, the cover of the interval [−1,+1] will be the two intervals (−1.5, 0.5), (−0.5, 1.5). If the user requests 5 intervals and a 30% overlap for F2, then that cover of [0, 5] will be (−0.3, 1.3), (0.7, 2.3), (1.7, 3.3), (2.7, 4.3), (3.7, 5.3). These intervals may give rise to a cover of the 2-dimensional box by taking all possible pairs of intervals where the first of the pair is chosen from the cover for F1 and the second from the cover for F2. This may give rise to 2*5, or 10, open boxes that covered the 2-dimensional reference space. However, those skilled in the art will appreciate that the intervals may not be uniform, or that the covers of a k-dimensional box may not be constructed by products of intervals. In some embodiments, there are many other choices of intervals. Further, in various embodiments, a wide range of covers and/or more general reference spaces may be used.

In one example, given a cover, $C_1, \ldots, C_m$, of R, the reference map is used to assign a set of indices to each point in S, which are the indices of the $C_j$ such that ref(s) belongs to $C_j$. This function may be called ref_tags(s). In a language such as Java, ref_tags would be a method that returned an int[ ]. Since the C's cover R in this example, ref(s) must lie in at least one of them, but the elements of the cover usually overlap one another, which means that points that "land near the edges" may well reside in multiple cover sets. In considering the two filter example, if F1(s) is −0.99, and F2(s) is 0.001, then ref(s) is (−0.99, 0.001), and this lies in the cover element (−1.5, 0.5)×(−0.3,1.3). Supposing that was labeled $C_1$, the reference map may assign s to the set {1}. On the other hand, if t is mapped by F1, F2 to (0.1, 2.1), then ref(t) will be in (−1.5,0.5)×(0.7, 2.3), (−0.5, 1.5)×(0.7, 2.3), (−1.5,0.5)×(1.7,3.3), and (−0.5, 1.5)×(1.7,3.3), so the set of indices would have four elements for t.

Having computed, for each point, which "cover tags" it is assigned to, for each cover element, $C_d$, the points may be constructed, whose tags include d, as set S(d). This may mean that every point s is in S(d) for some d, but some points may belong to more than one such set. In some embodiments, there is, however, no requirement that each S(d) is non-empty, and it is frequently the case that some of these sets are empty. In the non-parallelized version of some embodiments, each point x is processed in turn, and x is inserted into a hash-bucket for each j in ref_tags(t) (that is, this may be how S(d) sets are computed).

Those skilled in the art will appreciate that the cover of the reference space R may be controlled by the number of intervals and the overlap identified in the resolution (e.g., see FIG. 7). For example, the more intervals, the finer the resolution in S—that is, the fewer points in each S(d), but the more similar (with respect to the filters) these points may be. The greater the overlap, the more times that clusters in S(d) may intersect clusters in S(e)—this means that more "relationships" between points may appear, but, in some embodiments, the greater the overlap, the more likely that accidental relationships may appear.

In step 810, the analysis module 320 clusters each S(d) based on the metric, filter, and the space S. In some embodiments, a dynamic single-linkage clustering algorithm may be used to partition S(d). Those skilled in the art will appreciate that any number of clustering algorithms may be used with embodiments discussed herein. For example, the clustering scheme may be k-means clustering for some k, single linkage clustering, average linkage clustering, or any method specified by the user.

The significance of the user-specified inputs may now be seen. In some embodiments, a filter may amount to a "forced stretching" in a certain direction. In some embodiments, the analysis module 320 may not cluster two points unless ALL of the filter values are sufficiently "related" (recall that while normally related may mean "close," the cover may impose a much more general relationship on the filter values, such as relating two points s and t if ref(s) and ref(t) are sufficiently close to the same circle in the plane). In various embodiments, the ability of a user to impose one or more "critical measures" makes this technique more powerful than regular clustering, and the fact that these filters can be anything, is what makes it so general.

The output may be a simplicial complex, from which one can extract its 1-skeleton. The nodes of the complex may be partial clusters, (i.e., clusters constructed from subsets of S specified as the preimages of sets in the given covering of the reference space R).

In step 812, the visualization engine 322 identifies nodes which are associated with a subset of the partition elements of all of the S(d) for generating an interactive visualization. For example, suppose that S={1, 2, 3, 4}, and the cover is $C_1, C_2, C_3$. Then if ref_tags(1)={1, 2, 3} and ref_tags(2)={2, 3}, and ref_tags(3)={3}, and finally ref_tags(4)={1, 3}, then S(1) in this example is {1, 4}, S(2)={1,2}, and S(3)={1, 2, 3, 4}. If 1 and 2 are close enough to be clustered, and 3 and 4 are, but nothing else, then the clustering for S(1) may be {1} {3}, and for S(2) it may be {1,2}, and for S(3) it may be {1,2}, {3,4}. So the generated graph has, in this example, at most four nodes, given by the sets {1}, {4}, {1,2}, and {3,4} (note that {1,2} appears in two different clusterings). Of the sets of points that are used, two nodes intersect provided that the associated node sets have a non-empty intersection (although this could easily be modified to allow users to require that the intersection is "large enough" either in absolute or relative terms).

Nodes may be eliminated for any number of reasons. For example, a node may be eliminated as having too few points and/or not being connected to anything else. In some embodiments, the criteria for the elimination of nodes (if any) may be under user control or have application-specific requirements imposed on it. For example, if the points are consumers, for instance, clusters with too few people in area codes served by a company could be eliminated. If a cluster was found with "enough" customers, however, this might indicate that expansion into area codes of the other consumers in the cluster could be warranted.

In step 814, the visualization engine 322 joins clusters to identify edges (e.g., connecting lines between nodes). Once the nodes are constructed, the intersections (e.g., edges) may be computed "all at once," by computing, for each point, the set of node sets (not ref_tags, this time). That is, for each s in S, node_id_set(s) may be computed, which is an int[ ]. In some embodiments, if the cover is well behaved, then this operation is linear in the size of the set S, and we then iterate over each pair in node_id_set(s). There may be an edge between two node_id's if they both belong to the same node_id_set( ) value, and the number of points in the intersection is precisely the number of different node_id sets in which that pair is seen. This means that, except for the clustering step (which is often quadratic in the size of the sets S(d), but whose size may be controlled by the choice of cover), all of the other steps in the graph construction algorithm may be linear in the size of S, and may be computed quite efficiently.

Figure 10:
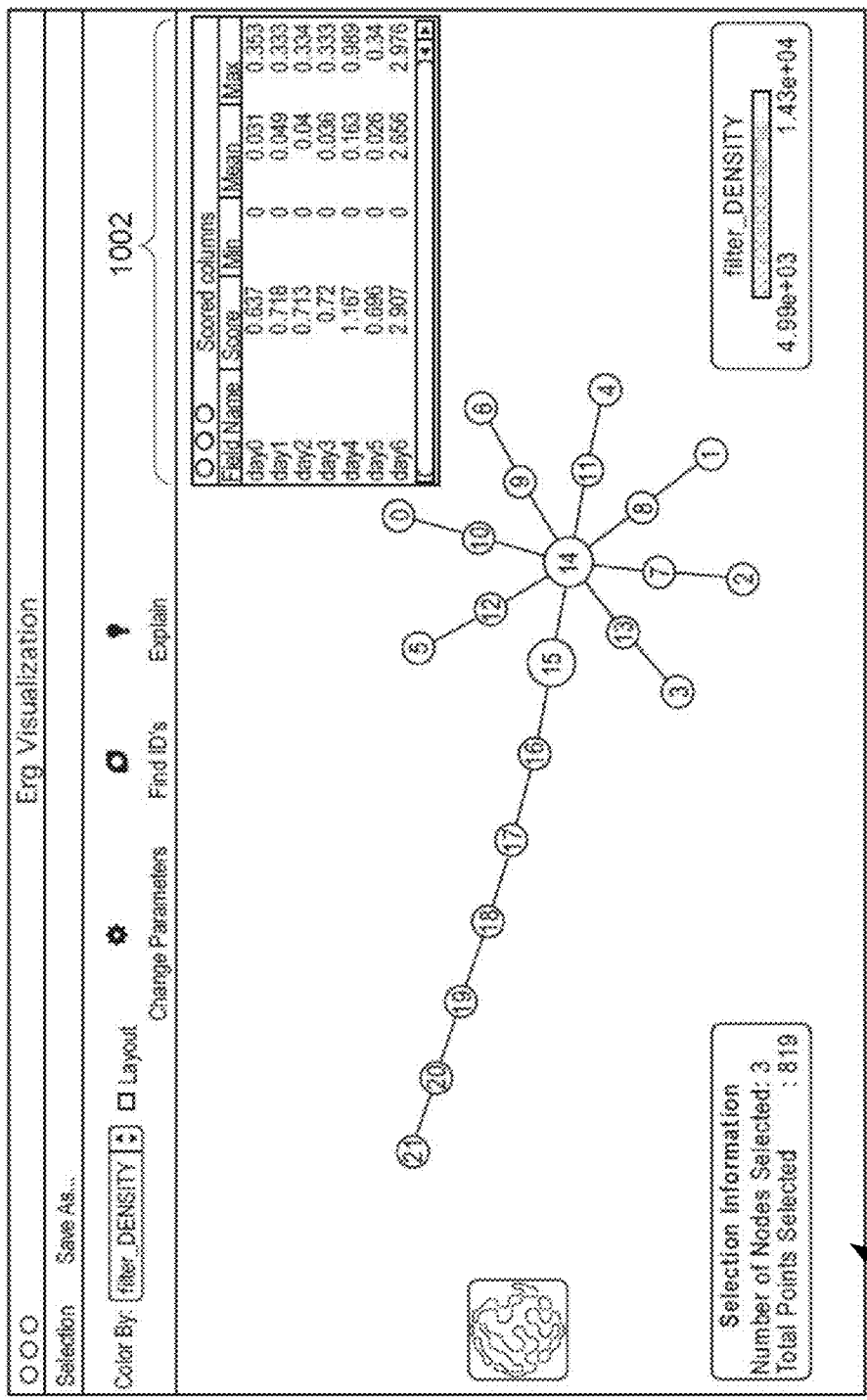
FIG. 10 is an exemplary interactive visualization displaying an explain information window in some embodiments.
Figure 11:
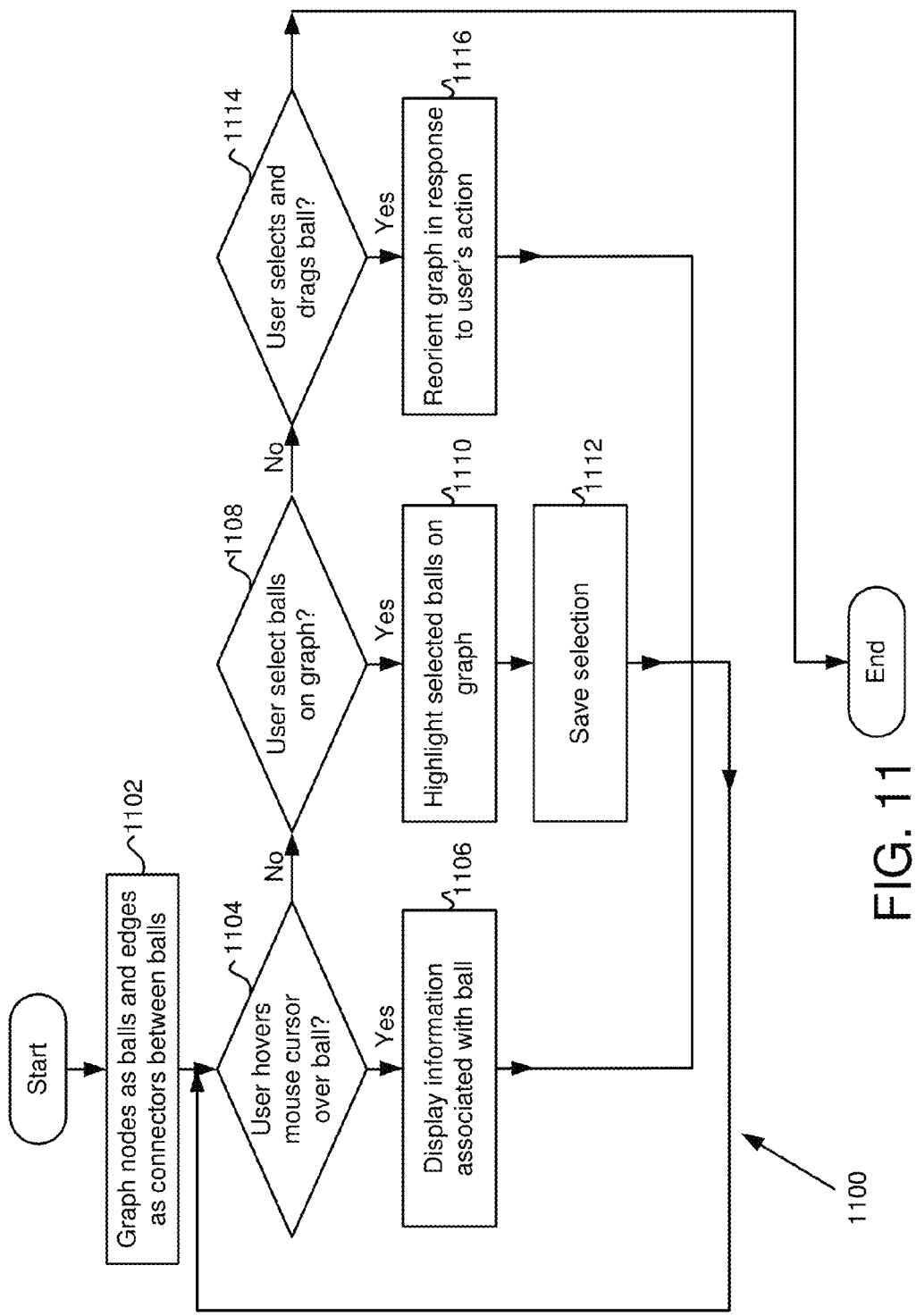
FIG. 11 is a flowchart of functionality of the interactive visualization in some embodiments.

In step 816, the visualization engine 322 generates the interactive visualization of interconnected nodes (e.g., nodes and edges displayed in FIGS. 10 and 11).

Those skilled in the art will appreciate that it is possible, in some embodiments, to make sense in a fairly deep way of connections between various ref( ) maps and/or choices of clustering. Further, in addition to computing edges (pairs of nodes), the embodiments described herein may be extended to compute triples of nodes, etc. For example, the analysis module 320 may compute simplicial complexes of any dimension (by a variety of rules) on nodes, and apply techniques from homology theory to the graphs to help users understand a structure in an automatic (or semi-automatic) way.

Further, those skilled in the art will appreciate that uniform intervals in the covering may not always be a good choice. For example, if the points are exponentially distributed with respect to a given filter, uniform intervals can fail—in such case adaptive interval sizing may yield uniformly-sized S(d) sets, for instance.

Further, in various embodiments, an interface may be used to encode techniques for incorporating third-party extensions to data access and display techniques. Further, an interface may be used to for third-party extensions to underlying infrastructure to allow for new methods for generating coverings, and defining new reference spaces.

Figure 9:
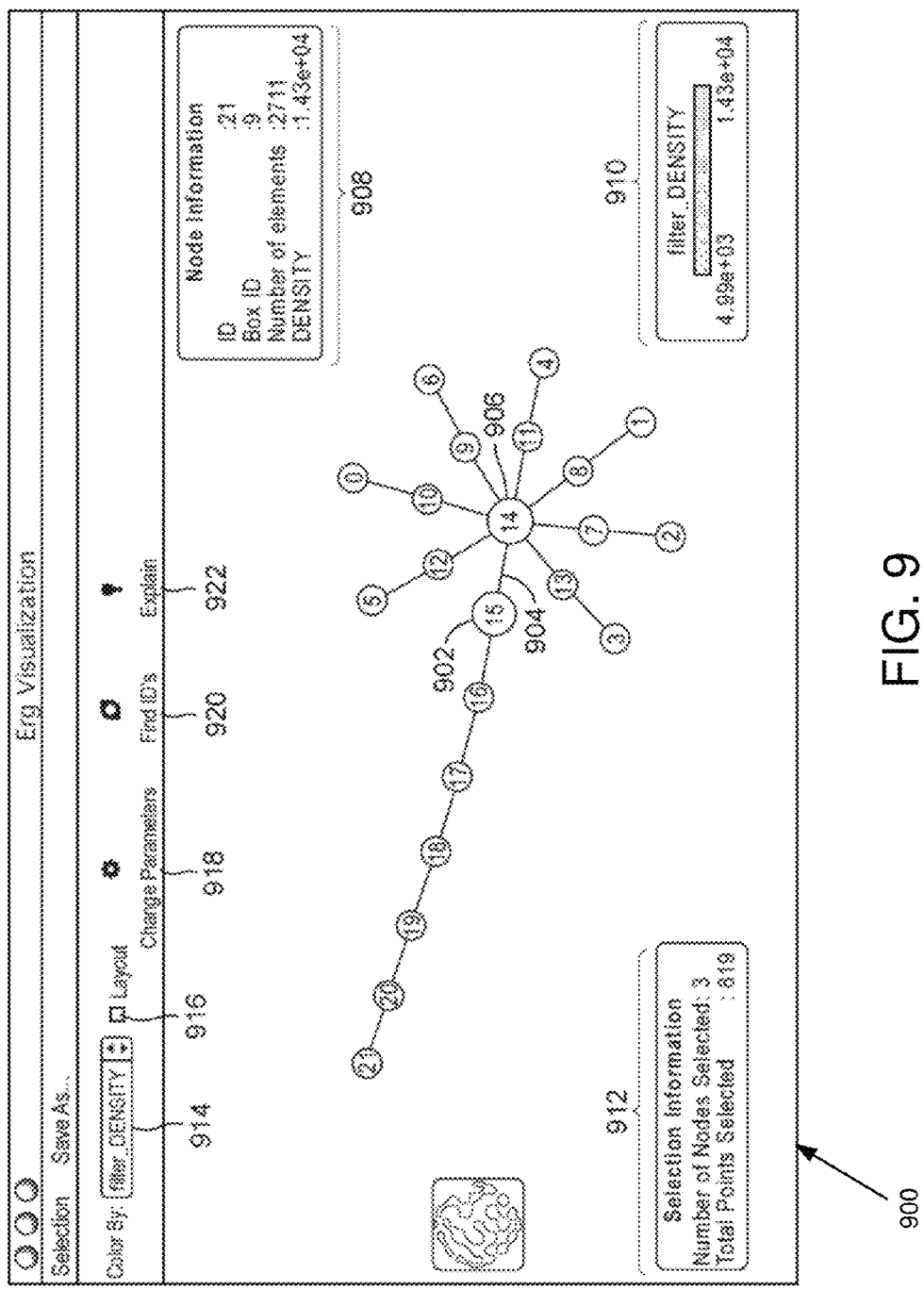
FIG. 9 is an exemplary interactive visualization in some embodiments.

FIG. 9 is an exemplary interactive visualization 900 in some embodiments. The display of the interactive visualization may be considered a "graph" in the mathematical sense. The interactive visualization comprises of two types of objects: nodes (e.g., nodes 902 and 906) (the colored balls) and the edges (e.g., edge 904) (the black lines). The edges connect pairs of nodes (e.g., edge 904 connects node 902 with node 906). As discussed herein, each node may represent a collection of data points (rows in the database identified by the user). In one example, connected nodes tend to include data points which are "similar to" (e.g., clustered with) each other. The collection of data points may be referred to as being "in the node." The interactive visualization may be two-dimensional, three-dimensional, or a combination of both.

In various embodiments, connected nodes and edges may form a graph or structure. There may be multiple graphs in the interactive visualization. In one example, the interactive visualization may display two or more unconnected structures of nodes and edges.

The visual properties of the nodes and edges (such as, but not limited to, color, stroke color, text, texture, shape, coordinates of the nodes on the screen) can encode any data based property of the data points within each node. For example, coloring of the nodes and/or the edges may indicate (but is not limited to) the following:

Values of fields or filters

Any general functions of the data in the nodes (e.g., if the data were unemployment rates by state, then GDP of the states may be identifiable by color the nodes)

Number of data points in the node

The interactive visualization 900 may contain a "color bar" 910 which may comprise a legend indicating the coloring of the nodes (e.g., balls) and may also identify what the colors indicate. For example, in FIG. 9, color bar 910 indicates that color is based on the density filter with blue (on the far left of the color bar 910) indicating "4.99e+03" and red (on the far right of the color bar 910) indicating "1.43e+04." In general this might be expanded to show any other legend by which nodes and/or edges are colored. Those skilled in the art will appreciate that the, In some embodiments, the user may control the color as well as what the color (and/or stroke color, text, texture, shape, coordinates of the nodes on the screen) indicates.

The user may also drag and drop objects of the interactive visualization 900. In various embodiments, the user may reorient structures of nodes and edges by dragging one or more nodes to another portion of the interactive visualization (e.g., a window). In one example, the user may select node 902, hold node 902, and drag the node across the window. The node 902 will follow the user's cursor, dragging the structure of edges and/or nodes either directly or indirectly connected to the node 902. In some embodiments, the interactive visualization 900 may depict multiple unconnected structures. Each structure may include nodes, however, none of the nodes of either structure are connected to each other. If the user selects and drags a node of the first structure, only the first structure will be reoriented with respect to the user action. The other structure will remain unchanged. The user may wish to reorient the structure in order to view nodes, select nodes, and/or better understand the relationships of the underlying data.

In one example, a user may drag a node to reorient the interactive visualization (e.g., reorient the structure of nodes and edges). While the user selects and/or drags the node, the nodes of the structure associated with the selected node may move apart from each other in order to provide greater visibility. Once the user lets go (e.g., deselects or drops the node that was dragged), the nodes of the structure may continue to move apart from each other.

In various embodiments, once the visualization module 322 generates the interactive display, the depicted structures may move by spreading out the nodes from each other. In one example, the nodes spread from each other slowly allowing the user to view nodes distinguish from each other as well as the edges. In some embodiments, the visualization module 322 optimizes the spread of the nodes for the user's view. In one example, the structure(s) stop moving once an optimal view has been reached.

Those skilled in the art will appreciate that the interactive visualization 900 may respond to gestures (e.g., multitouch), stylus, or other interactions allowing the user to reorient nodes and edges and/or interacting with the underlying data.

The interactive visualization 900 may also respond to user actions such as when the user drags, clicks, or hovers a mouse cursor over a node. In some embodiments, when the user selects a node or edge, node information or edge information may be displayed. In one example, when a node is selected (e.g., clicked on by a user with a mouse or a mouse cursor hovers over the node), a node information box 908 may appear that indicates information regarding the selected node. In this example, the node information box 908 indicates an ID, box ID, number of elements (e.g., data points associated with the node), and density of the data associated with the node.

The user may also select multiple nodes and/or edges by clicking separate on each object, or drawing a shape (such as a box) around the desired objects. Once the objects are selected, a selection information box 912 may display some information regarding the selection. For example, selection information box 912 indicates the number of nodes selected and the total points (e.g., data points or elements) of the selected nodes.

The interactive visualization 900 may also allow a user to further interact with the display. Color option 914 allows the user to display different information based on color of the objects. Color option 914 in FIG. 9 is set to filter_Density, however, other filters may be chosen and the objects re-colored based on the selection. Those skilled in the art will appreciate that the objects may be colored based on any filter, property of data, or characterization. When a new option is chosen in the color option 914, the information and/or colors depicted in the color bar 910 may be updated to reflect the change.

Layout checkbox 914 may allow the user to anchor the interactive visualization 900. In one example, the layout checkbox 914 is checked indicating that the interactive visualization 900 is anchored. As a result, the user will not be able to select and drag the node and/or related structure. Although other functions may still be available, the layout checkbox 914 may help the user keep from accidentally moving and/or reorienting nodes, edges, and/or related structures. Those skilled in the art will appreciate that the layout checkbox 914 may indicate that the interactive visualization 900 is anchored when the layout checkbox 914 is unchecked and that when the layout checkbox 914 is checked the interactive visualization 900 is no longer anchored.

The change parameters button 918 may allow a user to change the parameters (e.g., add/remove filters and/or change the resolution of one or more filters). In one example, when the change parameters button 918 is activated, the user may be directed back to the metric and filter selection interface window 600 (see FIG. 6) which allows the user to add or remove filters (or change the metric). The user may then view the filter parameter interface 700 (see FIG. 7) and change parameters (e.g., intervals and overlap) for one or more filters. The analysis module 320 may then re-analyze the data based on the changes and display a new interactive visualization 900 without again having to specify the data sets, filters, etc.

The find ID's button 920 may allow a user to search for data within the interactive visualization 900. In one example, the user may click the find ID's button 920 and receive a window allowing the user to identify data or identify a range of data. Data may be identified by ID or searching for the data based on properties of data and/or metadata. If data is found and selected, the interactive visualization 900 may highlight the nodes associated with the selected data. For example, selecting a single row or collection of rows of a database or spreadsheet may produce a highlighting of nodes whose corresponding partial cluster contains any element of that selection.

In various embodiments, the user may select one or more objects and click on the explain button 922 to receive in-depth information regarding the selection. In some embodiments, when the user selects the explain button 922, the information about the data from which the selection is based may be displayed. The function of the explain button 922 is further discussed with regard to FIG. 10.

In various embodiments, the interactive visualization 900 may allow the user to specify and identify subsets of interest, such as output filtering, to remove clusters or connections which are too small or otherwise uninteresting. Further, the interactive visualization 900 may provide more general coloring and display techniques, including, for example, allowing a user to highlight nodes based on a user-specified predicate, and coloring the nodes based on the intensity of user-specified weighting functions.

The interactive visualization 900 may comprise any number of menu items. The "Selection" menu may allow the following functions:
Select singletons (select nodes which are not connected to other nodes)
Select all (selects all the nodes and edges)
Select all nodes (selects all nodes)
Select all edges
Clear selection (no selection)
Invert Selection (selects the complementary set of nodes or edges)
Select "small" nodes (allows the user to threshold nodes based on how many points they have)
Select leaves (selects all nodes which are connected to long "chains" in the graph)
Remove selected nodes
Show in a table (shows the selected nodes and their associated data in a table)
Save selected nodes (saves the selected data to whatever format the user chooses. This may allow the user to subset the data and create new datasources which may be used for further analysis.)

In one example of the "show in a table" option, information from a selection of nodes may be displayed. The information may be specific to the origin of the data. In various embodiments, elements of a database table may be listed, however, other methods specified by the user may also be included. For example, in the case of microarray data from gene expression data, heat maps may be used to view the results of the selections.

The interactive visualization 900 may comprise any number of menu items. The "Save" menu may allow may allow the user to save the whole output in a variety of different formats such as (but not limited to):
Image files (PNG/JPG/PDF/SVG etc.)
Binary output (The interactive output is saved in the binary format. The user may reopen this file at any time to get this interactive window again)

In some embodiments, graphs may be saved in a format such that the graphs may be used for presentations. This may include simply saving the image as a pdf or png file, but it may also mean saving an executable .xml file, which may permit other users to use the search and save capability to the database on the file without having to recreate the analysis.

In various embodiments, a relationship between a first and a second analysis output/interactive visualization for differing values of the interval length and overlap percentage may be displayed. The formal relationship between the first and second analysis output/interactive visualization may be that when one cover refines the next, there is a map of simplicial complexes from the output of the first to the output of the second. This can be displayed by applying a restricted form of a three-dimensional graph embedding algorithm, in which a graph is the union of the graphs for the various parameter values and in which the connections are the connections in the individual graphs as well as connections from one node to its image in the following graph. The constituent graphs may be placed in its own plane in 3D space. In some embodiments, there is a restriction that each constituent graph remain within its associated plane. Each constituent graph may be displayed individually, but a small change of parameter value may result in the visualization of the adjacent constituent graph. In some embodiments, nodes in the initial graph will move to nodes in the next graph, in a readily visualizable way.

FIG. 10 is an exemplary interactive visualization 1000 displaying an explain information window 1002 in some embodiments. In various embodiments, the user may select a plurality of nodes and click on the explain button. When the explain button is clicked, the explain information window 1002 may be generated. The explain information window 1002 may identify the data associated with the selected object(s) as well as information (e.g., statistical information) associated with the data.

In some embodiments, the explain button allows the user to get a sense for which fields within the selected data fields are responsible for "similarity" of data in the selected nodes and the differentiating characteristics. There can be many ways of scoring the data fields. The explain information window 1002 (i.e., the scoring window in FIG. 10) is shown along with the selected nodes. The highest scoring fields may distinguish variables with respect to the rest of the data.

In one example, the explain information window 1002 indicates that data from fields day0-day6 has been selected. The minimum value of the data in all of the fields is 0. The explain information window 1002 also indicates the maximum values. For example, the maximum value of all of the data associated with the day0 field across all of the points of the selected nodes is 0.353. The average (i.e., mean) of all of the data associated with the day0 field across all of the points of the selected nodes is 0.031. The score may be a relative (e.g., normalized) value indicating the relative function of the filter; here, the score may indicate the relative density of the data associated with the day0 field across all of the points of the selected nodes. Those skilled in the art will appreciate that any information regarding the data and/or selected nodes may appear in the explain information window 1002.

Those skilled in the art will appreciate that the data and the interactive visualization 1000 may be interacted with in any number of ways. The user may interact with the data directly to see where the graph corresponds to the data, make changes to the analysis and view the changes in the graph, modify the graph and view changes to the data, or perform any kind of interaction.

FIG. 11 is a flowchart 1200 of functionality of the interactive visualization in some embodiments. In step 1202, the visualization engine 322 receives the analysis from the analysis module 320 and graphs nodes as balls and edges as connectors between balls 1202 to create interactive visualization 900 (see FIG. 9).

In step 1204, the visualization engine 322 determines if the user is hovering a mouse cursor (or has selected) a ball (i.e., a node). If the user is hovering a mouse cursor over a ball or selecting a ball, then information is displayed regarding the data associated with the ball. In one example, the visualization engine 322 displays a node information window 908.

If the visualization engine 322 does not determine that the user is hovering a mouse cursor (or has selected) a ball, then the visualization engine 322 determines if the user has selected balls on the graph (e.g., by clicking on a plurality of balls or drawing a box around a plurality of balls). If the user has selected balls on the graph, the visualization engine 322 may highlight the selected balls on the graph in step 1110. The visualization engine 322 may also display information regarding the selection (e.g., by displaying a selection information window 912). The user may also click on the explain button 922 to receive more information associated with the selection (e.g., the visualization engine 322 may display the explain information window 1002).

In step 1112, the user may save the selection. For example, the visualization engine 322 may save the underlying data, selected metric, filters, and/or resolution. The user may then access the saved information and create a new structure in another interactive visualization 900 thereby allowing the user to focus attention on a subset of the data.

If the visualization engine 322 does not determine that the user has selected balls on the graph, the visualization engine 322 may determine if the user selects and drags a ball on the graph in step 1114. If the user selects and drags a ball on the graph, the visualization engine 322 may reorient the selected balls and any connected edges and balls based on the user's action in step 1116. The user may reorient all or part of the structure at any level of granularity.

Those skilled in the art will appreciate that although FIG. 11 discussed the user hovering over, selecting, and/or dragging a ball, the user may interact with any object in the interactive visualization 900 (e.g., the user may hover over, select, and/or drag an edge). The user may also zoom in or zoom out using the interactive visualization 900 to focus on all or a part of the structure (e.g., one or more balls and/or edges).

Further, although balls are discussed and depicted in FIGS. 9-11, those skilled in the art will appreciate that the nodes may be any shape and appear as any kind of object. Further, although some embodiments described herein discuss an interactive visualization being generated based on the output of algebraic topology, the interactive visualization may be generated based on any kind of analysis and is not limited.

For years, researchers have been collecting huge amounts of data on breast cancer, yet we are still battling the disease. Complexity, rather than quantity, is one of the fundamental issues in extracting knowledge from data. A topological data exploration and visualization platform may assist the analysis and assessment of complex data. In various embodiments, a predictive and visual cancer map generated by the topological data exploration and visualization platform may assist physicians to determine treatment options.

In one example, a breast cancer map visualization may be generated based on the large amount of available information already generated by many researchers. Physicians may send biopsy data directly to a cloud-based server which may localize a new patient's data within the breast cancer map visualization. The breast cancer map visualization may be annotated (e.g., labeled) such that the physician may view outcomes of patients with similar profiles as well as different kinds of statistical information such as survival probabilities. Each new data point from a patient may be incorporated into the breast cancer map visualization to improve accuracy of the breast cancer map visualization over time.

Although the following examples are largely focused on cancer map visualizations, those skilled in the art will appreciate that at least some of the embodiments described herein may apply to any biological condition and not be limited to cancer and/or disease. For example, some embodiments, may apply to different industries.

Figure 12:
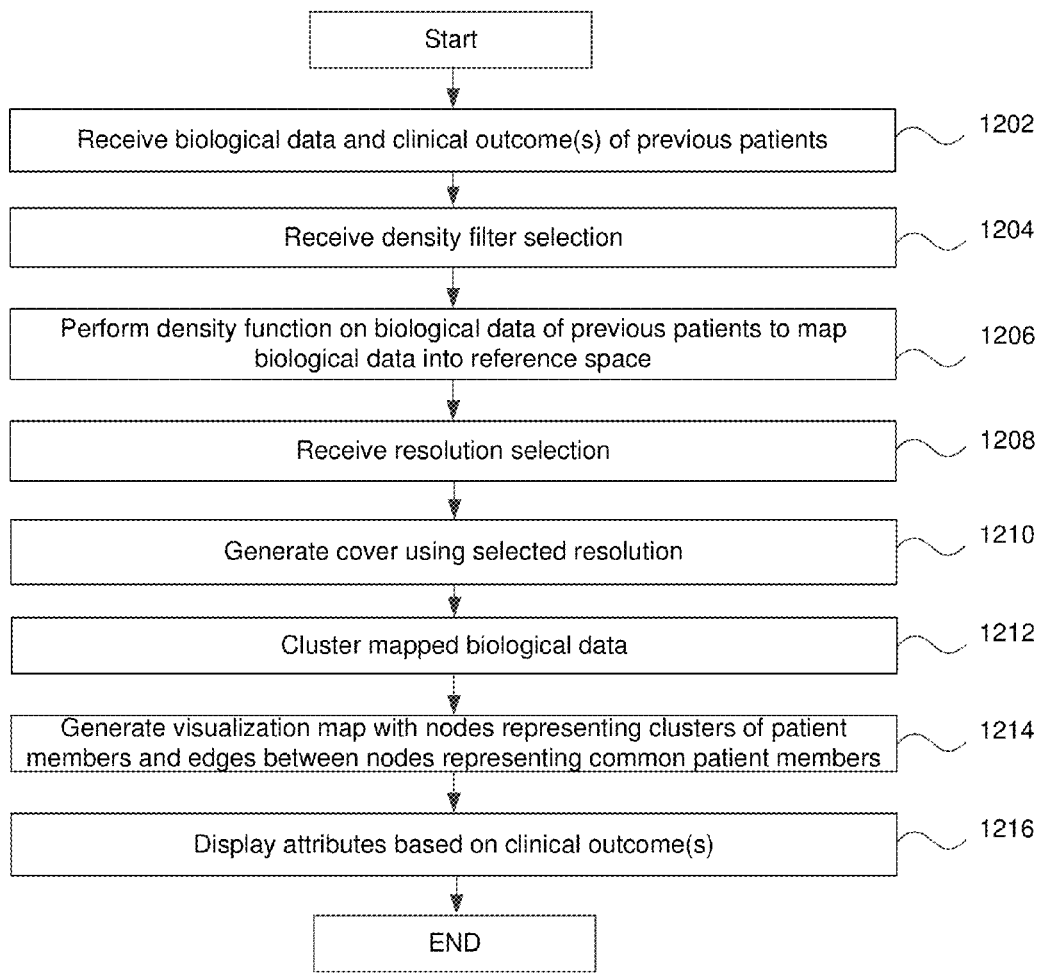
FIG. 12 is a flowchart of for generating a cancer map visualization utilizing biological data of a plurality of patients in some embodiments.

FIG. 12 is a flowchart for generating a cancer map visualization utilizing biological data of a plurality of patients in some embodiments. In various embodiments, the processing of data and user-specified options is motivated by techniques from topology and, in some embodiments, algebraic topology. As discussed herein, these techniques may be robust and general. In one example, these techniques apply to almost any kind of data for which some qualitative idea of "closeness" or "similarity" exists. Those skilled in the art will appreciate that the implementation of techniques described herein may apply to any level of generality.

In various embodiments, a cancer map visualization is generated using genomic data linked to clinical outcomes (i.e., medical characteristics) which may be used by physicians during diagnosis and/or treatment. Initially, publicly available data sets may be integrated to construct the topological map visualizations of patients (e.g., breast cancer patients). Those skilled in the art will appreciate that any private, public, or combination of private and public data sets may be integrated to construct the topological map visualizations. A map visualization may be based on biological data such as, but not limited to, gene expression, sequencing, and copy number variation. As such, the map visualization may comprise many patients with many different types of collected data. Unlike traditional methods of analysis where distinct studies of breast cancer appear as separate entities, the map visualization may fuse disparate data sets while utilizing many datasets and data types.

In various embodiments, a new patient may be localized on the map visualization. With the map visualization for subtypes of a particular disease and a new patient diagnosed with the disease, point(s) may be located among the data points used in computing the map visualization (e.g., nearest neighbor) which is closest to the new patient point. The new patient may be labeled with nodes in the map visualization containing the closest neighbor. These nodes may be highlighted to give a physician the location of the new patient among the patients in the reference data set. The highlighted nodes may also give the physician the location of the new patient relative to annotated disease subtypes.

The visualization map may be interactive and/or searchable in real-time thereby potentially enabling extended analysis and providing speedy insight into treatment.

In step 1202, biological data and clinical outcomes of previous patients may be received. The clinical outcomes may be medical characteristics. Biological data is any data that may represent a condition (e.g., a medical condition) of a person. Biological data may include any health related, medical, physical, physiological, pharmaceutical data associated with one or more patients. In one example, biological data may include measurements of gene expressions for any number of genes. In another example, biological data may include sequencing information (e.g., RNA sequencing).

In various embodiments, biological data for a plurality of patients may be publicly available. For example, various medical health facilities and/or public entities may provide gene expression data for a variety of patients. In addition to the biological data, information regarding any number of clinical outcomes, treatments, therapies, diagnoses and/or prognoses may also be provided. Those skilled in the art will appreciate that any kind of information may be provided in addition to the biological data.

The biological data, in one example, may be similar to data S as discussed with regard to step 802 of FIG. 8. The biological data may include ID fields that identify patients and data fields that are related to the biological information (e.g., gene expression measurements).

FIG. 13 is an exemplary data structure 1302 including biological data 1304a-1304y for a number of patients 1308a-1308n that may be used to generate the cancer map visualization in some embodiments. Column 1302 represents different patient identifiers for different patients. The patient identifiers may be any identifier.

At least some biological data may be contained within gene expression measurements 1304a-1304y. In FIG. 13, "y" represents any number. For example, there may be 50,000 or more separate columns for different gene expressions related to a single patient or related to one or more samples from a patient. Those skilled in the art will appreciate that column 1304a may represent a gene expression measurement for each patient (if any for some patients) associated with the patient identifiers in column 1302. The column 1304b may represent a gene expression measurement of one or more genes that are different than that of column 1304a. As discussed, there may be any number of columns representing different gene expression measurements.

Column 1306 may include any number of clinical outcomes, prognoses, diagnoses, reactions, treatments, and/or any other information associated with each patient. All or some of the information contained in column 1306 may be displayed (e.g., by a label or an annotation that is displayed on the visualization or available to the user of the visualization via clicking) on or for the visualization.

Rows 1308a-1308n each contains biological data associated with the patient identifier of the row. For example, gene expressions in row 1308a are associated with patient identifier P1. As similarly discussed with regard to "y" herein, "n" represents any number. For example, there may be 100,000 or more separate rows for different patients.

Those skilled in the art will appreciate that there may be any number of data structures that contain any amount of biological data for any number of patients. The data structure(s) may be utilized to generate any number of map visualizations.

In step 1204, the analysis server may receive a filter selection. In some embodiments, the filter selection is a density estimation function. Those skilled in the art will appreciate that the filter selection may include a selection of one or more functions to generate a reference space.

In step 1206, the analysis server performs the selected filter(s) on the biological data of the previous patients to map the biological data into a reference space. In one example, a density estimation function, which is well known in the art, may be performed on the biological data (e.g., data associated with gene expression measurement data 1304a-1304y) to relate each patient identifier to one or more locations in the reference space (e.g., on a real line).

In step 1208, the analysis server may receive a resolution selection. The resolution may be utilized to identify overlapping portions of the reference space (e.g., a cover of the reference space R) in step 1210.

As discussed herein, the cover of R may be a finite collection of open sets (in the metric of R) such that every point in R lies in at least one of these sets. In various examples, R is k-dimensional Euclidean space, where k is the number of filter functions. Those skilled in the art will appreciate that the cover of the reference space R may be controlled by the number of intervals and the overlap identified in the resolution (e.g., see FIG. 7). For example, the more intervals, the finer the resolution in S (e.g., the similarity space of the received biological data)—that is, the fewer points in each S(d), but the more similar (with respect to the filters) these points may be. The greater the overlap, the more times that clusters in S(d) may intersect clusters in S(e)—this means that more "relationships" between points may appear, but, in some embodiments, the greater the overlap, the more likely that accidental relationships may appear.

In step 1212, the analysis server receives a metric to cluster the information of the cover in the reference space to partition S(d). In one example, the metric may be a Pearson Correlation. The clusters may form the groupings (e.g., nodes or balls). Various cluster means may be used including, but not limited to, a single linkage, average linkage, complete linkage, or k-means method.

As discussed herein, in some embodiments, the analysis module 320 may not cluster two points unless filter values are sufficiently "related" (recall that while normally related may mean "close," the cover may impose a much more general relationship on the filter values, such as relating two points s and t if ref(s) and ref(t) are sufficiently close to the same circle in the plane where ref( ) represents one or more filter functions). The output may be a simplicial complex, from which one can extract its 1-skeleton. The nodes of the complex may be partial clusters, (i.e., clusters constructed from subsets of S specified as the preimages of sets in the given covering of the reference space R).

In step 1214, the analysis server may generate the visualization map with nodes representing clusters of patient members and edges between nodes representing common patient members. In one example, the analysis server identifies nodes which are associated with a subset of the partition elements of all of the S(d) for generating an interactive visualization.

As discussed herein, for example, suppose that S={1, 2, 3, 4}, and the cover is $C_1$, $C_2$, $C_3$. Suppose cover $C_1$ contains {1, 4}, $C_2$ contains {1,2}, and $C_3$ contains {1, 2, 3, 4}. If 1 and 2 are close enough to be clustered, and 3 and 4 are, but nothing else, then the clustering for S(1) may be {1}, {4}, and for S(2) it may be {1,2}, and for S(3) it may be {1,2}, {3,4}. So the generated graph has, in this example, at most four nodes, given by the sets {1}, {4}, {1, 2}, and {3, 4} (note that {1, 2} appears in two different clusterings). Of the sets of points that are used, two nodes intersect provided that the associated node sets have a non-empty intersection (although this could easily be modified to allow users to require that the intersection is "large enough" either in absolute or relative terms).

As a result of clustering, member patients of a grouping may share biological similarities (e.g., similarities based on the biological data).

The analysis server may join clusters to identify edges (e.g., connecting lines between nodes). Clusters joined by edges (i.e., interconnections) share one or more member patients. In step 1216, a display may display a visualization map with attributes based on the clinical outcomes contained in the data structures (e.g., see FIG. 13 regarding clinical outcomes). Any labels or annotations may be utilized based on information contained in the data structures. For example, treatments, prognoses, therapies, diagnoses, and the like may be used to label the visualization. In some embodiments, the physician or other user of the map visualization accesses the annotations or labels by interacting with the map visualization.

The resulting cancer map visualization may reveal interactions and relationships that were obscured, untested, and/or previously not recognized.

Figure 14:
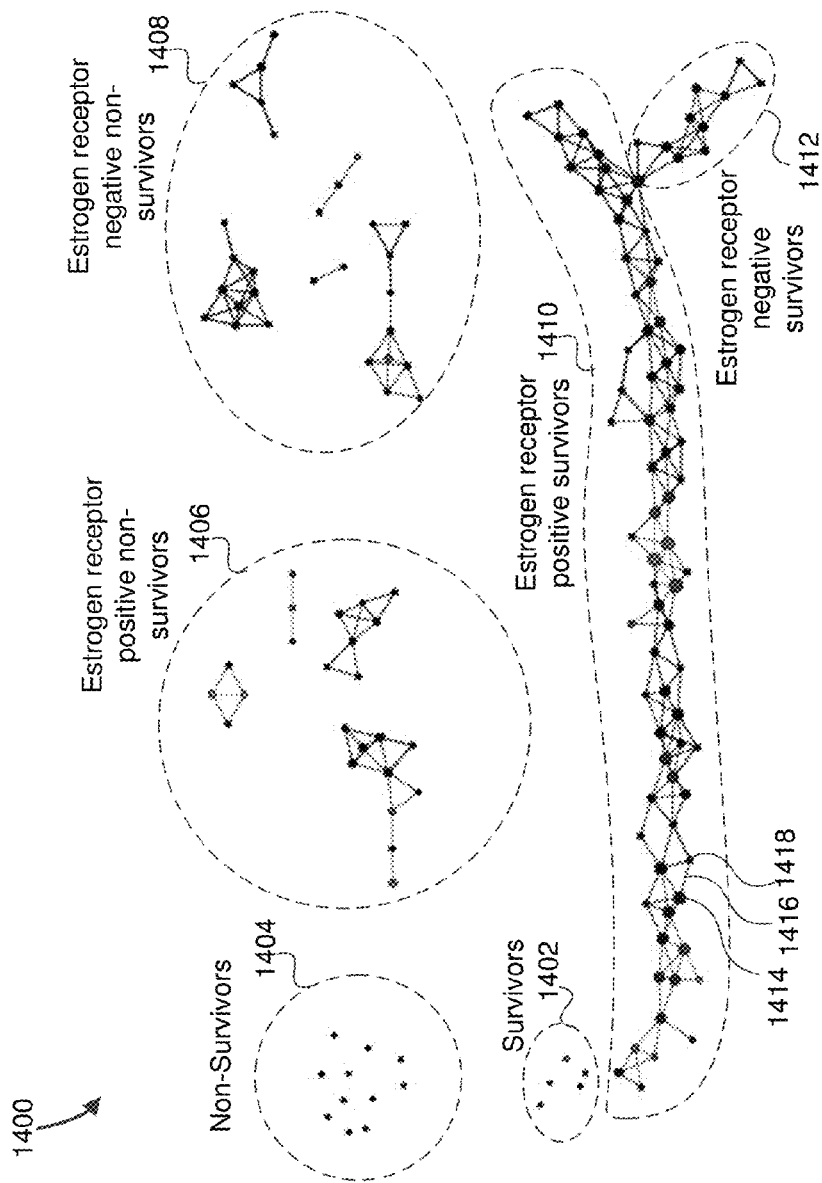
FIG. 14 is an exemplary visualization displaying the cancer map in some embodiments.

FIG. 14 is an exemplary visualization displaying the cancer map visualization 1400 in some embodiments. The cancer map visualization 1400 represents a topological network of cancer patients. The cancer map visualization 1400 may be based on publicly and/or privately available data.

In various embodiments, the cancer map visualization 1400 is created using gene expression profiles of excised tumors. Each node (i.e., ball or grouping displayed in the map visualization 1400) contains a subset of patients with similar genetic profiles.

As discussed herein, one or more patients (i.e., patient members of each node or grouping) may occur in multiple nodes. A patient may share a similar genetic profile with multiple nodes or multiple groupings. In one example, of 50,000 different gene expressions of the biological data, multiple patients may share a different genetic profiles (e.g., based on different gene expression combinations) with different groupings. When a patient shares a similar genetic profile with different groupings or nodes, the patient may be included within the groupings or nodes.

The cancer map visualization 1400 comprises groupings and interconnections that are associated with different clinical outcomes. All or some of the clinical outcomes may be associated with the biological data that generated the cancer map visualization 1400. The cancer map visualization 1400 includes groupings associated with survivors 1402 and groupings associated with non-survivors 1404. The cancer map visualization 1400 also includes different groupings associated with estrogen receptor positive non-survivors 1406, estrogen receptor negative non-survivors 1408, estrogen receptor positive survivors 1410, and estrogen receptor negative survivors 1412.

In various embodiments, when one or more patients are members of two or more different nodes, the nodes are interconnected by an edge (e.g., a line or interconnection). If there is not an edge between the two nodes, then there are no common member patients between the two nodes. For example, grouping 1414 shares at least one common member patient with grouping 1418. The intersection of the two groupings is represented by edge 1416. As discussed herein, the number of shared member patients of the two groupings may be represented in any number of ways including color of the interconnection, color of the groupings, size of the interconnection, size of the groupings, animations of the interconnection, animations of the groupings, brightness, or the like. In some embodiments, the number and/or identifiers of shared member patients of the two groupings may be available if the user interacts with the groupings 1414 and/or 1418 (e.g., draws a box around the two groupings and the interconnection utilizing an input device such as a mouse).

In various embodiments, a physician, on obtaining some data on a breast tumor, direct the data to an analysis server (e.g., analysis server 208 over a network such as the Internet) which may localize the patient relative to one or more groupings on the cancer map visualization 1400. The context of the cancer map visualization 1400 may enable the physician to assess various possible outcomes (e.g., proximity of representation of new patient to the different associations of clinical outcomes).

Figure 15:
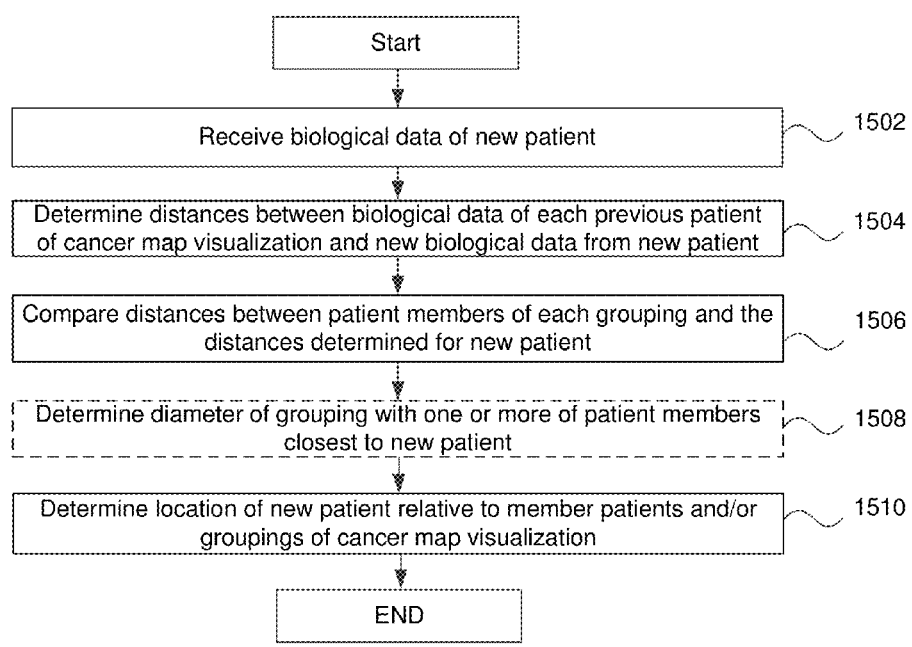
FIG. 15 is a flowchart of for positioning new patient data relative to the cancer map visualization in some embodiments.

FIG. 15 is a flowchart of for positioning new patient data relative to a cancer map visualization in some embodiments. In step 1502, new biological data of a new patient is received. In various embodiments, an input module 314 of an analysis server (e.g., analysis server 208 of FIGS. 1 and 2) may receive biological data of a new patient from a physician or medical facility that performed analysis of one or more samples to generate the biological data. The biological data may be any data that represents a biological data of the new patient including, for example, gene expressions, sequencing information, or the like.

In some embodiments, the analysis server 208 may comprise a new patient distance module and a location engine. In step 1504, the new patient distance module determines distances between the biological data of each patient of the cancer map visualization 1600 and the new biological data from the new patient. For example, the previous biological data that was utilized in the generation of the cancer map visualization 1600 may be stored in mapped data structures. Distances may be determined between the new biological data of the new patient and each of the previous patient's biological data in the mapped data structure.

Those skilled in the art will appreciate that distances may be determined in any number of ways using any number of different metrics or functions. Distances may be determined between the biological data of the previous patients and the new patients. For example, a distance may be determined between a first gene expression measurement of the new patient and each (or a subset) of the first gene expression measurements of the previous patients (e.g., the distance between G1 of the new patient and G1 of each previous patient may be calculated). Distances may be determined between all (or a subset of) other gene expression measurements of the new patient to the gene expression measurements of the previous patients.

In various embodiments, a location of the new patient on the cancer map visualization 1600 may be determined relative to the other member patients utilizing the determined distances.

In step 1506, the new patient distance module may compare distances between the patient members of each grouping to the distances determined for the new patient. The new patient may be located in the grouping of patient members that are closest in distance to the new patient. In some embodiments, the new patient location may be determined to be within a grouping that contains the one or more patient members that are closest to the new patient (even if other members of the grouping have longer distances with the new patient). In some embodiments, this step is optional.

In various embodiments, a representative patient member may be determined for each grouping. For example, some or all of the patient members of a grouping may be averaged or otherwise combined to generate a representative patient member of the grouping (e.g., the distances and/or biological data of the patient members may be averaged or aggregated). Distances may be determined between the new patient biological data and the averaged or combined biological data of one or more representative patient members of one or more groupings. The location engine may determine the location of the new patient based on the distances. In some embodiments, once the closest distance between the new patient and the representative patient member is found, distances may be determined between the new patient and the individual patient members of the grouping associated with the closest representative patient member.

In optional step 1508, a diameter of the grouping with the one or more of the patient members that are closest to the new patient (based on the determined distances) may be determined. In one example, the diameters of the groupings of patient members closest to the new patient are calculated. The diameter of the grouping may be a distance between two patient members who are the farthest from each other when compared to the distances between all patient members of the grouping. If the distance between the new patient and the closest patient member of the grouping is less than the diameter of the grouping, the new patient may be located within the grouping. If the distance between the new patient and the closest patient member of the grouping is greater than the diameter of the grouping, the new patient may be outside the grouping (e.g., a new grouping may be displayed on the cancer map visualization with the new patient as the single patient member of the grouping). If the distance between the new patient and the closest patient member of the grouping is equal to the diameter of the grouping, the new patient may be placed within or outside the grouping.

It will be appreciated that the determination of the diameter of the grouping is not required in determining whether the new patient location is within or outside of a grouping. In various embodiments, a distribution of distances between member patients and between member patients and the new patient is determined. The decision to locate the new patient within or outside of the grouping may be based on the distribution. For example, if there is a gap in the distribution of distances, the new patient may be separated from the grouping (e.g., as a new grouping). In some embodiments, if the gap is greater than a preexisting threshold (e.g., established by the physician, other user, or previously programmed), the new patient may be placed in a new grouping that is placed relative to the grouping of the closest member patients. The process of calculating the distribution of distances of candidate member patients to determine whether there may be two or more groupings may be utilized in generation of the cancer map visualization (e.g., in the process as described with regard to FIG. 12). Those skilled in the art will appreciate that there may be any number of ways to determine whether a new patient should be included within a grouping of other patient members.

In step 1510, the location engine determines the location of the new patient relative to the member patients and/or groupings of the cancer map visualization. The new location may be relative to the determined distances between the new patient and the previous patients. The location of the new patient may be part of a previously existing grouping or may form a new grouping.

In some embodiments, the location of the new patient with regard to the cancer map visualization may be performed locally to the physician. For example, the cancer map visualization 1400 may be provided to the physician (e.g., via digital device). The physician may load the new patient's biological data locally and the distances may be determined locally or via a cloud-based server. The location(s) associated with the new patient may be overlaid on the previously existing cancer map visualization either locally or remotely.

Those skilled in the art will appreciate that, in some embodiments, the previous state of the cancer map visualization (e.g., cancer map visualization 1400) may be retained or otherwise stored and a new cancer map visualization generated utilizing the new patient biological data (e.g., in a method similar to that discussed with regard to FIG. 12). The newly generated map may be compared to the previous state and the differences may be highlighted thereby, in some embodiments, highlighting the location(s) associated with the new patient. In this way, distances may be not be calculated as described with regard to FIG. 15, but rather, the process may be similar to that as previously discussed.

Figure 16:
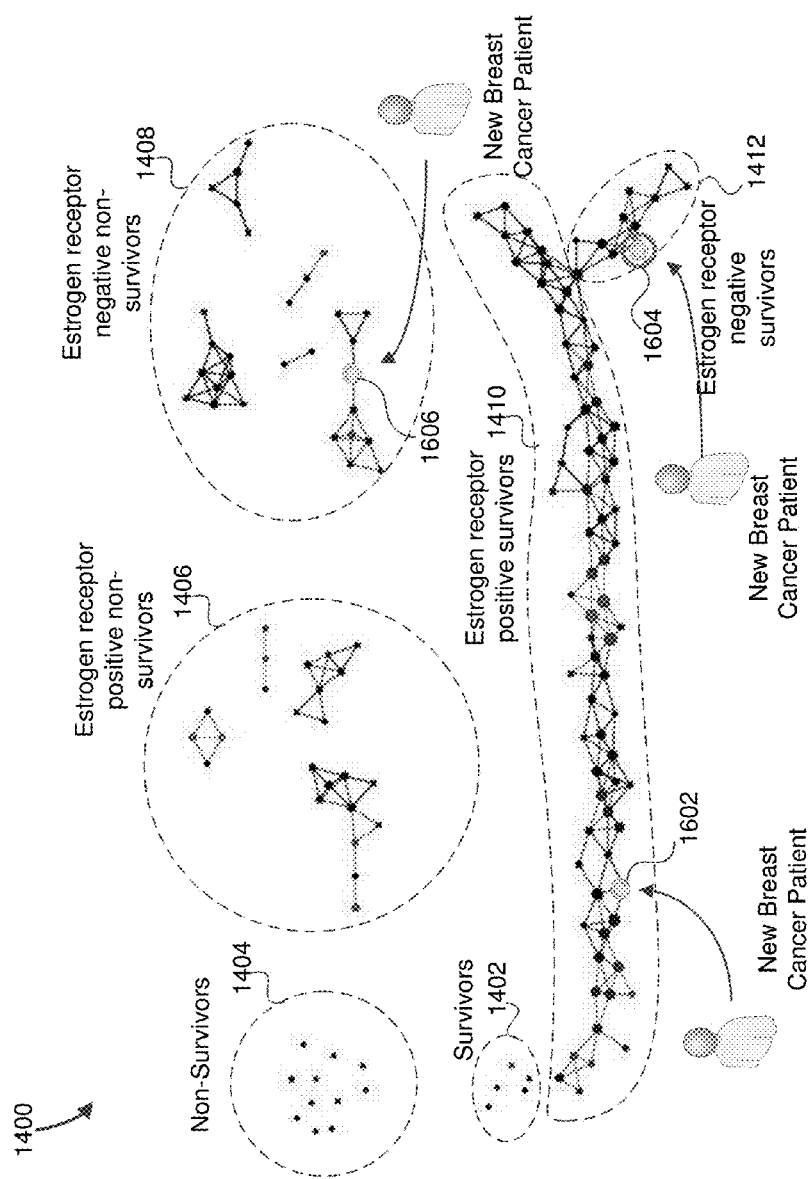
FIG. 16 is an exemplary visualization displaying the cancer map including positions for three new cancer patients in some embodiments.

FIG. 16 is an exemplary visualization displaying the cancer map including positions for three new cancer patients in some embodiments. The cancer map visualization 1400 comprises groupings and interconnections that are associated with different clinical outcomes as discussed with regard to FIG. 14. All or some of the clinical outcomes may be associated with the biological data that generated the cancer map visualization 1400. The cancer map visualization 1400 includes different groupings associated with survivors 1402, groupings associated with non-survivors 1404, estrogen receptor positive non-survivors 1406, estrogen receptor negative non-survivors 1408, estrogen receptor positive survivors 1410, and estrogen receptor negative survivors 1412.

The cancer map visualization 1400 includes three locations for three new breast cancer patients. The breast cancer patient location 1602 is associated with the clinical outcome of estrogen receptor positive survivors. The breast cancer patient location 1604 is associated with the clinical outcome of estrogen receptor negative survivors. Unfortunately, breast cancer patient location 1606 is associated with estrogen receptor negative non-survivors. Based on the locations, a physician may consider different diagnoses, prognoses, treatments, and therapies to maintain or attempt to move the breast cancer patient to a different location utilizing the cancer map visualization 1400.

In some embodiments, the physician may assess the underlying biological data associated with any number of member patients of any number of groupings to better understand the genetic similarities and/or dissimilarities. The physician may utilize the information to make better informed decisions.

The patient location 1604 is highlighted on the cancer map visualization 1400 as active (e.g., selected by the physician). Those skilled in the art will appreciate that the different locations may be of any color, size, brightness, and/or animated to highlight the desired location(s) for the physician. Further, although only one location is identified for three different breast cancer patients, any of the breast cancer patients may have multiple locations indicating different genetic similarities.

Those skilled in the art will appreciate that the cancer map visualization 1400 may be updated with new information at any time. As such, as new patients are added to the cancer map visualization 1400, the new data updates the visualization such that as future patients are placed in the map, the map may already include the updated information. As new information and/or new patient data is added to the cancer map visualization 1400, the cancer map visualization 1400 may improve as a tool to better inform physicians or other medical professionals.

In various embodiments, the cancer map visualization 1400 may track changes in patients over time. For example, updates to a new patient may be visually tracked as changes in are measured in the new patient's biological data. In some embodiments, previous patient data is similarly tracked which may be used to determine similarities of changes based on condition, treatment, and/or therapies, for example. In various embodiments, velocity of change and/or acceleration of change of any number of patients may be tracked over time using or as depicted on the cancer map visualization 1400. Such depictions may assist the treating physician or other personnel related to the treating physician to better understand changes in the patient and provide improved, current, and/or updated diagnoses, prognoses, treatments, and/or therapies.

Figure 17:
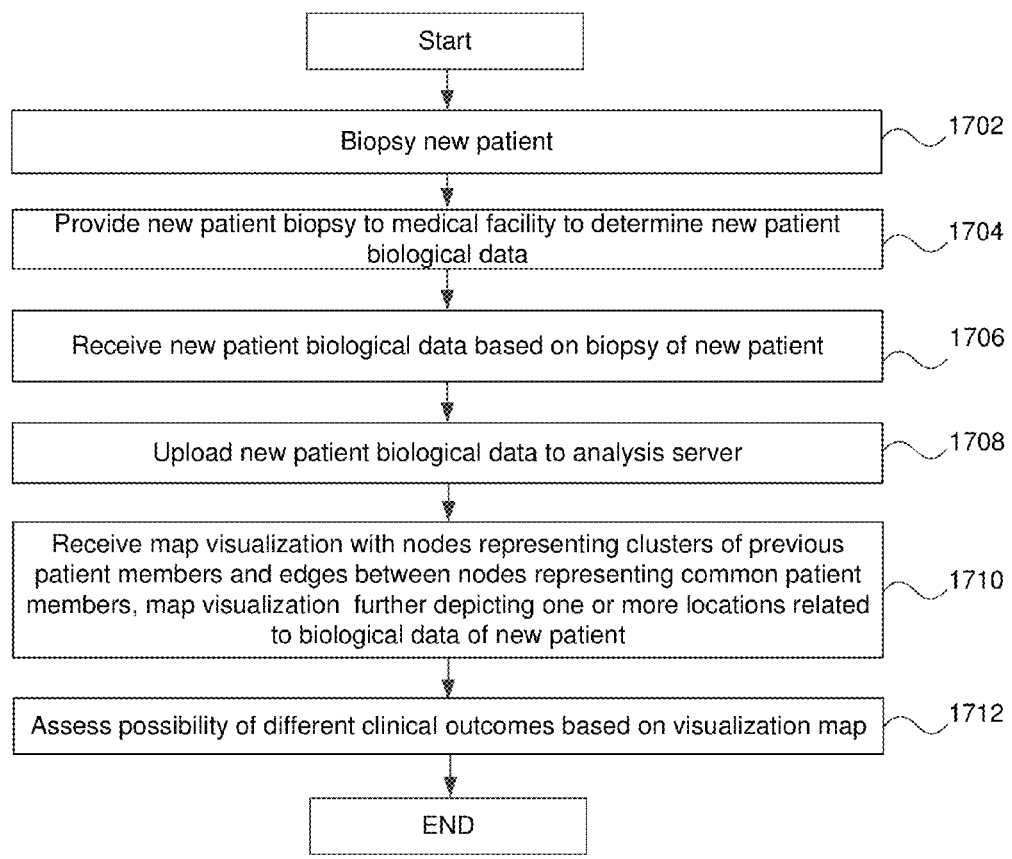
FIG. 17 is a flowchart of utilization the visualization and positioning of new patient data in some embodiments

FIG. 17 is a flowchart of utilization the visualization and positioning of new patient data in some embodiments. In various embodiments, a physician may collect amounts of genomic information from tumors removed from a new patient, input the data (e.g., upload the data to an analysis server), and receive a map visualization with a location of the new patient. The new patient's location within the map may offer the physician new information about the similarities to other patients. In some embodiments, the map visualization may be annotated so that the physician may check the outcomes of previous patients in a given region of the map visualization are distributed and then use the information to assist in decision-making for diagnosis, treatment, prognosis, and/or therapy.

In step 1702, a medical professional or other personnel may remove a sample from a patient. The sample may be of a tumor, blood, or any other biological material. In one example, a medical professional performs a tumor excision. Any number of samples may be taken from a patient.

In step 1704, the sample(s) may be provided to a medical facility to determine new patient biological data. In one example, the medical facility measures genomic data such as gene expression of a number of genes or protein levels.

In step 1706, the medical professional or other entity associated with the medical professional may receive the new patient biological data based on the sample(s) from the new patient. In one example, a physician may receive the new patient biological data. The physician may provide all or some of the new patient biological data to an analysis server over the Internet (e.g., the analysis server may be a cloud-based server). In some embodiments, the analysis server is the analysis server 208 of FIG. 1. In some embodiments, the medical facility that determines the new patient biological data provides the biological data in an electronic format which may be uploaded to the analysis server. In some embodiments, the medical facility that determines the new patient biological data (e.g., the medical facility that measures the genomic data) provide the biological data to the analysis server at the request of the physician or others associated with the physician. Those skilled in the art will appreciate that the biological data may be provided to the analysis server in any number of ways.

The analysis server may be any digital device and may not be limited to a digital device on a network. In some embodiments, the physician may have access to the digital device. For example, the analysis server may be a table, personal computer, local server, or any other digital device.

Once the analysis server receives the biological data of the new patient, the new patient may be localized in the map visualization and the information may be sent back to the physician in step 1708. The visualization may be a map with nodes representing clusters of previous patient members and edges between nodes representing common patient members. The visualization may further depict one or more locations related to the biological data of the new patient.

The map visualization may be provided to the physician or other associated with the physician in real-time. For example, once the biological data associated with the new patient is provided to the analysis server, the analysis server may provide the map visualization back to the physician or other associated with the physician within a reasonably short time (e.g., within seconds or minutes). In some embodiments, the physician may receive the map visualization over any time.

The map visualization may be provided to the physician in any number of ways. For example, the physician may receive the map visualization over any digital device such as, but not limited to, an office computer, Ipad, tablet device, media device, smartphone, e-reader, or laptop.

In step 1710, the physician may assess possible different clinical outcomes based on the map visualization. In one example, the map-aided physician may make decisions on therapy and treatments depending on where the patient lands on the visualization (e.g., survivor or non-survivor). The map visualization may include annotations or labels that identify one or more sets of groupings and interconnections as being associated with one or more clinical outcomes. The physician may assess possible clinical outcomes based on the position(s) on the map associated with the new patient.

As described above, interesting continuous functions on a metric space (e.g., a similarity space) allow the application of systems and methods described herein. In various embodiments, functions may be performed on data within the metric space to project data into the reference space. Having the function(s) to project the data from the metric space to the similarity space (i.e., a lens function) dependent on a small number of coordinates (e.g., counting a number of uses of a small collection of words) is a fairly simple way to achieve continuity in most metrics, and the resulting lenses may be suitable for interpolation. However, such lenses may be of limited use on high-dimensional data, and if the interesting features of the space were captured in those few dimensions, there may be no point keeping the rest of the coordinates.

In practice, lenses which incorporate intrinsic properties of the metric (e.g., the function on the data to generate the metric space), such as density or centrality, are more likely to capture features of the space, absent special knowledge of the particular data set, than functions which depend on a few coordinates. One example method of dimensionality reduction (which is a way to think of a small collection of lenses applied jointly) are variants of "Stochastic Neighbor Embedding" (aka SNE). The underlying intuition in stochastic neighbor embedding is to map the high dimensional space to points in a low-dimensional Euclidean space, typically two or three dimensions, define a potential function on the points which penalizes them for being either closer or farther apart in the embedding than they are in the high-dimensional space, and move points around to minimize the potential. This may be effectively like a graph-layout problem, where a (potentially) high-dimensional space, an arbitrary combinatorial graph, is to be faithfully represented by a two-dimensional picture.

Some example methods amount to computing a global potential and then optimizing the placement by the same optimization techniques used in applications of artificial neural network. These methods produce very nice pictures and the lenses can be remarkably effective with TDA, but they may be computationally expensive. Some embodiments described herein allow for the use of less computationally expensive layout mechanisms and methods.

Figure 18:
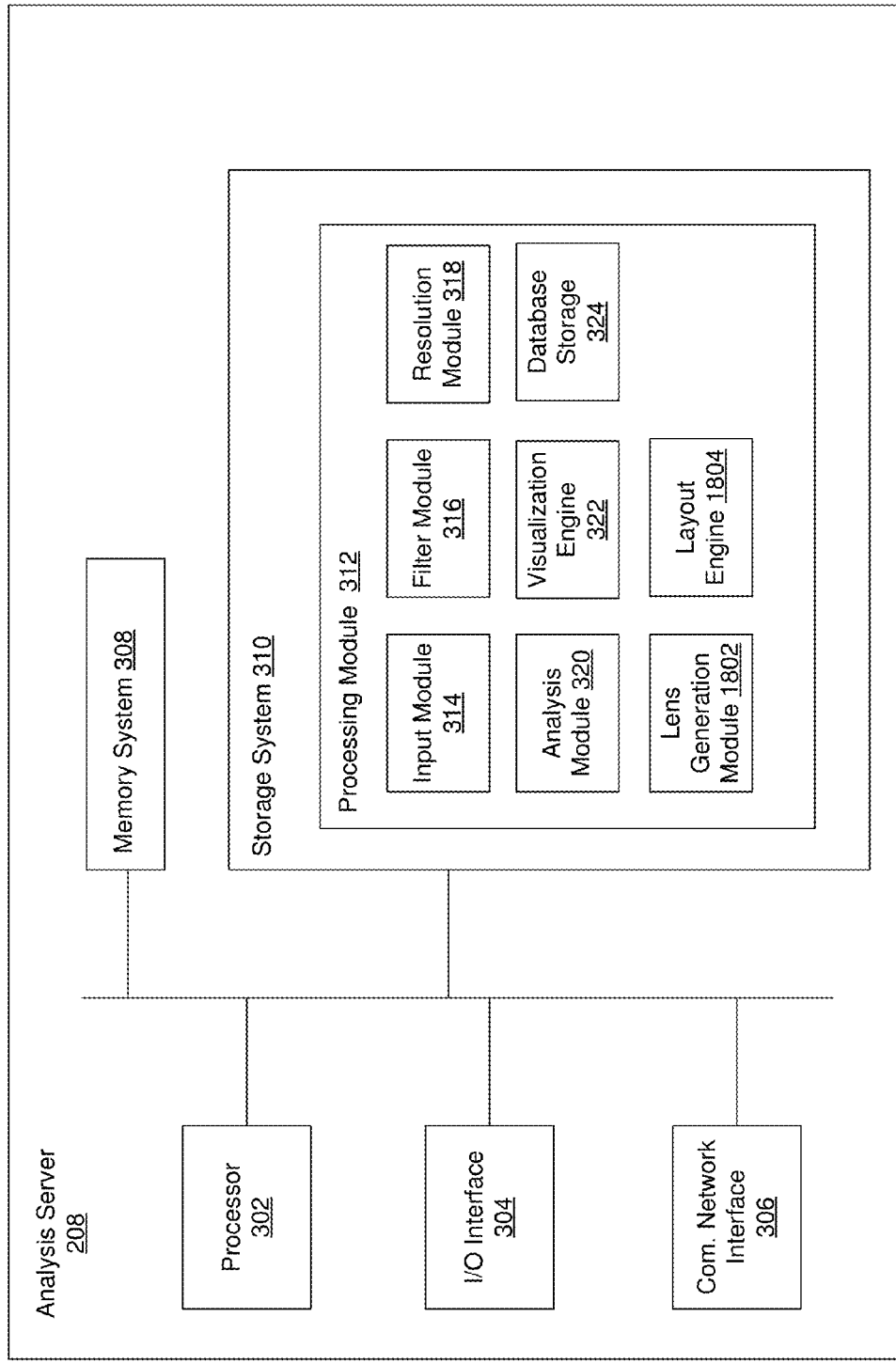
FIG. 18 is a block diagram of an example analysis server with a lens generation module and a graph layout engine.

FIG. 18 is a block diagram of an exemplary analysis server 208 with a lens generation module 1802 and a layout engine 1804. The exemplary analysis server 208 depicted in FIG. 18 may be similar to the exemplary analysis server 208 depicted in FIG. 3. In exemplary embodiments, the analysis server 208 comprises a processor 302, input/output (I/O) interface 304, a communication network interface 306, a memory system 308, and a storage system 310.

The storage system 310 comprises a plurality of modules utilized by some embodiments. In various embodiments, the storage system 310 comprises a processing module 312 which comprises an input module 314, a filter module 316, a resolution module 318, an analysis module 320, a visualization engine 322, a database storage 324, a lens generation module 1802, and a layout engine 1804. Alternative embodiments of the analysis server 208 and/or the storage system 310 may comprise more, less, or functionally equivalent components and modules.

In various embodiments, the input module 314 receive data (e.g., high dimensional data) from any number of digital devices. The analysis server 208 may perform TDA and/or other analytics on the received data. In some embodiments, the input module 314 does not generate or provide a graphical user interface or generate windows to display information or receive user information.

In some embodiments, the input module 314 may be configured to receive commands and preferences from the user device 202a. In various examples, the input module 314 receives selections from the user which will be used to perform the analysis. The output of the analysis may be an interactive visualization.

The input module 314 may provide the user a variety of interface windows allowing the user to select and access a database, choose fields associated with the database, choose a metric, choose one or more filters, and identify resolution parameters for the analysis. In one example, the input module 314 receives a database identifier and accesses a large multi-dimensional database. The input module 314 may scan the database and provide the user with an interface window allowing the user to identify an ID field. An ID field is an identifier for each data point. In one example, the identifier is unique. The same column name may be present in the table from which filters are selected. After the ID field is selected, the input module 314 may then provide the user with another interface window to allow the user to choose one or more data fields from a table of the database.

Although interactive windows may be described herein, those skilled in the art will appreciate that any window, graphical user interface, and/or command line may be used to receive or prompt a user or user device 202a for information.

The filter module 316 may be configured to utilize a similarity, filter, or other function with the received data (e.g., from the input module 314) to generate a finite metric space. In some embodiments, the filter module 316 is configured to receive a similarity, filter, or other function selection by the user. An interface window generated by the filter module 316 (or other module) may allow the user to select a metric function to be used in analysis of the data within the chosen data fields. The filter module 316 may also allow the user to select and/or define one or more filters (e.g., filter functions).

The resolution module 318 may allow the user to select a resolution (e.g., to cluster data), including filter parameters. In one example, the user enters a number of intervals and a percentage overlap for a filter.

The analysis module 320 may perform data analysis based on the database and the information provided by the user. In various embodiments, the analysis module 320 performs an algebraic topological analysis to identify structures and relationships within data and clusters of data. Those skilled in the art will appreciate that the analysis module 320 may use parallel algorithms or use generalizations of various statistical techniques (e.g., generalizing the bootstrap to zig-zag methods) to increase the size of data sets that can be processed. Those skilled in the art will appreciate that the analysis module 320 is not limited to algebraic topological analysis but may perform any analysis.

The visualization engine 322 generates an optional visualization including the output from the analysis module 320. The interactive visualization allows the user to see all or part of the analysis graphically. In some embodiments, the visualization engine 322 generates an interactive visualization. The interactive visualization allows the user to interact with the visualization. For example, the user may select portions of a graph from within the visualization to see and/or interact with the underlying data and/or underlying analysis. The user may then change the parameters of the analysis (e.g., change the metric, filter(s), or resolution(s)) which allows the user to visually identify relationships in the data that may be otherwise undetectable using prior means. The interactive visualization is further described in FIGS. 9-11.

The database storage 324 is configured to store all or part of the database that is being accessed. In some embodiments, the database storage 324 may store saved portions of the database. Further, the database storage 324 may be used to store user preferences, parameters, and analysis output thereby allowing the user to perform many different functions on the database without losing previous work.

The lens generation module 1802 generates at least one function to project information from a metric space to the reference space. In various embodiments, the lens generation module 1802 generates the lens function based on information in the metric space. The lens generation module 1802 may generate the lens function in any number of ways. An exemplary lens generation module 1802 is discussed with regard to FIG. 19.

The layout engine 1804 is configured to layout information in the reference space. An exemplary layout engine 1804 is discussed with regard to FIG. 26.

Those skilled in the art will appreciate that that all or part of the processing module 312 may be at the user device 202a or the database storage server 206. In some embodiments, all or some of the functionality of the processing module 312 may be performed by the user device 202a.

Figure 19:
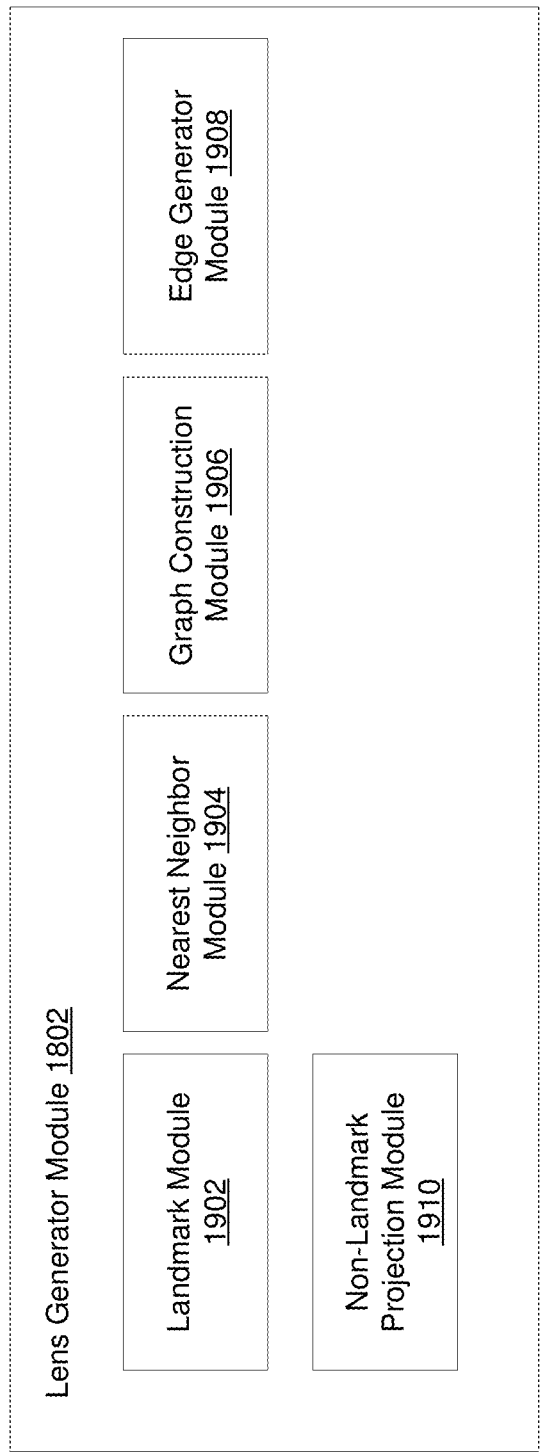
FIG. 19 depicts a lens generator module in some embodiments.

What we describe now is an alternative variant of SNE which may be referred to as Landmarked Stochastic Neighbor Embedding, or LSNE. FIG. 19 depicts a lens generation module 1802 in some embodiments. The lens generation module 1802 may comprise a landmark module 1902, a nearest neighbor module 1904, a graph construction module 1906, an edge generator module 1908, and a non-landmark projection module 1910.

The landmark module 1902 may select a subset of the data. In one example, the landmark module 1902 selects a subset of the data in the finite metric space. The subset of the data may be termed as landmarks of the data. For example, in any finite metric space, the landmark module may choose a set of landmarks L sufficiently large to capture the "features of interest" of the space. In some embodiments, the landmark module 1902 selects a subset of the data in the finite metric space at random. There may be any number of points in the finite metric space selected as landmarks. The number of selected points may be based on the received data, user configuration, and/or any other information. The landmark module 1902 is further discussed with regard to FIG. 29.

We may construct a graph (e.g., a projection into the reference space) on those landmarks and fill in the rest of the values of the space by interpolation. The graph may be the basis or used as a visualization for a user. In some embodiments, the graph is generated in memory and is not a visualization.

The nearest neighbor module 1904 may compute K nearest neighbors (in the landmark set L) for each landmark. The nearest neighbors to a landmark include other landmarks that are closest to the chosen landmark in the finite metric space relative to all or some of the other landmarks in set L.

The size of K may depend, in some embodiments, on an "average small-scale" structure of the space. In one example, K may be between 10 and 50. The nearest neighbor module 1904 may choose K to be any number. In some embodiments, a user (e.g., a data scientist) may configure K to be any number such as, in one example, a fixed value (e.g., 20).

The graph construction module 1906 may construct a series of undirected "cluster graphs" $\Gamma_k$. For example, for every $1 \le k \le K$ by defining an edge between a landmark i and a landmark j if and only if i is one of the k nearest neighbors of j, and conversely. Intuitively, the count of non-trivial components of each $\Gamma_k$ serves as a guide for the choice of which of these graphs to use as a starting point, in practice, starting with $\Gamma_{20}$ may be quite effective.

Having constructed an initial cluster graph, $\Gamma_k$, the edge generator module 1908 may add edges to make a connected graph. In some embodiments, layout code is executed on a single component, since the relationship between the clusters may be almost as important as the clusters themselves. The edge generator module 1908 may compute strengths between the components in $\Gamma_k$, and add edges between components based on those strengths. For example, let the components of $\Gamma_k$ be $C_1, \ldots C_m$. If m is 1, then the edge generator module 1908 may be finished. Otherwise, the edge generator module 1908 may iterate over all pairs of landmarks $a \in C_1$, $b \in C_j$, where $i \ne j$, $1 \le i$, $j \le m$, and for each pair of clusters, remembered the T−1 shortest such edges seen, where T is the number of distinct levels of strength between clusters desired for the final graph. T being larger may mean that there will be more gradations in the grouping of initial clusters, whereas T being 2 may indicate that clusters may be "close" or "far apart." In one example, T=5 to be satisfactory. Note that not every pair of clusters may have T edges between them. For example, a pair of singletons may have only one edge.

The edge generator module 1908 may assign a strength between clusters by summing over all of the K nearest neighbor edges where the strength delta for b being the k-th nearest neighbor of a, with $a \in C_i$ and $b \in C_j$, is $$\frac{1}{k|C_i||C_j|}.$$

In some embodiments, the edge generator module 1908 increments the strength between $C_i$ and $C_j$ by the inverse of the ordinal value of the edge times the product of the sizes of the components. The intuition is that if there are ten points in each component, one hundred edges may be expected, so the strength of each connection may be reduced by proportionally by the product of the sizes. The edge generator module 1908 may then sort the connections between the edges by their strengths, and apply a discretization algorithm to those strengths to assign each connection to one of T categories. The cluster pairs in the strongest category get T−1 edges added between them, the next strongest category get T−2, and so on (the weakest category may get none).

If the graph remains unconnected, the edge generator module 1908 may add shortest edges between pairs of (transitively) unconnected clusters, beginning with the strongest pairs of clusters and working down. In various embodiments, the result is a connected graph.

The layout engine 1804 (see FIG. 18) may lay out the graph in the reference space. An example layout engine 1804 is further discussed with regard to FIGS. 26-28.

The non-landmark projection module 1910 may project non-landmark information from the received information (e.g., from the received data) to the reference space. The process of projection may be done in any number of ways. For example, the non-landmark projection module 1910 may interpolate from the landmarks to find the locations of non-landmark points in the space. An example process of the non-landmark projection module 1910 is discussed with reference to FIG. 20.

Figure 20:
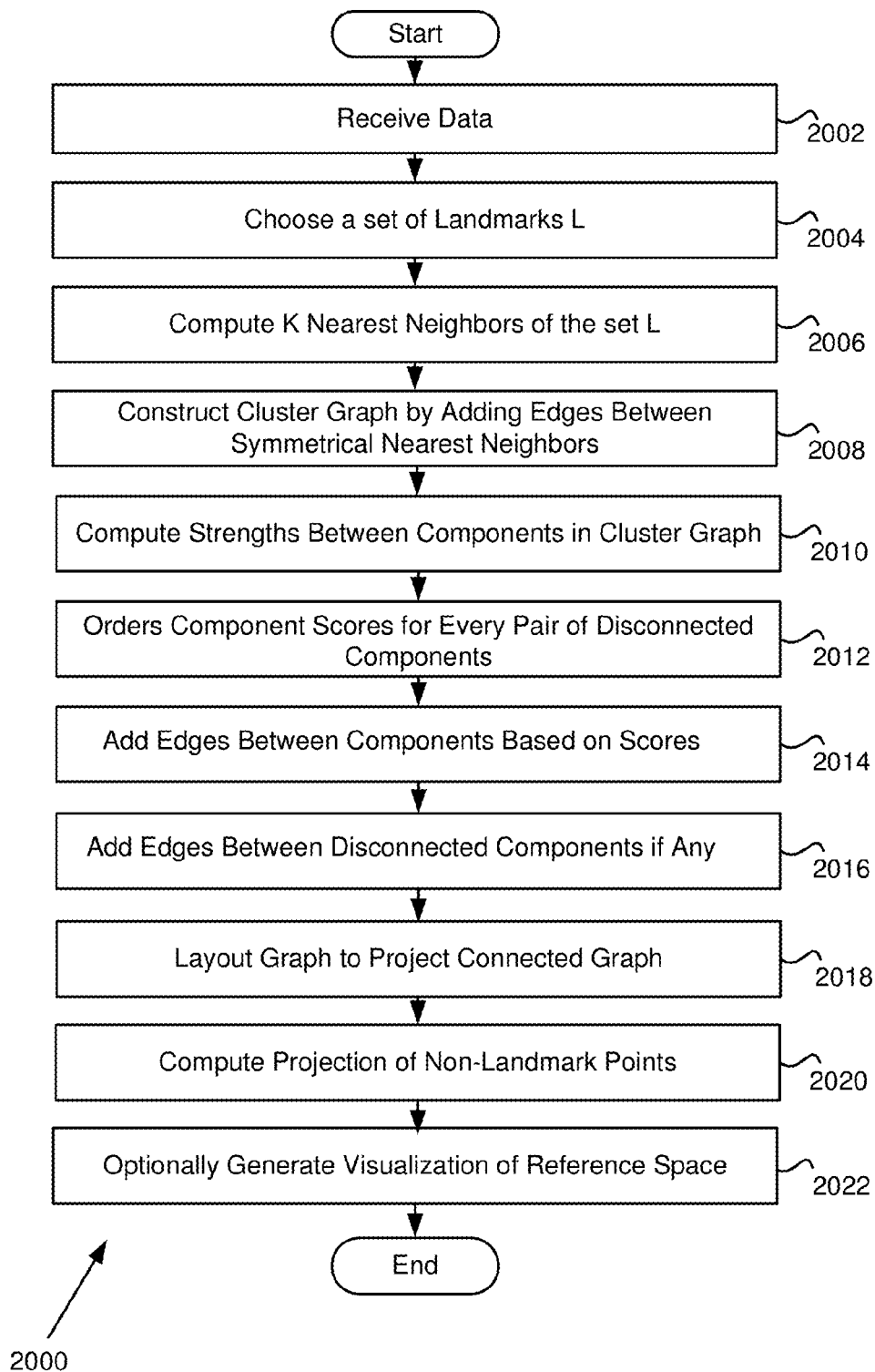
FIG. 20 is a flowchart for lens generation in some embodiments.

FIG. 20 is a flowchart for lens generation in some embodiments. In step 2002, the processing module 312 (e.g., the input module 214) may receive data. The data may be any kind of data, including, for example, gene expressions, text, measurements, or any data. The data may be received from any source or combination of sources. For example, the data may be received from any number of sensors and/or a corpus of data received from any number of digital devices.

In various embodiments, one or more metric functions may be performed on the data to generate a metric space (e.g., a finite metric space). In various embodiments, the filter module 316 applies the one or more metric functions on all or some of the data received from the processing module 312. For example, a metric function may generate measurements of data density, proximity between different data points, similarity between data records, dissimilarity, centrality, and/or any other measurements.

In step 2004, the landmark module 1902 identifies a smaller set of points in the finite metric space as "landmarks."

The landmarks may "characterize" the finite metric space. Intuitively, the landmarks may characterize and/or provide a representation of the larger space. For example, the number of landmarks of the set L may be large enough to capture "features of interest" (e.g., to a data scientist) of the initial received data and/or the finite metric space. Landmarking may be used as a means for increasing scale and performance.

In some embodiments, the landmark module 1902 may select landmarks from the finite metric space to reflect both the average and extreme behavior of the finite metric space. In some examples, the landmark module 1902 may select all or some landmarks from the finite metric space at random or based on any methodology. In some embodiments, additional landmarks may be added that are maximally far from those landmarks. Some examples of the landmark module 1902 are discussed with regard to FIGS. 29-33. The set of landmarks may be represented as the set L.

The landmark module 1902 may select any number of landmarks. In various embodiments, the landmark module 1902 selects a predetermined number of landmarks. The predetermined number of landmarks may be set by a user or determined based on the data (e.g., based on a percentage of points in the finite metric space, density, amount of data received, and/or the like).

In step 2006, the nearest neighbor module 1904 computes the K nearest neighbors of each of the landmarks in the landmark set L. K is, in this example, any whole number. For example, if K is 20, then the nearest neighbor module 1904 identifies the 20 nearest neighbors of each of the landmarks in the landmark set of L. A landmark may be selected and the nearest (e.g., closest) next landmark in the finite metric space to the selected landmark may be characterized as the selected landmark's "nearest neighbor."

Figure 21:
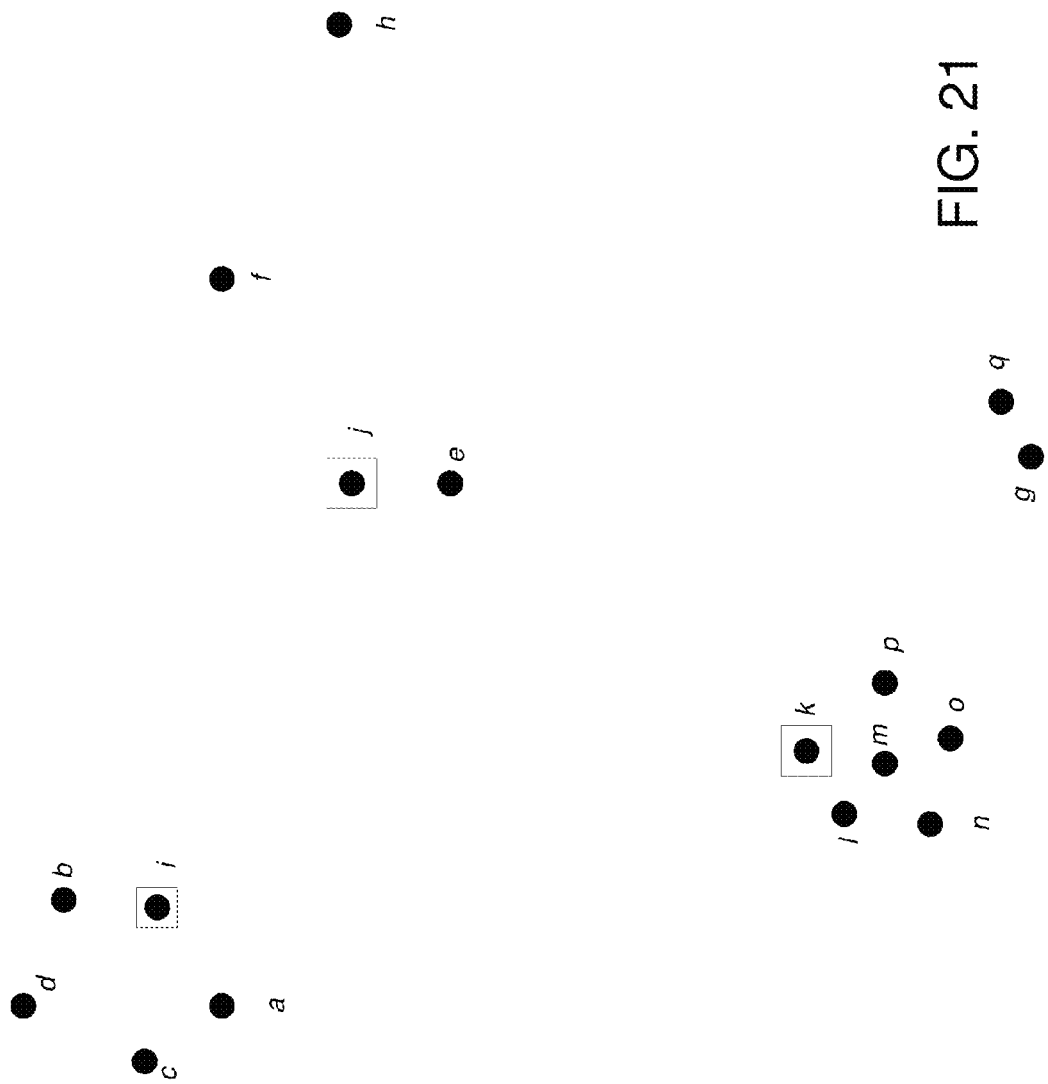
FIG. 21 is an example depiction of landmarks in a finite metric space.

FIG. 21 is an example depiction of landmarks in a finite metric space. The landmarks in FIG. 21 may be a subset of a larger set of landmarks (e.g., the landmarks depicted in FIG. 21 may be a subset of the landmark set L). In this example, the nearest neighbor module 1904 determines the seven (i.e., K=7 in this example) nearest neighbors to each of the landmarks in the landmark set L. In order to determine the nearest neighbors for each landmark in the landmark set L, the nearest neighbor module 1904 may determine the distances between each landmark and all other landmarks in the finite metric space. The nearest neighbor module 1904 may, in some embodiments, store all or some of the distances between each landmark and all other landmarks in the finite metric space for later use.

FIG. 21 depicts the seven nearest neighbors to landmarks i, j, and k which are each depicted in a square box for easy reference. In this example, each landmark may represent one or more measurements (e.g., metrics) by one or more measurement functions performed on any amount of the received data.

The nearest neighbor module 1904 determines that the nearest neighbors to landmark i are {a, b, c, d, j, e, f}. The nearest neighbor module 1904 determines that the nearest neighbors to landmark j are {e, f, i, h, b, k, p}. It will be appreciated that, a first selected landmark may include a nearest neighbor, however, that nearest neighbor may have landmarks that are even closer. For example, the nearest neighbors to landmark k are {l, m, p, n, o, g, q}. Although landmark j includes landmark k as a nearest neighbor (e.g., the closest of K landmarks to j), landmark k has K landmarks that are even closer than j is to k.

It will be appreciated that the nearest neighbor module 1904 may identify a different number of nearest neighbors for different landmarks or different subsets of landmarks.

In step 2008, the graph construction module 1906 generates a "cluster graph" (e.g., an undirected cluster graph) by adding edges (e.g., lines) between landmarks that are symmetrical nearest neighbors of each other. Landmarks are symmetrical nearest neighbors of each other if they are nearest neighbors to each other.

Figure 22:
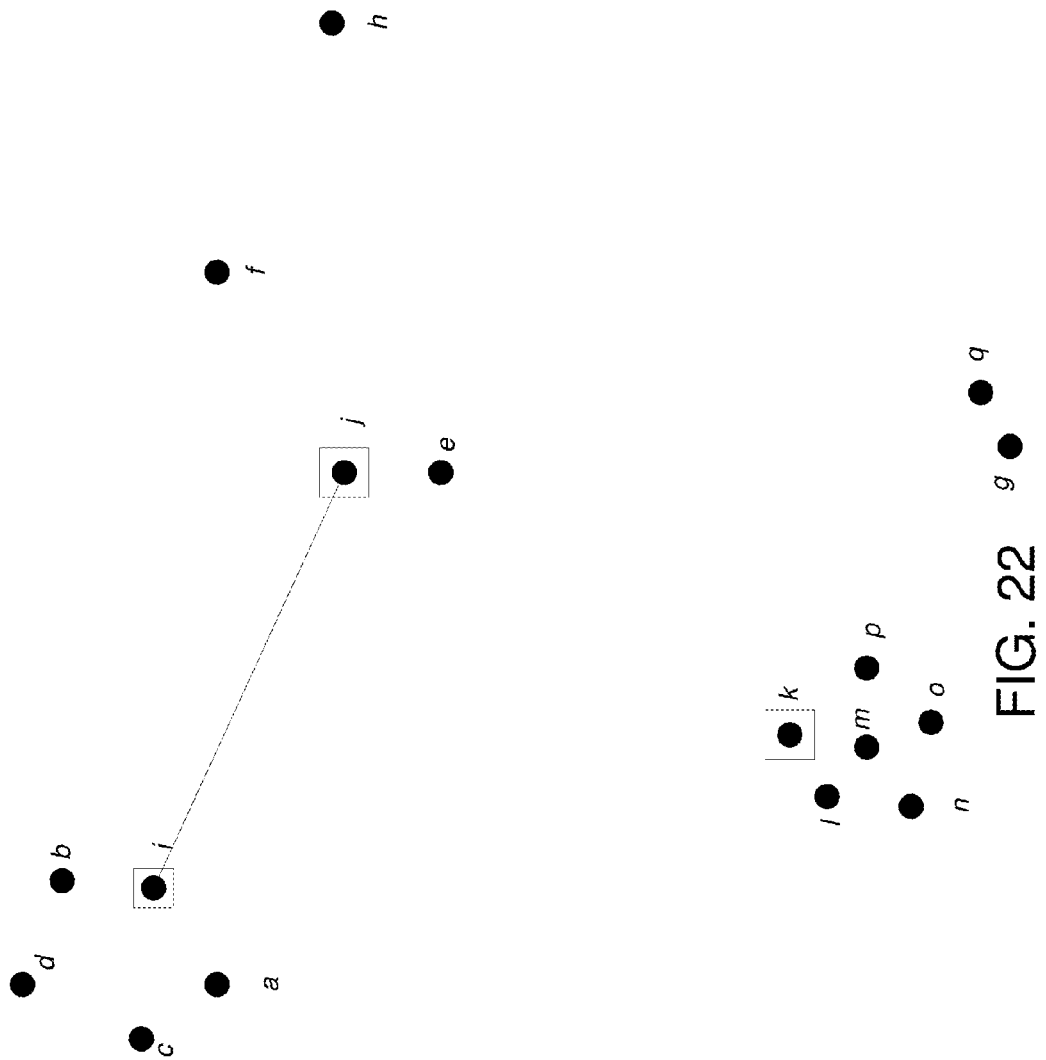
FIG. 22 depicts an edge between landmarks i and j.

For example, landmark i has nearest neighbors {a, b, c, d, j, e, f} and landmark j has nearest neighbors {e, f, i, h, b, k, p}. Since the nearest neighbors to landmark i includes landmark j and the nearest neighbors to landmark j includes landmark i, landmarks i and j are symmetrical nearest neighbors of each other. Since landmarks i and j are symmetrical nearest neighbors of each other, the graph construction module 1906 may add an edge between landmarks i and j. FIG. 22 depicts an edge between landmarks i and j.

Landmarks j and k are not symmetrical nearest neighbors. Landmark j has nearest neighbors {e, f, i, h, b, k, p} and landmark k has nearest neighbors {l, m, p, n, o, g, q}. Although, landmark j has landmark k as a nearest neighbor, landmark k does not have landmark j as a nearest neighbor. As a result, landmark j and landmark k are not symmetrical nearest neighbors to each other and the graph construction module 1906 may not connect landmark j and landmark k with an edge.

It will be appreciated that the graph construction module 1906 may add an edge between landmarks that are symmetrical of a subset of nearest neighbors. A symmetry subset threshold may be a value between 1 (one) and K (i.e., K being the total number of nearest neighbors identified by the nearest neighbor module 1904). In one example, the symmetry subset threshold may be equal to 3. The first three nearest neighbors of landmark i is {a, b, c}. The first three nearest neighbors of landmark j is {e, f, i}. Although landmark i is in the first three nearest neighbors of landmark j, landmark j is not within the first three nearest neighbors of landmark j so the graph construction module 1906 may not add an edge between landmarks i and j.

In some embodiments, adding edges between landmarks that are symmetrical of a subset of total nearest neighbors may allow for scaling and/or efficient computation when compared to adding edges between landmarks that are symmetrical of the total nearest neighbors.

Figure 23:
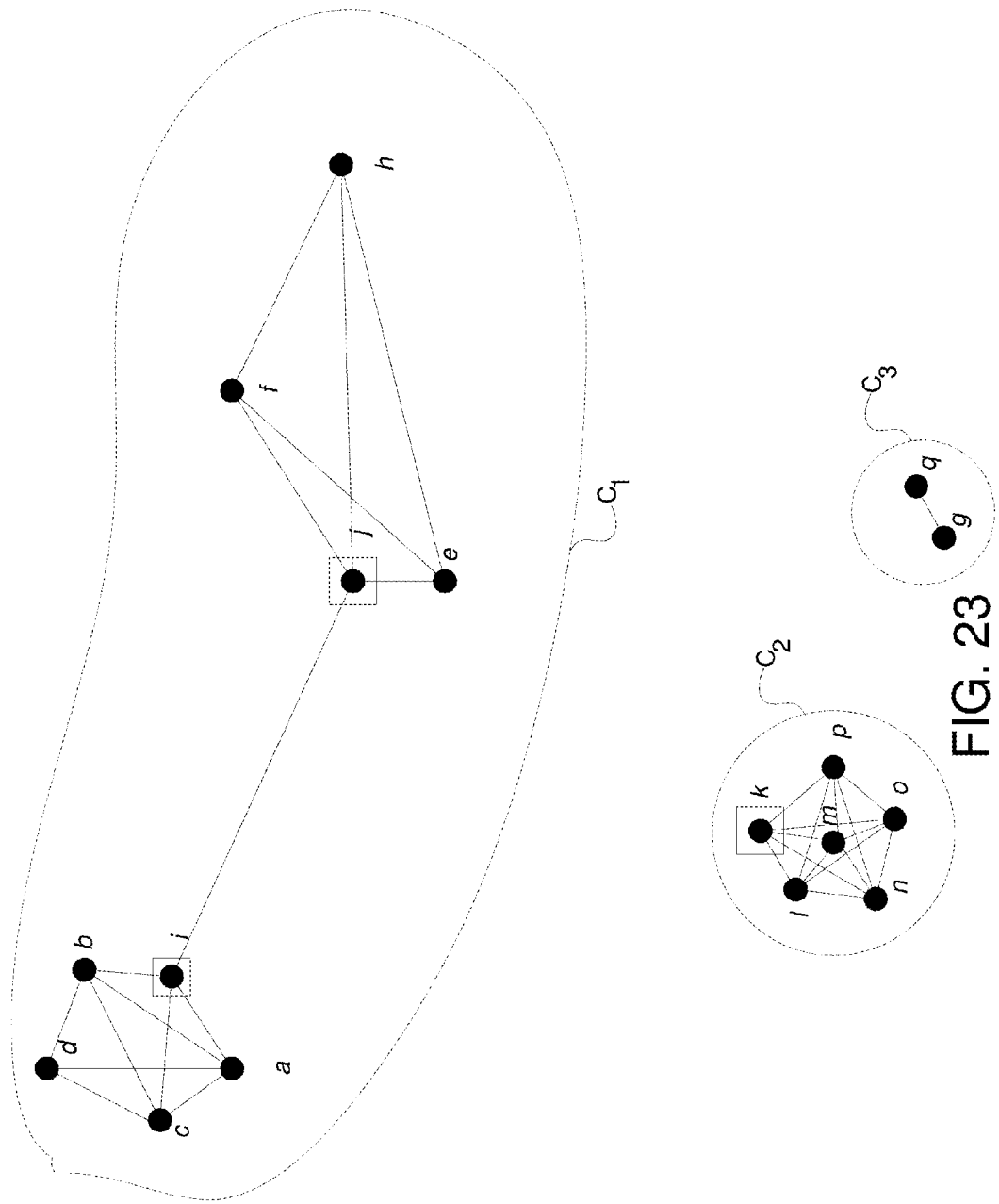
FIG. 23 depicts components $C_1$, $C_2$, and $C_3$ of a disconnected cluster graph.

In steps 2010 and 2012, the edge generator module 1908 adds edges to the cluster graph to create a connected graph where each component of the cluster graph are connected by an edge to at least one other component of the cluster graph. A connected graph exists when there is path from any landmark to any other landmark in the cluster graph. A component of a cluster graph is a set of the landmarks that do not have a path to other landmarks in the cluster graph. For example, a cluster graph with two components $C_1$ and $C_2$ is a cluster graph with two separate subsets of landmarks that do not share any paths between them. FIG. 23 depicts components $C_1$, $C_2$, and $C_3$ of a disconnected cluster graph.

In step 2010, the edge generator module 1908 computes strengths between components in the cluster graph. The edge generator module 1908 may compute strengths between components in a cluster graph in any number of ways. In one example, the edge generator module 1908 may determine a score between each landmark in $C_1$ to its nearest neighbor in $C_2$ (if any). For example, the edge generator module 1908 may determine distances between nearest landmarks in $C_2$ to landmark j. As determined previously, the set of the nearest seven landmarks, in order of distance, to landmark j are {e, f, i, h, b, k, p}.

As discussed previously, the edge generator module 1908 may assign a strength between clusters by summing over all of the K nearest neighbor edges where the strength delta for b being the k-th nearest neighbor of a, with $a \in C_i$ and $b \in C_j$, is $$\frac{1}{(k-th \text{ nearest neighbor})(\text{Size } C_i)(\text{Size } C_j)}.$$

In this example, of the seven nearest landmarks to landmark j, only landmarks k and p are in component $C_2$. In this example, the edge generator module 1908 may assign a strength between landmark j and nearest neighbors of $C_2$ as $$\frac{1}{(6)(9)(6)} + \frac{1}{(7)(9)(6)}.$$

In this example, the edge generator module 1908 will assess the seven nearest neighbors to each landmark in $C_1$ to determine if any of those nearest neighbors are in $C_2$ and score accordingly. Similarly, the edge generator module 1908 will assess the seven nearest neighbors to each landmark in $C_2$ to determine if any of those nearest neighbors are in $C_i$ and score accordingly. Those scores for $C_1$ and $C_2$ will be added together to generate the $C_1C_2$ pair score.

It will be appreciated that not all landmarks will have nearest neighbors in a disconnected component. For example, the nearest seven landmarks, in order of distance, to landmark k are {l, m, p, n, o, g, q}. None of these landmarks are in component $C_1$ and so landmark k will not contribute in assessing the strength of component $C_2$ to relative to component $C_1$.

In various embodiments, the edge generator module 1908 will compute pair scores for every pair of disconnected components of the cluster graph.

In step 2012, the edge generator module 1908 orders the pair scores for every pair of disconnected components (i.e., component pair scores). In one example, the edge generator module 1908 orders the component pair scores in order of highest to lowest scores. It will be appreciated that the edge generator module 1908 may order the component pair scores in any way.

In step 2014, the edge generator module 1908 may add edges between components based on the component scores. In some embodiments, the edge generator module 1908 may assign each component score pair to one of T categories. The component pair score(s) in the strongest category may get T−1 edges added between component pairs. The component pair score(s) in the second strongest category may get T−2 edges added between the component pairs, and so forth. T may be set to any number. For example, a user (e.g., data scientist) may set the value of T.

For example, a T may be set to a value of four and the order of component pair scores in order of highest score to lowest score may be $C_1C_2$, $C_2C_3$, and $C_1C_3$. The edge generator module 1908 may add T−1 edges (three) between components $C_1$ and $C_2$, add T−2 edges (two) between components $C_2$ and $C_3$, and add T−3 edges (one) between components $C_1$ and $C_3$.

The edge generator module 1908 may add edges between two landmarks in two components, respectively, in any number of ways. In various embodiments, the edge generator module 1908 assigns edges between landmarks in different components based on the shortest distances between a pair of landmarks (one landmark in the pair being in different components).

As discussed previously, the nearest neighbor module 1904, in order to identify the nearest neighbors, may determine distances between each landmark and every other landmark in the landmark set L. Distances determined by the nearest neighbor module 1904 may be stored in memory (e.g., RAM and/or a distance landmark matrix). The edge generator module 1908 may identify the shortest distance between two landmarks in two components and add an edge between those landmarks.

Figure 24:
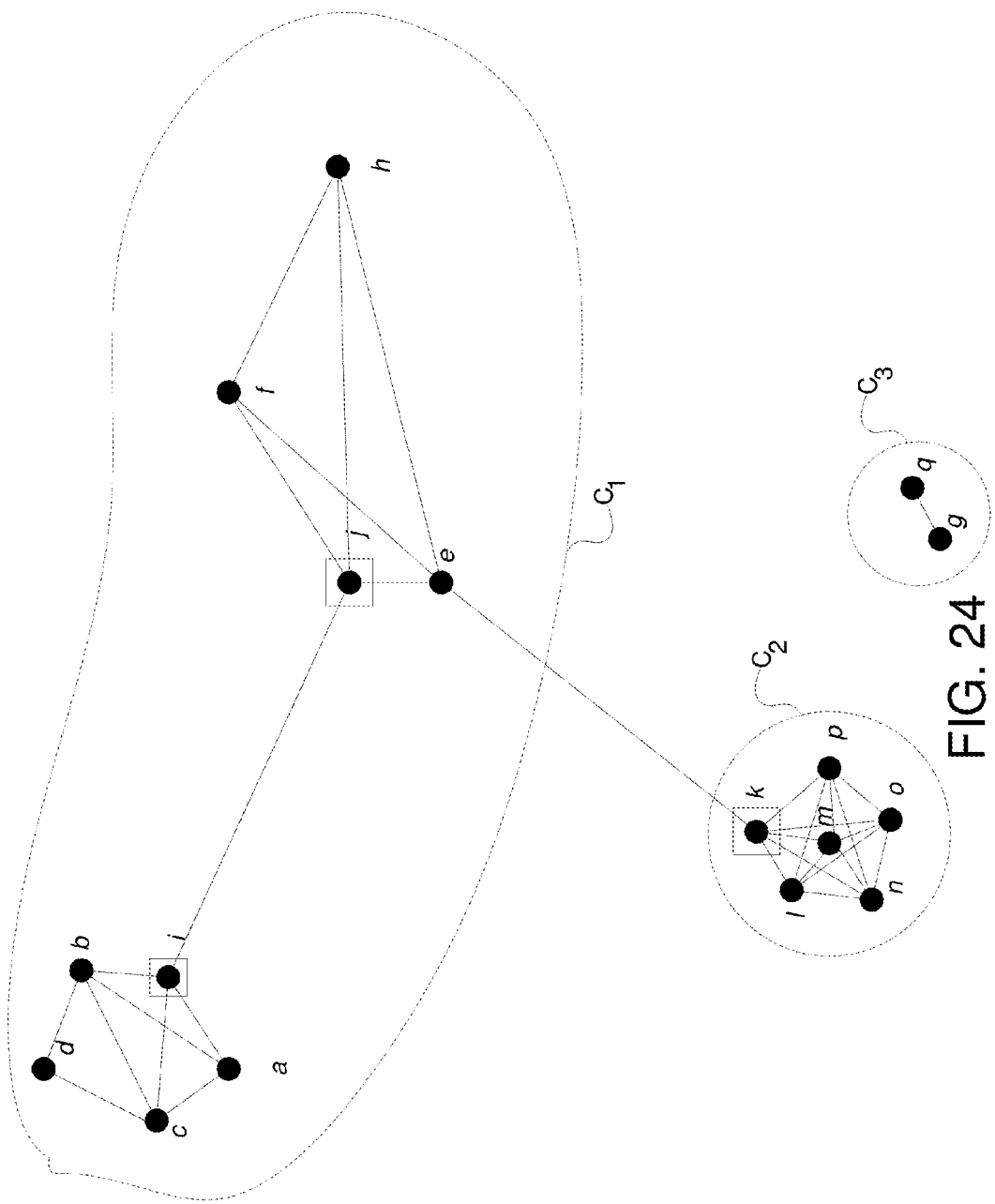
FIG. 24 depicts the cluster graph with an edge added between landmark k in component $C_2$ and landmark e in component $C_1$.

For example, the edge generator module 1908 may determine to add three edges between landmarks of $C_1C_2$ based on the component pair scores. The edge generator module 1908 may identify three pairs of landmarks in $C_1$ and $C_2$ with the shortest distances and add edges (e.g., based on the distances determined by the nearest neighbor module 1904) between each pair of landmarks. For example, as shown in FIG. 24, the closest distance between a landmark in component $C_2$ and a landmark in $C_1$ is between landmark k and landmark e. The edge generator module 1908 may add an edge between landmarks k and e. FIG. 24 depicts the cluster graph with an edge added between landmark k in component $C_2$ and landmark e in component $C_1$.

Similarly, the edge generator module 1908 may, based on the distances determined by the nearest neighbor module 1904, identify landmark l in component $C_2$ and landmark e in component $C_1$ as the next shortest distance and add an edge between the landmarks. The third pair of landmarks of components $C_1$ and $C_2$ with the shortest distance is landmark p and landmark e.

The edge generator module 1908 may determine to add two edges between landmarks of $C_2C_3$ based on the component pair scores. The edge generator module 1908 may identify two pairs of landmarks in $C_2$ and $C_3$ with the shortest distances and add edges (e.g., based on the distances determined by the nearest neighbor module 1904). For example, the edge generator module 1908 may add an edge between landmarks p and q. and another edge between landmarks o and g.

The edge generator module 1908 may determine to add one edge between landmarks of $C_1C_3$ based on the component pair scores. The edge generator module 1908 may identify one pairs of landmarks in $C_1$ and $C_3$ with the shortest distance and add an edge. The edge generator module 1908 may add an edge between landmarks q and e.

Figure 25:
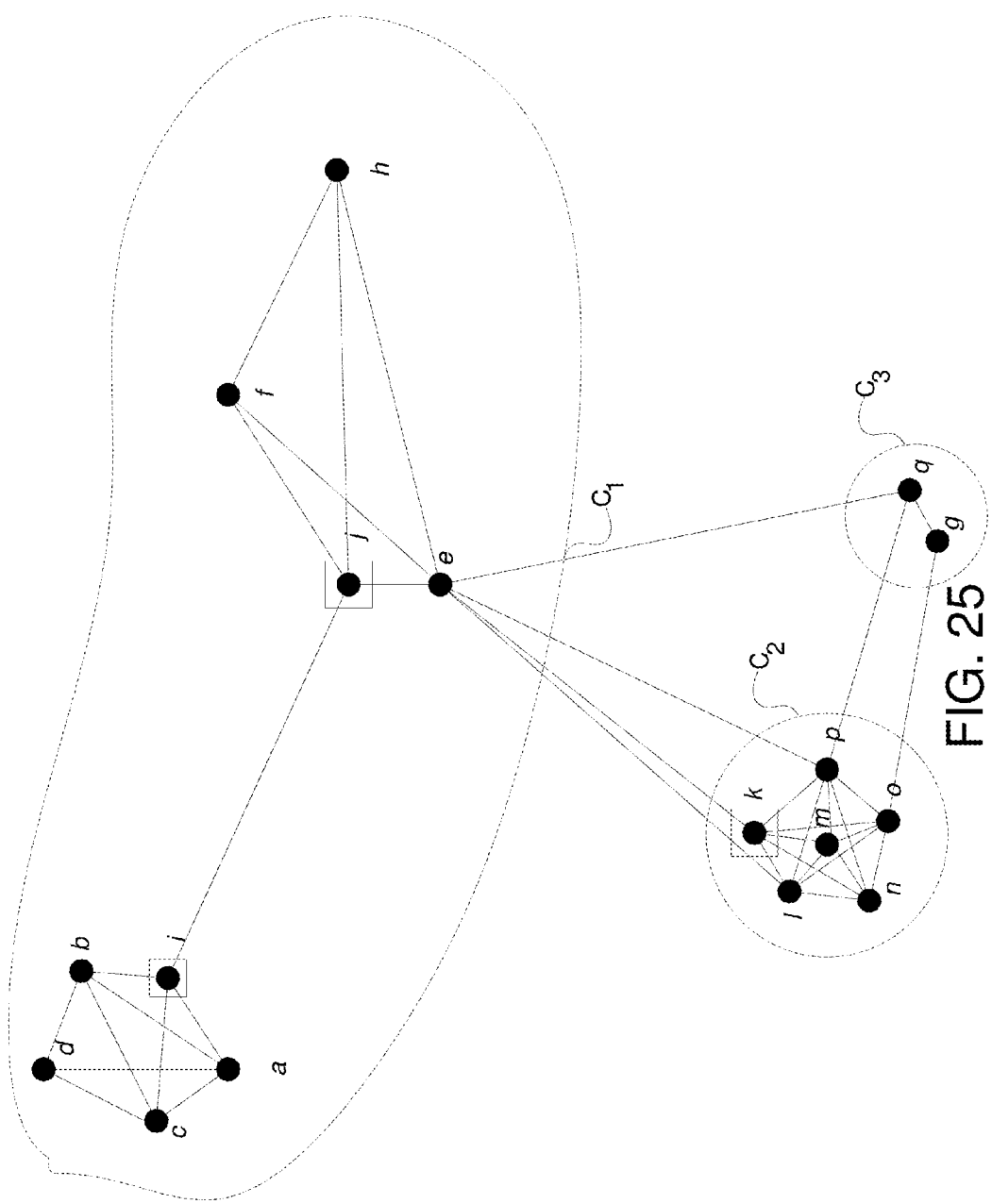
FIG. 25 depicts the cluster graph with edges added between components $C_1$, $C_2$, and $C_3$ in some embodiments.

FIG. 25 depicts the cluster graph with edges added between components $C_1$, $C_2$, and $C_3$ in some embodiments.

In step 2016, edges are added between any remaining disconnected components. In various embodiments, the edge generator module 1908 may identify disconnected components and add an edge between a closest pair of landmarks in the disconnected components. In some embodiments, the edge generator module 1908 may identify disconnected components and add edges between a predetermined number of closest pairs of landmarks in the disconnected components.

In step 2018, the layout engine 1804 maps the graph to a reference space (e.g., a graphical reference space such as a reference space that may be measured in a graphical distance) in some embodiments. For example, the layout module maps the landmarks from the finite metric space to a reference space such as a plane in R2. The description of an example layout engine 1804 and an example layout process is described with respect to FIGS. 26-28.

In step 2020, the non-landmark projection module 1912 computes a projection of at least some of the non-landmark data (e.g., from the received data) to the reference space. For example, the non-landmark projection module 1912 may utilize interpolation to compute the projection.

In some embodiments, the non-landmark projection module 1912 may project the non-landmarks using the GaussianKernel method. The GaussianKernel method defines an interpolation method using a Gaussian kernel, KG(d(x,y),s), where KG(d,s)=Math.exp(−d*d/s*s). The s argument, generally known as sigma, is used by this kernel for interpolation (as well as other methods, such as density estimation).

Note that this kernel is an example of a "radial kernel"—that is, one where the values depend only on the distances between the points. We have a function F(x) whose values we know on landmarks l1, ..., and we wish to compute F(x) in terms of the F(lk), and we do this by taking the sum Wk(x)*F(lk), where the Wk weight functions are given by some combination of radial functions on x and lk. We can ensure continuity if Wk(x)−>delta(k,j) (i.e., Dirac's delta function on k and j) as x−>lj (provided there are no repeated landmarks). Without this limiting condition on the Wk( ) the alternative is to perform linear algebra on the matrix W whose entries are Wk(lj) and then adjust the weight functions to ensure the desired continuity (e.g., generally, find the inverse of the matrix W and use this to adjust the weight functions).

One way to be sure that the Wk( ) have the desired continuity property is to use a collection of functions vk( ) which go to infinity at lk and are nonnegative and finite elsewhere. If we define V( ) to be the sum of the vk( ), and if V( )>0 everywhere, then we can take Wk( ) to be vk( )/V( ). As long as the landmarks are distinct, the vk( ) "blow up"

individually, which means $0<vk(x)N(x)<=1$ and it approaches 1 as $x->lk$, and 0 for x approaching any other landmark. $vk(x)=1/d(x,xk)$, or this to some power $>1$, is what is used by Shepard's Method.

Note that it is not essential the interpolation method be formally continuous, since the discrete spaces and x will not actually "converge."

Here the weight functions we use are $vk(x)=KG(d(x,lk), s(x))$ and we set $vk(x)$ to be ZERO for all but the M nearest landmarks (where $M=20$ seems to work best so far). Otherwise, we take $Wk(x)$ to be $vk(x)/V(x)$, just as above. Note that in this case, vk does not go to infinity, so continuity must be achieved in some other way. Intuitively, we can make $s(x)$ "become like" $d(x,lj)$ as x approaches lj, and this will have the same result—all of the vk( ) for $k!=j$ will become 0, and $vj(x)$ goes to 1 as $x->lj$, which implies $Wk(x)$ acts like the delta function.

However, in practice what we find is that $s(x)$ being the distance to the second nearest landmark gives the smallest RMS (i.e., l2) error. In one example, $s(x)$ is set to the distance to the second nearest landmark.

In some embodiments, vk may be truncated for more distant landmarks. Not all L distances, in some embodiments, need be retained for every point x. Note that this scheme, while only keeping M distances per point, may make use of all the information in the full L×N distance matrix. Also, it will be appreciated that simply making the space bigger (e.g., taking more points in a D-dimensional Euclidean space) will not require increasing M, but it will almost surely require increasing the number of landmarks.

In step 2020, the visualization module 322 optionally generates a visualization of the reference space. It will be appreciated that step 2020 is optional and that all or a portion of the reference space and/or graph of the reference space may be generated in memory (e.g., RAM and/or saved to one or more hard drives).

Figure 35:
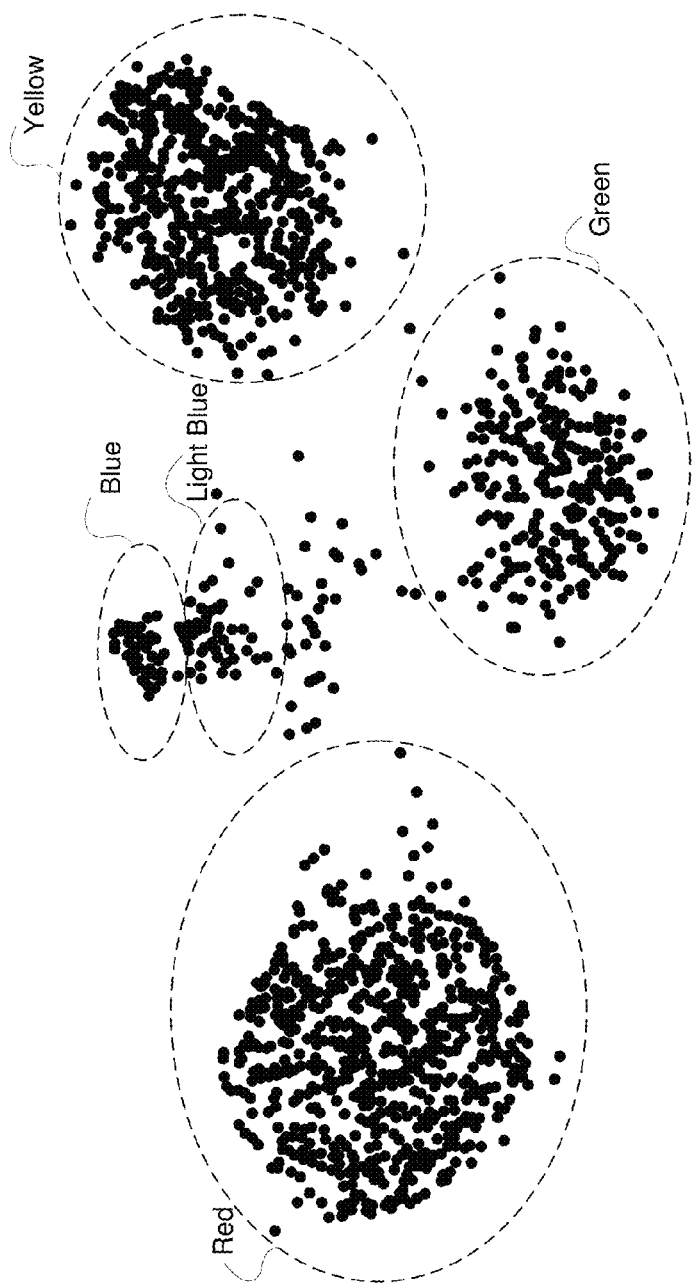
FIG. 35 depicts a visualization of a scatter plot of LSNE lenses.
Figure 36:
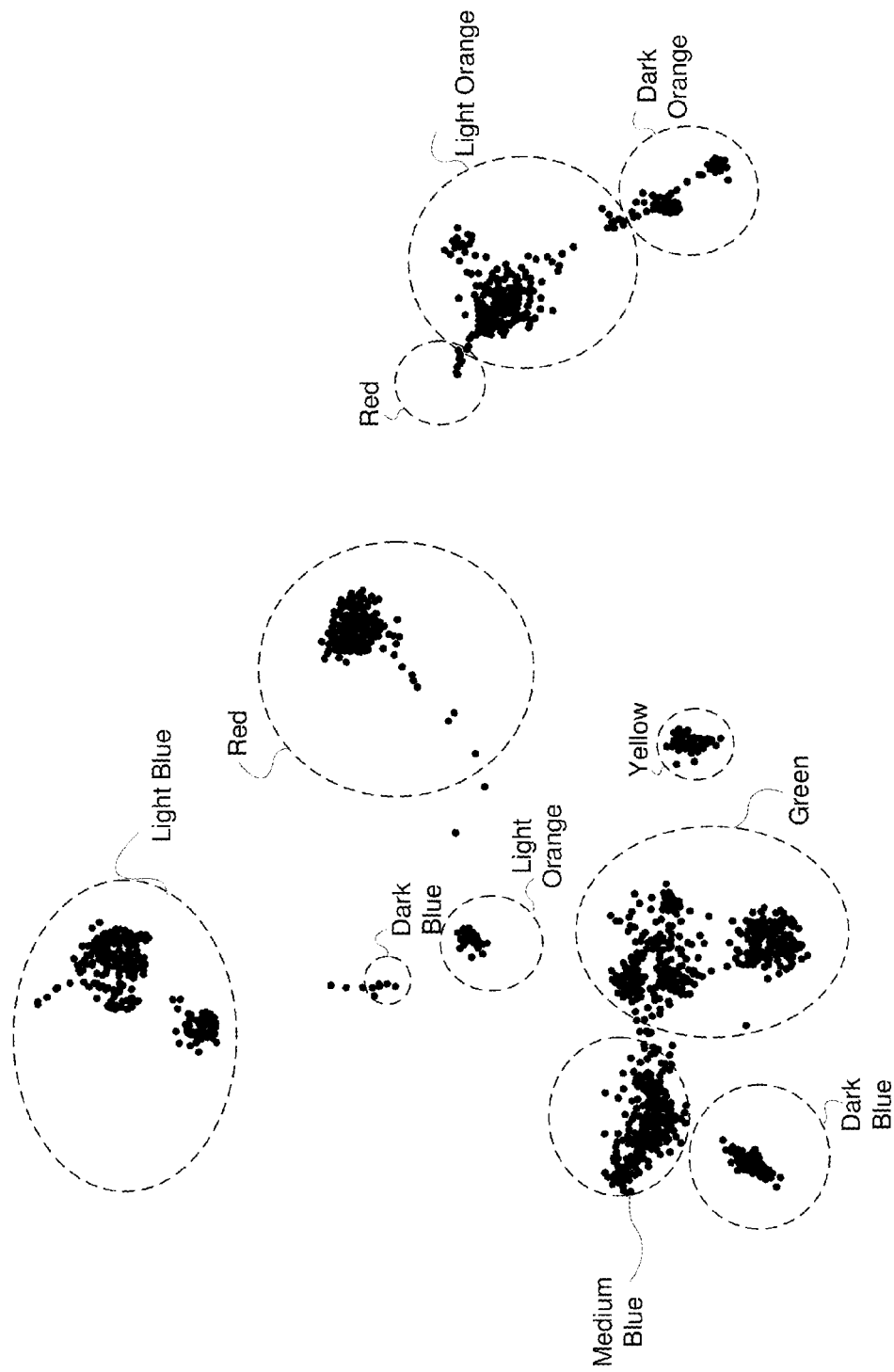
FIG. 36 depicts a visualization of a scatter plot of the LSNE lenses.

In one example, we take 2200 pseudo-random points from five, two-dimensional Gaussian distributions, and use 1000 landmarks to compute the LSNE embedding. FIG. 35 depicts a visualization of a scatter plot of these points (i.e., ground truth). FIG. 36 depicts a visualization of a scatter plot of the LSNE lenses. Colors are referenced on the data points to make it easier to identify the correspondence. In this example, there is no specific association between the locations of the points in the ground truth and LSNE embedding, except that nearby points in the ground truth have a strong tendency to remain together in the embedding.

Figure 37:
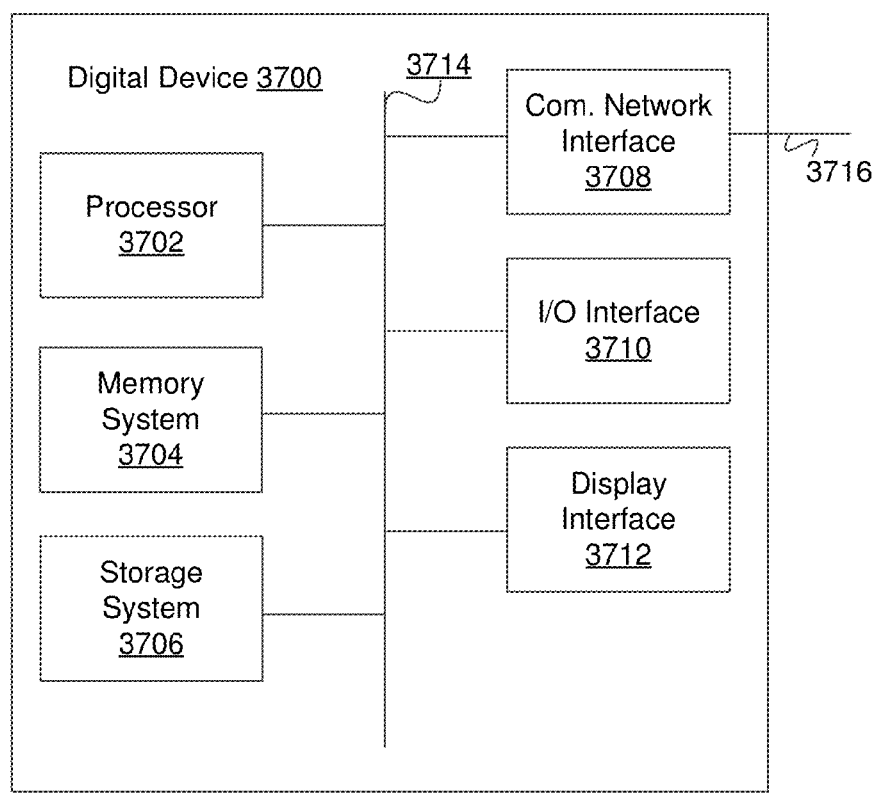
FIG. 37 is an exemplary digital device in some embodiments.

In another, more complex example, there is a data set from the Microarray Innovations in Leukemia (MILE) study. In this particular data set there are approximately 2000 samples, each with approximately 1500 columns of gene expression data together with a clinical classification of the particular type of leukemia. A metric that may be used in this case may be the result of a random forest classifier, and the points are colored by their clinical classification. In this example, all the points in the data set are used to compute the LSNE embedding. FIG. 37 depicts a visualization of the MILE data set in the reference space. The visualization may be colored by clinical classification.

The random forest metric in this case finds the clinical classification groups, and the LSNE embedding preserves these groups while doing a dimensionality reduction from 1500 dimensions to 2.

Figure 26:
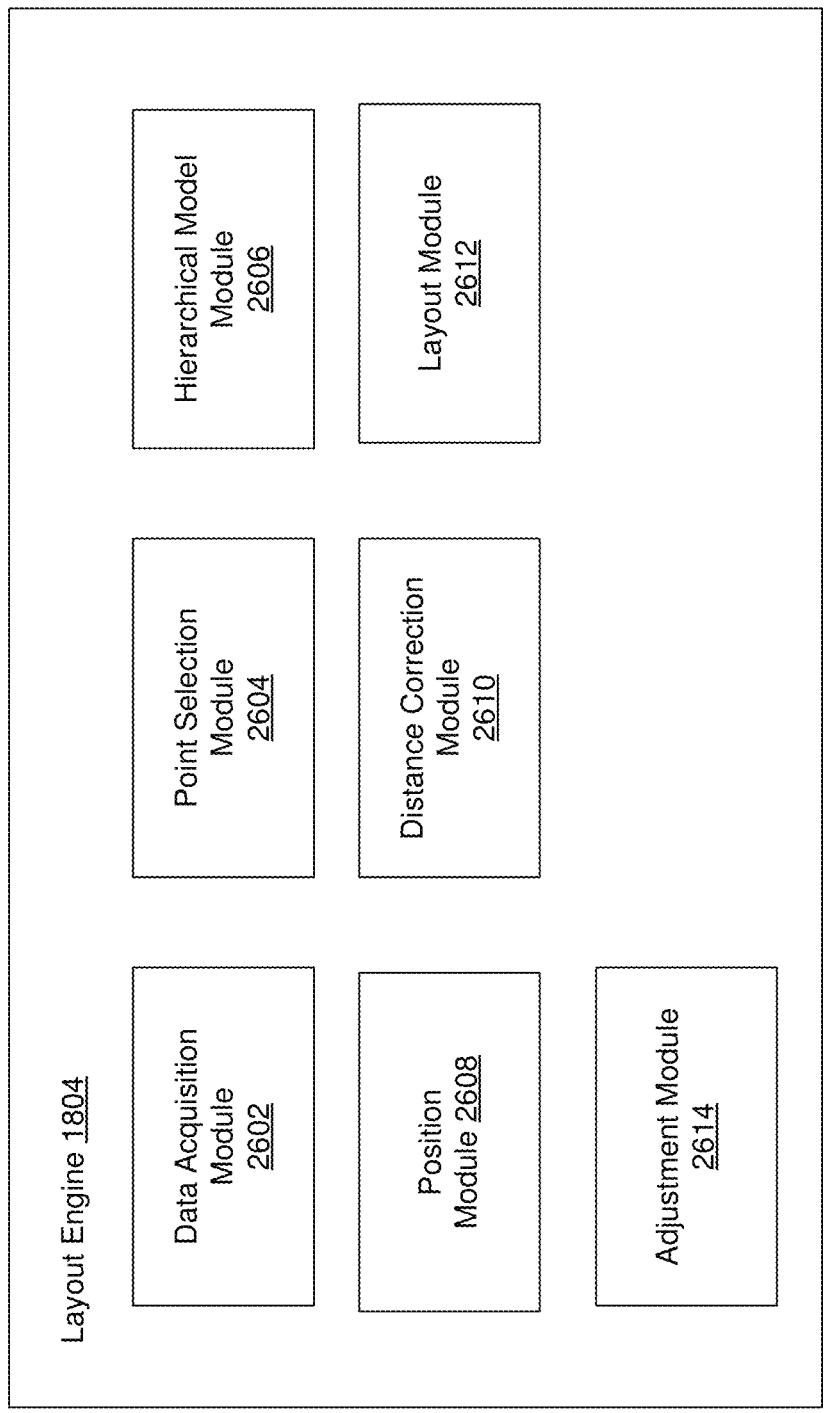
FIG. 26 is a block diagram of a layout engine in some embodiments.

FIG. 26 is a block diagram of a layout engine 1804 in some embodiments. The layout engine 1804 may organize and/or lay out the information in the reference space in any number of ways. In some embodiments, the layout engine 1804 may layout the information to generate a visualization. In other embodiments, the layout engine 1804 may layout the information (e.g., organize the information in memory).

In some embodiments, the layout may be performed in two stages. The first stage may comprise the determination and/or display of the initial layout. The second stage may comprise adjusting the initial layout with the goal of reaching a comprehensible and/or stable graph (in memory and/or as a visualization).

In a general example of the first stage of determining the initial layout, data for a graph may be received from the lens generation module 1802. Subsequently, a small subset (called the core) of points (e.g., nodes or balls) may be chosen. The subset may include points that will be displayed at different positions in the initial layout. Once the core points are positioned, subsequent subsets of points from the data are selected and may be positioned based on the core points and/or other points which are members of the selected core points.

Caused in part by the limited number of displayable dimensions (e.g., the reference space may be a plane), the position and/or distance of one or more points in the graph may not equate with the distances as mathematically derived from the received data. In order to improve the graphical layout, a potential may be determined for one or more points based on the mathematically derived distance and the distance as graphed. A graphical layout is a layout in the reference space regardless if the reference space is generated as a visualization or generated in memory (e.g., for further processing and/or analytics such as the use of clustering in the reference space and generating a visualization of relationships in the original received data based on the groups/clusters). The potential may then be minimized to adjust the position of the points.

In one example, a KK potential and gradient-descent (starting with an initial set of positions) may be utilized to lay out the points in the core. Points may be added based on those points already present (e.g., those points that have already been positioned or approximately positioned) and an approximation of the KK solution may be calculated. Once all the points from the data are added, the graph may be updated (e.g., distances and/or position corrected) utilizing gradient-descent on the KK potential.

In some embodiments, the layout engine 1804 comprises a data acquisition module 2602, a point selection module 2604, a hierarchical model module 2606, a position module 2608, a distance correction module 2610, a layout module 2612, and an adjustment module 2614. The layout engine 1804 may be any software, hardware, or a combination of both. The layout engine 1804 may be configured to layout and/or draw a graph such as, for example, a force-directed layout graph. The layout engine 1804 may be resident in a server, a user computer, or any other digital device.

The data acquisition module 2602 receives data that may be used to build the graph. The data may be within a table or any other data structure. The data may be in a combination of different data structures. In one example, the data within a table identifies points and edges. The position of the points and/or edges may be identified by vertice as well as by adjacent vertice(s).

Those skilled in the art will appreciate that the vertices and adjacent vertices may represent any kind of data. For example, a massive data set with many dimensions (e.g., thousands of dimensions) may be represented by one or more data structures identifying vertices as well as adjacent vertices.

The point selection module 2604 selects points (e.g., balls or nodes) to be positioned in the graph. Those skilled in the art will appreciate that the point selection module 2604 may select any number of points based on any number of methods. In various embodiments, the point selection module 2604 selects an initial subset of the available points (e.g., the core) from the received data. The selected points may be chosen at random, chosen based on some random information, or be purposefully chosen. In one example, the point selection module 2604 selects points that are the farthest distance (e.g., measured by edges) from the previously selected points. For example, the first point may be randomly selected and the second selected point may have the longest distance (e.g., as measured by the maximum number of edges) from the first point when compared to any other two points from the received data. The next selected point may have the longest distance from both the first two selected points when compared to any other point in the received data. Further, the next selected point may have the longest distance from the first three selected points when compared to any other point in the received data. This process may continue until all of the points for the first subset are selected.

There may be any number of initially selected points that make up the first subset from the received data. In one example, 25 points may be initially selected. The 25 selected points may make up the first selected subset. In another example, any number of points equal to or less than 100 points may be selected for the first subset. Each subsequent subset may, in some embodiments, include a greater number of points that the previously selected subset.

In various embodiments, a filtration of depth K (on a set of V points in a graph where |V| is N) is a tower of subsets, V0 being the entire set, V0>V1> . . . >VK, |Vi|/|Vi+1| is about 2, and |VK| is some minimal size.

In some embodiments, the point selection module 2604 or position module 2608 positions the core points more precisely than points that may be added at a later time. Subsequent sets of points may then be selected and ultimately added to the graph. In various embodiments, for every subsequently selected subset of points, the point selection module 2604 may select twice as many points as the previously selected subset of points. For example, one subset of points may include 110 points and, subsequently, the point selection module 2604 may select 220 points in the next subset of points. The layout engine 1804 may determine a position and/or adjust the position of each point in a subset before the point selection module 2604 selects the next subset of points.

The hierarchical model module 2606 and position module 2608 construct a Faster Approximate Distance Oracle (FADO), an ordering of the points that places the FADO core points first, and a pair of arrays, nearest—an int[N][3] that maps each point k to the three points that appear before it in the filtration which are closest to it, and distance, a double [N][3] that maps each point k to the graph distances of those three nearest neighbors. Those skilled in the art will appreciate that each point k may be mapped to any number of points and may not be limited to being mapped to those points that appear before k in the filtration. Further, each point k may be not limited to being mapped to points that are closest.

The hierarchical model module 2606 may construct a table or other structure that comprises distances (exact and/or approximations) between points. The construct or table may be a Faster Approximate Distance Oracle. The FADO may provide a mechanism for getting estimates of the position and/or distance between two or more points in a graph. In one example, the FADO comprises a table or other data structure that, for example, identifies every point. The position or distance of each point relative to one or more of the core points and/or previously positioned points may be determined. The FADO may comprise approximations of the position or distance of some points.

In some embodiments, the core of the FADO may be extracted for every non-trivial component or the graph. The core of the FADO and the component entries may be used to construct a permutation of the points of that component that places the core first. Then, the hierarchical model module 2606 or the position module 2608 may fill in "nearest previous neighbors" and their graph distances utilizing, for example, a repeated Dijkstra floodout. In some embodiments, this step may actually complete the building of the filtration instance. The reason that the ordering and the FADO may be built together (e.g., simultaneously or near-simultaneously) is that the core of the FADO may correspond to the initial set in the filtration. In some embodiments, the FADO stores only exact distance for log n points.

In various embodiments, the hierarchical model module 2606 and/or the position module 2608 may determine or correct a position and/or distances for a point and then perform a Dijkstra floodout to determine a predetermined number (e.g., 3) of previously placed points closest to the point to be placed. The hierarchical model module 2606 and/or the position module 2608 may determine the position of the point to be placed based on the predetermined number closest previously placed points. Those skilled in the art will appreciate that the points may be positioned relative to any number of points including the all or some of the core points, previously positioned points, or points to be positioned. In some embodiments, the layout engine 1804 stores the determined position or distance in the FADO.

The FADO may initially be described for a finite metric space. A complete distance matrix may be extended to a non-negative weighted graph given by points and edges. For example, let V be the metric space, choose a subset A. For each point x in A, the hierarchical module 2606 may compute distances between x and all other points. The approximate distance $e(x,y)$ may be defined to be min a in A of $d(x,a)+d(a,y)$. This may be an upper bound. Those skilled in the art will appreciate that if A is the whole space it is exact, but may not be usable. Further, if A is not too big, the calculation may be cheap. The storage overhead, for example, may be |V|*|A|. In some embodiments, an estimate of error is not determined, however, such estimates may be used. A subset may be chosen by taking max/min landmarks.

The hierarchical model module 2606 and/or position module 2608 may perform optional fixes to positions and distances in the FADO. For example, the hierarchical model module 2606 may construct, for each point x, a ball B(x), of some specified BX_SIZE (say 25) around x containing the nearest BX_SIZE points to x. Then the hierarchical model module 2606 may compute the distance between x and y by seeing if x is in B(y) or y is in B(x), and if not, taking the min a in A of $d(x,a)+d(a,y)$. This process may repair errors that come from taking two points quite close to one another and estimating their distance as being quite large. For example, for sampled 5-100 dimensional Euclidean spaces, this may make the average of estimated distance/actual distance to be about 1.05-1.2.

In various embodiments, when there is no distance matrix, but the position module 2608 may compute d(x,A) operations in sufficiently short amounts of time that the cost of the construction may still bounded by |V|*|A| for a graph of bounded degree. First, for each a in A the position module 2608 may perform a Dijkstra traversal to compute the distances from a to every point in V. As in the case of the metric space, the point selection module 2604 and/or the position module 2608 may choose A by taking max/min landmarks.

Subsequently, the hierarchical model module 2606, position module 2608, and/or the distance correction module 2610 may place core entries using full SSDE and then adjust using the KK potential force which can be computed on the core (e.g., because distances may be represented).

For each subsequent Vi after VK, i>0, the points may be placed using nearest/distance values and KKFInit. When all of the entries in a given Vi are placed, the hierarchical model module 2606, position module 2608, and/or the distance correction module 2610 may iterate over each point n of the partial graph using the KK potential computed on a randomly selected set of points of kkf_counts[i] also in Vi. kkf_counts[i] decreases fast enough that the cost of all of these operations is O(N*ln(N)) (assuming that the number of edges is O(N)).

For V0 the initial placement may go as before, but, in some embodiments, the iteration step may compute the KK potential on just the adjacent points (e.g., the last step only does a local refinement). There may be any number of iterations. In one example, the number of iterations is ten.

In various embodiments, the distance correction module 2610 adjusts the graphical distance of the points. In one example, the distance correction module 2610 attempts to equate graphical distance (e.g., the distance as may be displayed in the graph) with topologic distance (e.g., the distances as determined mathematically based on the receive data). If these distances are equal, the distance correction module 2610 may not perform any additional function. However, if these distances are not equal, the distance correction module 2610 may attempt to display the graph distance at a point that approximates that topologic distance. In some embodiments, distances may equate with position.

In various embodiments, topologic distance is the distance within the mathematically defined space between two or more points. Those skilled in the art will appreciate that the topologic distance may have any number of dimensions. When the graph data received by the data acquisition module 2602 is projected as a viewable graphic, the projection may limit the depiction of one or more dimensions used to display the points. As a result, the graphical distance (e.g., Euclidean distance) between two points as displayed in the graph may not equate the topologic distance between the two points as defined in the mathematical space.

In order to improve the layout of the graph, the graphical distance may be equated to the topologic distance and/or an approximation may be determined to allow the graphical distance to approximate the topologic distance. In various embodiments, the graphical distance between two or more points may be displayed in a manner that enables the user to perceive the graphical distance as approximating or representing the topologic distance.

In some embodiments, a potential may be calculated between two or more points. The potential may provide a gradient that may be decreased and/or minimized to improve a graphical distance approximation. In one example, the distance correction module 2610 may determine the potential using the KK potential. The distance correction module 2610 may subsequently apply a gradient descent upon the potential to determine the graphical approximation to the topologic distance.

In an example of utilizing the KK potential, a potential function a graph may compare the relative distances, denoted |X−Y|, of the point positions in Euclidean (e.g., displayed graph) space, where the position of point i is denoted by loc(i), to their interpoint distances in the intrinsic graph metric, Denoted DG(i,j). In some embodiments, if we define err(i,j) as err(i,j)=(|loc(i)−loc(j)|−DG(i,j)) we may then define the stress of the graph to be:

stress(G)=SUM(i<j in G){(W(i,j)*SQUARE(err(i,j)))} for some positive, symmetric weight function W(i,j).

The weight function may be DG(i,j) to some negative power such as 1/(DG( )*DG( )). in that case:

stress(G)=SUM(i<j in G){SQUARE((|loc(i)−loc(j)|/DG(i,i))−1.0)}

We may define a real-valued function from R2, say, by defining the stress of the graph with point i at X to be:

stress(G,X)=SUM(j!=i) in G){SQUARE((|X−loc(j)|/DG(i,j))−1.0)}

In this case, the negative gradient may be:

−2.0*SUM(j!=i){(((|X−loc(j)|/DG(i,j))−1)([X−loc(j)]/(DG(i,j)|X−loc(j)|))} or

−2.0*SUM(j!=i){1/DG(i,j)*(1/DG(i,j)−1/|X−loc(j)|)*[X−loc(j)]}

We may use this gradient, normalized, to graph and/or display a force-directed layout.

For example, for a KK solution for a 4 point (e.g., 4-point) problem, if there is a point that wasn't placed, the distance correction module 2610 may attempt to place the point by finding the three closest points that were already in place (e.g. points whose positions have been determined), and then the distance correction module 2610 may place the point at the spot that minimizes the KK potential for those 4 points.

In various embodiments, in order to determine the placement of a new point, three points are selected (e.g., wherein the three points have already been placed within the graph) and the new point may be placed in the spot that minimizes the potential for each pair of the three points. The minimum may be either 1 or 2 points. In some embodiments, the three points that are closest together may be selected and the barycenter (a+b+c/3) of those three points may be determined. The new point may be placed at or near the barycenter.

For example, for hierarchical layouts, the distance correction module 2610 may take K points already placed, and then the distance correction module 2610 may place X so as to minimize the potential for that point. The distance correction module 2610 may take K to be all the points, but that may make the problem at least N-squared.

Those skilled in the art will appreciate that two points may be relatively simple to solve, however, if P1 is at (0,0) and P2 is at (1,0), then regardless of X=(x,y), the point (x,−y) also may have the same potential (for those 3 points). As a result, the distance correction module 2610 may take three points. Further, those skilled in the art will appreciate that although the KK potential may be determined for three general points and a fourth may be added, the result may be close to the barycenter of the three closest 3-point solutions.

After the potential is determined, the distance correction module 2610 may perform a "relaxation" step wherein the distance correction module 2610 minimizes or approximates the minimum of the potential function for the graph as currently constructed (e.g., for those points which have been graphically displayed and/or positions have been determined). The "relaxation" step may be performed as one or more of the placements of points are determined. Those skilled in the art will appreciate that as this process is completed at the initial stages, the results will improve at the time the graph layout is completed since it is possible that not all the points in the end of the process may be accounted (e.g., to take into account all points at the end of the process may be computationally too expensive).

In various embodiments, the gradient of the potential for each point (pretending that all the other points are fixed) is approximated. In one example, a predetermined number of points may be chosen. The points may be chosen at random or order may be included in the process of choosing points. For example, several points that are a maximum number of edge lengths away from each other and/or the other selected points may be chosen. The gradient may then be computed. In some embodiments, for the last "relaxation" step, the points that are connected to X may be taken to make a gradient. Those skilled in the art will appreciate that there are many ways to approximate the gradient of the potential.

Many methods may be used to adjust the position or distance of the points. For example, the distance correction module 2610 may perform a gradient descent with a max step-size and remembering the last step because the potential may have oscillations which may be damped. The gradient descent may also be computationally reasonably quick. Those skilled in the art will appreciate that that the points may be moved in any number of ways, including, but not limited to, the Runge-Kutta method for getting a higher-order approximate solution.

Once the initial position and/or distance for each point is determined, the layout module 2612 may display the points within the graph. In some embodiments, the layout module 2612 displays any number of points before the initial position and/or distance of all points are determined. In various embodiments, the layout module 2612 may not display the graph until one or more points of the graph are adjusted by the adjustment module 2614.

In various embodiments, once the position and/or distances are determined for each point, the position of one or more points is adjusted by the adjustment module 2614. The adjustment module 2614 may move or adjust points to ensure that all forces acting upon each point cancel and there is no net effect. If all forces upon a point cancel, then the points may no longer be moved.

In some embodiments, the adjustment module 2614 determines forces upon a point. The forces may include the force provided by the edges coupled to the point as well as forces that are provided via a subset of points in the graph. The subset need not be coupled to the subject to produce a force. For example, for a subject point, the adjustment module 2614 identifies a subset of points of the graph that may enact a force on the subject point and identifies the forces on the subject point provided by the edges.

The adjustment module 2614 may provide the position module 2608 a new position for the subject point that may allow the forces on the subject point to cancel or otherwise trend towards a zero net effect. In some embodiments, the adjustment module 2614 may adjust or direct the position module 2608 to adjust the position of a point until the forces that are enacted on that point become zero force or are within a predetermined threshold (e.g., within a proximity of zero force). The adjustment module 2614 may spread one or more points apart by enforcing the spring or energy of connecting edges as well as the forces provided by the identified subset.

The adjustment module 2614 may select a different subset of points for one or more different points. For example, each point may be influenced by a different subset of points. If a member of a subset provides a force on a subject node, the subject node may also provide a force on the member of the subset in return. As a result, all forces throughout the graph may cancel depending on the positions of the points.

In one example, the edges (e.g., springs) have a desired length, which may be constant (e.g., 1.0 for all edges in the graph). The edges may also repel (e.g., through a function similar to Hooke's law) when connected points are too close and attract when the connected points are too far apart. When a component has too many points (e.g., a component's points are greater than 100), instead of using N*N calculation, the adjustment module 2614 may construct balanced samples of the component of a predetermined size (e.g., 20). When the adjustment module 2614 uses samples, the adjustment module 2614 may compute the gravitational force on a point x by computing the usual "gravitational" force exerted by each point in sample[x] on x, and then multiplying that force by (N−1)/(# in sample[x]). The size of sample[x] may be the same for all x, when the adjustment module 2614 samples, but it is possible for sample[x] to have repeated values (but x may not be in sample[x]).

In various embodiments, the adjustment module 2614 constructs a set of size 'balanced samples' of [0,modulus−1]. The return value, samples[ ][ ], may be an int[modulus][size], where samples[i] is a 'random' subset of [0,modulus−1]. The samples may be balanced in that if A appears in samples[B] n times, then B appears in samples[A] the same number of times, and X in [0,modulus−1] appears precisely size times in all of the samples.

In some embodiments, being balanced means that the net force on a component may be 0, and it spreads the pairs around the component. If the component is of size N, and the samples are of size K, then recall the adjustment module 2614 may multiply the force by (N−1)/K to adjust for looking at fewer points (in other words, it really is the ratio of the number of points looked at vs. how many that would have been looked at in the non-sampling case).

Those skilled in the art will appreciate that one way to make these balanced samples is to take the "columns" to be given by permutations of the set that do not have fixed points (e.g., no point can push on itself), and make sure that the permutation and its inverse are both included (so we throw out an self-inverses). Permutations may be avoided that have short cycles (if there is a small subset that the permutation keeps fixed, then everything in that set may be ignoring the rest of the component).

In some embodiments, the particular permutations used by the adjustment module 2614 may map the elements from [0, N) by x->(A*x+B) % N, where B is non-zero and A is relatively prime to N. They may be simple, and may seem to have relatively long periods. Those skilled in the art will appreciate that the adjustment module 2614 may choose permutations at random, or construct them in other ways. In various embodiments, it is not necessary to use permutations.

In some embodiments, the layout engine 1804 stores only n log n positions and/or computations in storage as opposed to n*n positions or computations as required by the prior art. As a result, in some embodiments, techniques discussed herein may be more computationally efficient than those in the prior art.

Figure 27:
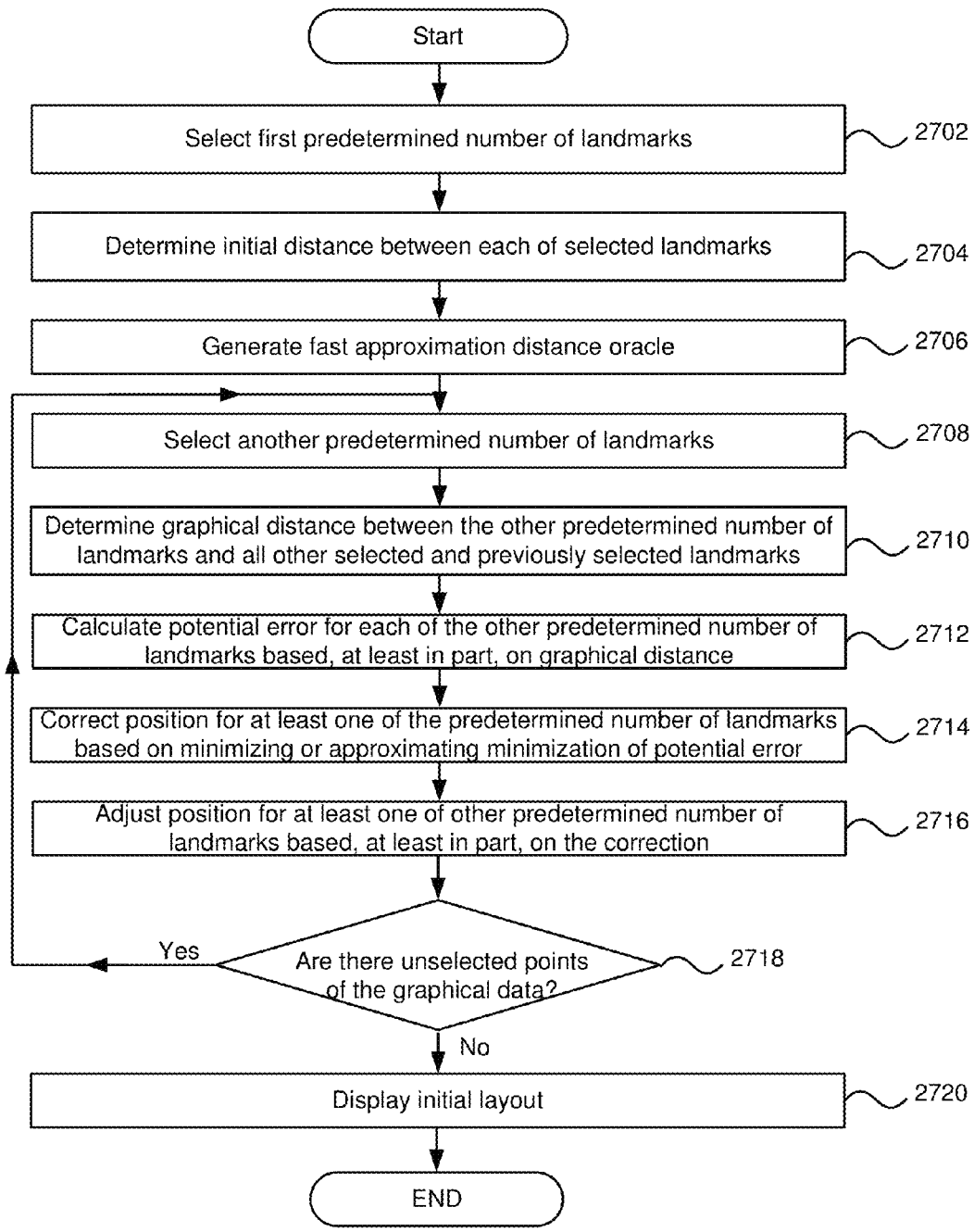
FIG. 27 is a flow chart of a method for an initial graph layout in some embodiments.

FIG. 27 is a flow chart of a method for an initial graph layout in some embodiments. In step 2702, the data acquisition module 2602 receives data to graph. In some embodiments, the data may be a table or other data structure comprising information associated with points and edges. In one example, the data structure comprises a list of vertices and adjacent vertices. In various embodiments, the data acquisition module 2602 may be configured to convert data in any format or combination of formats into a table or other data structure of points and edges.

In step 2704, the point selection module 2604 may select a first predetermined number of points (called the core). In some embodiments, the core points may be spaced throughout the general graph. The points may be randomly selected. In some embodiments, subsequently selected points may also be random or selected based, in part, on distance from previously selected points. As a result, the placement of subsequent points may also be spaced across the graph. Those skilled in the art will appreciate that each subsequent set of points may be built around the core and the previously positioned points.

In step 2706, the position module 2608 may determine an initial distance between each of the first predetermined number of points. The position and/or distance of each of the first predetermined number of points may be determined based on the received data. In some embodiments, the selection of points for the first predetermined number of points may occur simultaneously or near simultaneously. For example, although the first point of the core may be chosen at random, a second point may be selected that is the farthest distance (e.g., as measured by number of edges) from the first selected point. As a result, the position of the second core point may be determined as a part of the process of point selection. The next selected point may be the farthest distance from the first and second selected points. The process may continue in a like fashion until the core points are selected. The next predetermined number of points may be positioned based, in part, on the position of the core points. The third predetermined number of points may each be positioned based, in part, on the positions of the core points as well as the positions of the second predetermined number of points. This process may continue until all of the points are selected. In some embodiments, all points are randomly selected.

In some embodiments, the core points may be selected and/or positioned using an eigenvector approach where the first two eigenvalues are correlated to the x and y axis, respectively. The eigenvector may position the core points in a computationally efficient manner. Once the core points are selected, subsequent points may be selected and/or positioned based on the FADO as described herein. Although eigenvector approaches can be efficient for limited uses, these approaches may not effectively scale and, further, eigenvector approaches may cause significant changes in a depicted graph if the graph is altered (e.g., changed by a user selecting and dragging one or more points for an improved layout).

In step 2708, the hierarchical model module 2606 may construct the fast approximate distance oracle (FADO). The FADO may be a reference table or other data structure that comprises point identifiers and at least some positions and/or distances between points. The positions of points and/or distances between points of the core of the FADO may be determined. Positions and/or distances determined and stored in the FADO may be approximations thereby potentially increasing computational efficiency.

Those skilled in the art will appreciate that the FADO may assist in the initial layout of the graph. The FADO may contain point identifiers as well as information associated with the points that allow for the determination or calculation of positions of one or more points and/or distances between one or more points.

In some embodiments, the FADO is optional. For example, distances and positions may be determined based on subsequently placed points as discussed herein without referring to a data structure that previously stored the information.

In step 2710, the point selection module 2604 may select another subset of points. Each subsequent subset of points may be larger than the previous subset. In some embodiments, every subset of points selected after the initial subset may contain points that were randomly selected. In some embodiments, the points may be selected in a manner similar to the selection of points of the first subset (e.g., based on position and/or distance from previously selected points).

In step 2712, the distance correction module 2610 determines graphical distance between the other predetermined number of points and all other selected and previously selected points. The position of the newly selected points may be based, at least in part, on information contained with the FADO. For example, the point selection module 2604, hierarchical model module 2606, and/or the position module 2608 may retrieve or compute graphical distances between each of the points of the newly selected subset as well as graphical distances between each of the newly selected points and the previously selected points. One or more of the graphical distances may be approximated and/or based on previous approximations.

In step 2714, distance correction module 2610 may calculate a potential error for reach of the other predetermined number of points based, at least in part, on the graphical distance. In one example, the point selection module 2604, hierarchical model module 2606, and/or the position module 2608 determines a topologic distance between two or more points. The topologic distance may, in some embodiments, be stored in the FADO. The distance correction module 2610 may compare the graphical distance to the topologic distance to determine and/or calculate a potential error. If there is no error or the error is within a predetermined error margin, no potential error is calculated in the process may go to step 2720. In some embodiments, the potential error may be represented as a potential (e.g., kk potential).

If the graphical distance and the topologic distance between two or more points are not equal, the distance correction module 2610 may determine a correct position for a point based on minimizing or approximating minimization of the potential error. In one example, the distance correction module 2610 minimizes or approximates the minimization of the potential (e.g., kk potential).

In step 2718, the position module 2608 and/or the layout module 2612 may adjust the position of at least one point based, at least in part, on the correction. In various embodiments, the adjustment to the position and/or distance is stored in the FADO. In some embodiments, the adjusted position of the point is displayed and/or stored in any data structure.

In step 2720, the point selection module 2604 determines if there are any unselected points from the graph data. If not, all points have been selected and their positions or distances determined, the method may continue in step 2710 where the point selection module 2604 may select another subset of points.

In step 2722, the layout module 2612 displays the initial layout. In various embodiments, the layout module 2612 displays all points and edges simultaneously or near simultaneously. In one example, the layout module 2612 depicts the initial layout when all positions with potential error have been adjusted. In some embodiments, the layout module 2612 depicts each point of the graph if there is no potential error or upon correction of the potential error. Those skilled in the art will appreciate that, however, that any number of points may be displayed at any time. For example, the layout module 2612 may display any number of points after positions and/or distances of a predetermined number of points has been determined and/or corrected. In some embodiments, the layout module 2612 displays each point as soon as the initial position is determined. Subsequently, the layout module 2612 may visually adjust the position of the point as necessary.

Figure 28:
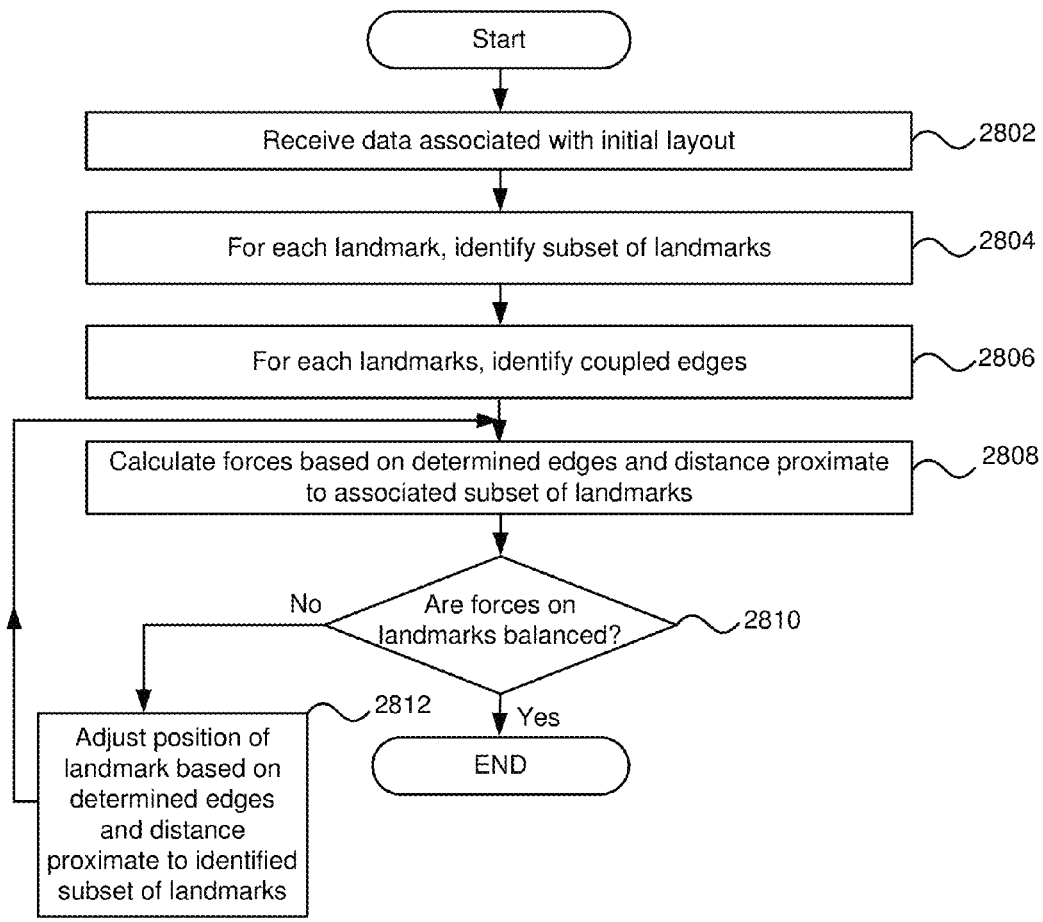
FIG. 28 is a flow chart of a method for adjusting the graph layout in some embodiments.

FIG. 28 is a flow chart of a method for adjusting the graph layout in some embodiments. In step 2802, the layout engine 1804 receives data associated with the initial layout. In some embodiments, this step is optional. For example, the layout engine 1804 may have generated the initial layout, and, as a result, does not to retrieve or otherwise receive the data associated with the initial layout. In some embodiments, the layout engine 1804 may generate and provide the initial layout to one or more digital devices, processors, storage devices, and/or buffers. Those skilled in the art will appreciate that the layout engine 1804 may retrieve the initial graph layout from one or more sources. In some various, there are multiple graph layout engines including a first engine that prepares the initial graph layout while the second engine performs the adjustments.

In step 2804, the point selection module 2604 and/or the adjustment module 2614 may identify a subset of points for each point of the initial layout. Each point of the initial layout may be associated with a different subset of points. The points of the subsets may be termed "antigravity" points. In some embodiments, one or more points may be positioned, at least in part, relative to one or more of the antigravity points as if there was an edge applying a force. For example, a point may be coupled to three other points by three edges. The graph may have four antigravity points. The point may be subject to the forces of the three edges as well as forces that would be derived if the point was coupled to the antigravity points by additional edges. The points of the subset(s) may be located at different positions throughout the graph (e.g., in a manner similar to the core points that are initially selected during the initial layout).

There may be any number of antigravity points associated with at least one other point. For example, there may be 100 antigravity points applying force to one other point. In some embodiments, a first point may act as an antigravity point to 100 points which, in turn, act to provide force as antigravity points to the first point.

In various embodiments, one or more points of the initial layout may be influenced by different subsets of antigravity points. The applied forces may be symmetrical. For example, if two points are coupled by an edge, both points will be affected by the force of the edge. Similarly if a first point acts as an antigravity point to a second point, the second point may act as an antigravity point to the first point.

In step 2806, the adjustment module 2614 identifies edges and forces, if any, for each point of the initial layout. In step 2808, the adjustment module 2614 calculates the forces on each point based on the identified edges and the associated subset of antigravity points. In various embodiments, the adjustment module 2614 may enforce forces associated with actual edges and/or points that are proximate (e.g., without a predetermined distance threshold). For example, the adjustment module 2614 may determine the forces acting upon a point as including actual edges of the point as well as the forces between proximate one or more antigravity points (e.g., one or a subset of all of the antigravity points).

In step 2810, the adjustment module 2614 may determine if all of the forces on all of the points are balanced. If they are not balanced, then, in step 2812, the adjustment module 2614 may adjust the position of one or more points based on predetermined edges and distance proximate to the identified subset of points (e.g., the core). In some embodiments, the layout module 2612 depicts the adjustment during or after the position is adjusted. The process continues in step 2808 where the adjustment module 2614 may recalculate, based in part on the new positions of one or more points, the forces based on the determined edges and distance proximate to the associated subset of points. Alternately, if the forces on all points are balanced, the method may end.

Those skilled in the art will appreciate that, in some embodiments, all points are assessed and changes made to the position or distance of points simultaneously or near simultaneous. In some embodiments, one point or a subset of points are selected. For each selected point, the adjustment module 2614 may identify points and edges, calculate the forces based on the edges as well as the assumed edges to the antigravity points, and make the changes. Subsequently, another subset of previously unselected points may be similarly assessed and adjusted, and so on.

Figure 29:
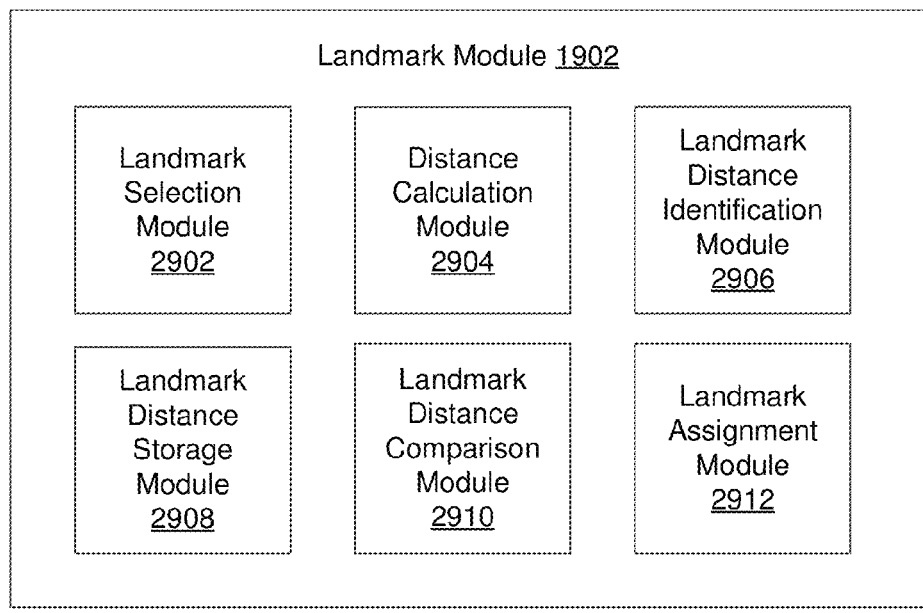
FIG. 29 shows exemplary landmark module configured to identify landmark points that approximate or represent a larger collection of data points in accordance with various embodiments.

FIG. 29 shows exemplary landmark module 1902 configured to identify landmark points that approximate or represent a larger collection of data points in accordance with various embodiments. In this example, landmark module 1902 comprises landmark selection module 2902, a distance calculation module 2904, a landmark distance identification module 2906, a landmark distance storage module 2908, a landmark distance comparison module 2910, and a landmark assignment module 2912.

The landmark selection module 2902 may be configured to randomly select a first subset of the data points to assign as an initial set of landmark points. For example, the landmark selection module 2902 may select an initial set of points from the finite metric space as a landmark set L. It will be appreciated that the landmark selection module 2902 may select points pseudo-randomly (e.g., randomly within the bounds of software or computer implementation) and/or in combination with other methods (e.g., randomly within portions of the finite metric space or based, in part, on density of information). Landmark selection module 2902 may select points in any number of ways.

The distance calculation module 2904 may be configured to calculate the distances between a respective non-landmark data point and each landmark point in the finite reference space. In some embodiments, the distance calculation module 2904 stores some or all of the information for later use. For example, the distance calculation module 2904 may calculate distances which are later used by the lens generation module 1802.

The landmark distance identification module 2906 may be configured to identify the shortest distance from among the distances between the respective non-landmark data point and each landmark. The shortest distance between a non-landmark data point and a landmark data point may indicate the closest landmark to that particular non-landmark data point.

The landmark distance storage module 2908 may be configured to store the shortest data point distance for the respective non-landmark data point as a landmark distance for that data point. The landmark distance comparison module 2910 may be configured to determine a longest landmark distance from among the shortest distances (e.g., stored by the landmark distance storage module 2908) to a nearest landmark for each data point.

The landmark assignment module 2912 may be configured to add a data point associated with the longest landmark distance to the initial set of landmark points (e.g., thereby adding a new landmark).

As described herein, the landmarks (L) are a subset of the collection data points in the finite metric space. The landmarks may be chosen such that the subset is representative of or to approximate the received data. In some embodiments, the landmarks are chosen to reflect both the "average" and "extreme" behavior of the data points in the space and, thus, analytics and other operations performed on the landmark set as an approximation of the behavior of the whole metric space (X). In some embodiments, the landmark points may be used as a means of increasing scale and performance when working with a large collection of data by only operating on a subset of a space.

Figure 30:
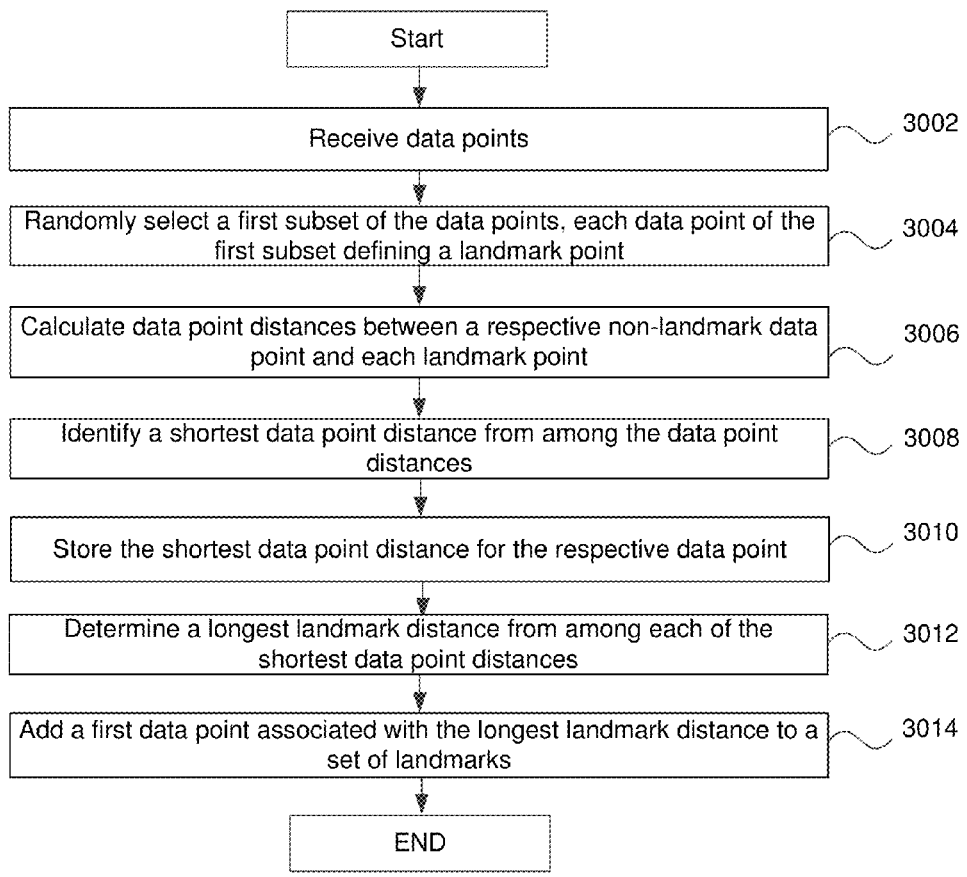
FIG. 30 is a flow chart depicting an exemplary method for generating a set of landmark points from a data set in some embodiments.

FIG. 30 is a flow chart 3000 depicting an exemplary method for generating a set of landmark points from a data set in some embodiments. The following discussion regarding the steps in FIG. 30 will be described with references to FIGS. 31A-D and FIG. 32. In step 3002, the landmark module 1902 receives a set of data points defining a finite metric space. For example, receiving data may include landmark module 1902 accessing a data structure containing a very large volume of multidimensional data, as shown in FIG. 31A.

Figure 31A:
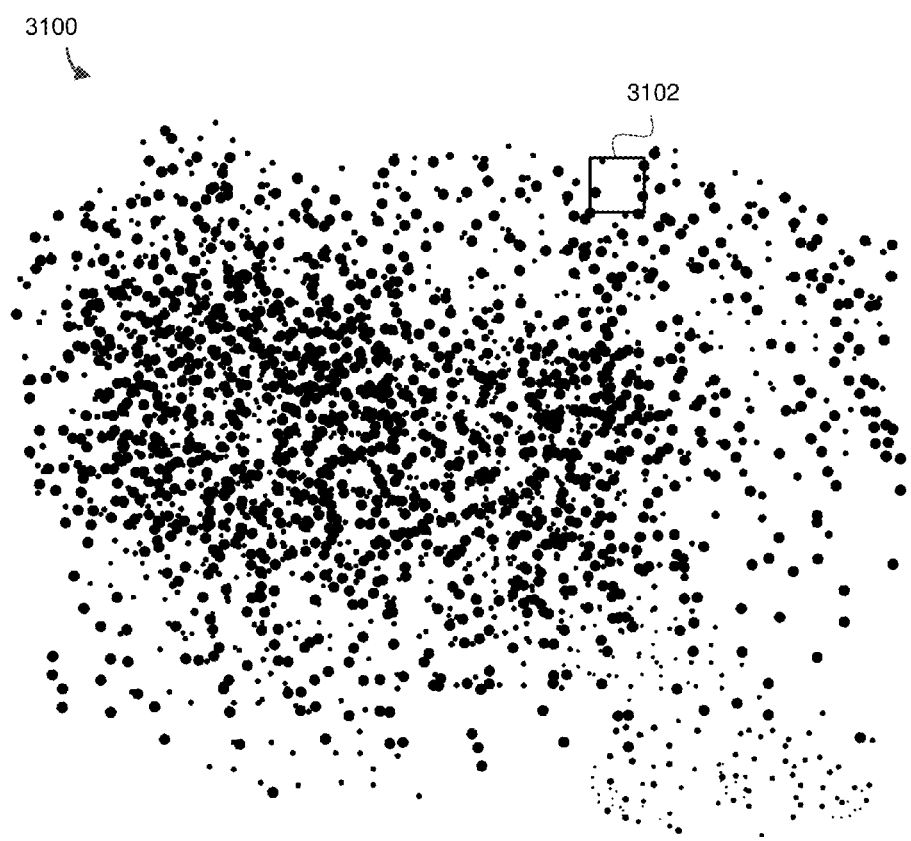
FIG. 31A shows exemplary metric space containing data in accordance with various embodiments.
Figure 31B:
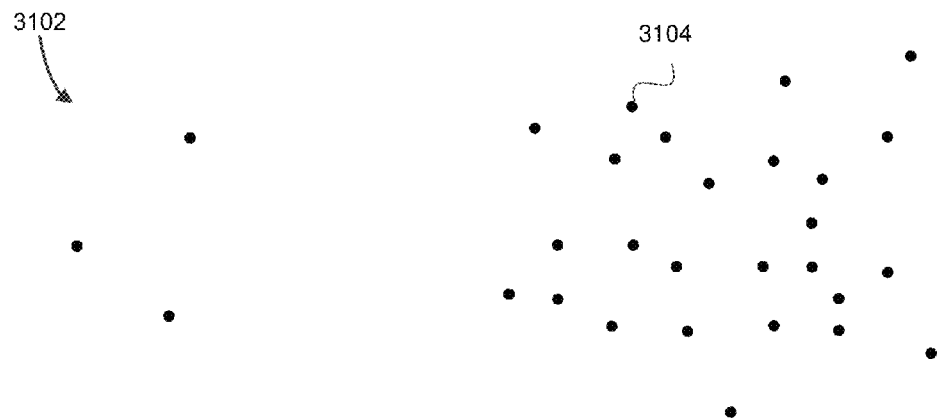
FIG. 31B shows subset composed of individual data points in accordance with some embodiments.

FIG. 31A shows exemplary metric space 3200 containing data in accordance with various embodiments. Since the amount of data shown in metric space 3200 and handled by the methods and algorithms discussed herein may be large (e.g., on the order of 200 million+ data points), subset 3202 of metric space 3200 will be used for discussion purposes. Accordingly, FIG. 31B shows subset 3202 composed of individual data points 3204 in accordance with some embodiments.

Figure 31C:
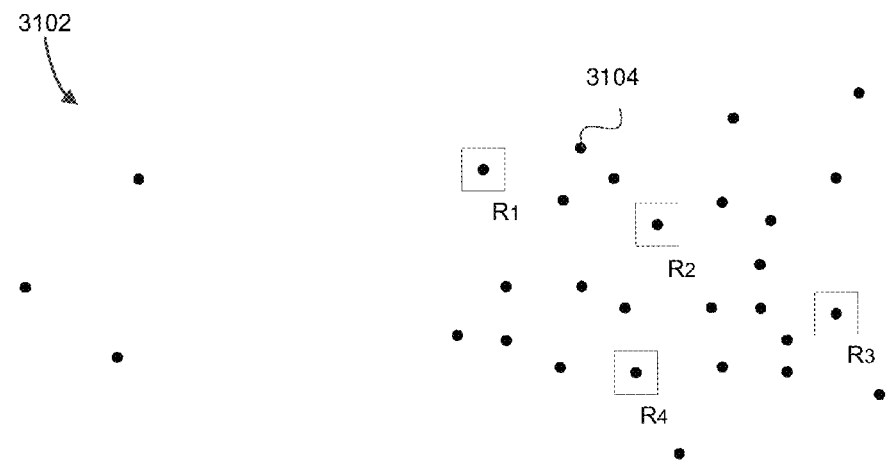
FIG. 31C shows exemplary random landmarks $R_1$, $R_2$, $R_3$, and $R_4$ that have been randomly selected from subset.

At step 3004, landmark selection module 2902 selects a random subset of individual data points 3204 as a first set of landmark points. To illustrate this step, FIG. 31C shows exemplary random landmarks $R_1$, $R_2$, $R_3$, and $R_4$ that have been randomly selected from subset 3202. Since metric space 3200 is large (e.g., 200 million+ data points), points selected at random tend to be located in high density areas, which is a benefit when attempting to choose a subset of points that represent the characteristics of the larger space. For example, for a metric space of approximately 200 million data points, the number of randomly selected landmark points could be approximately 5,000 points. Thus, the probability that a significant portion of the randomly selected landmarks may end up being outliers, for example, may be quite low and the randomly selected landmarks end up being located in higher density data point regions.

Figure 31D:
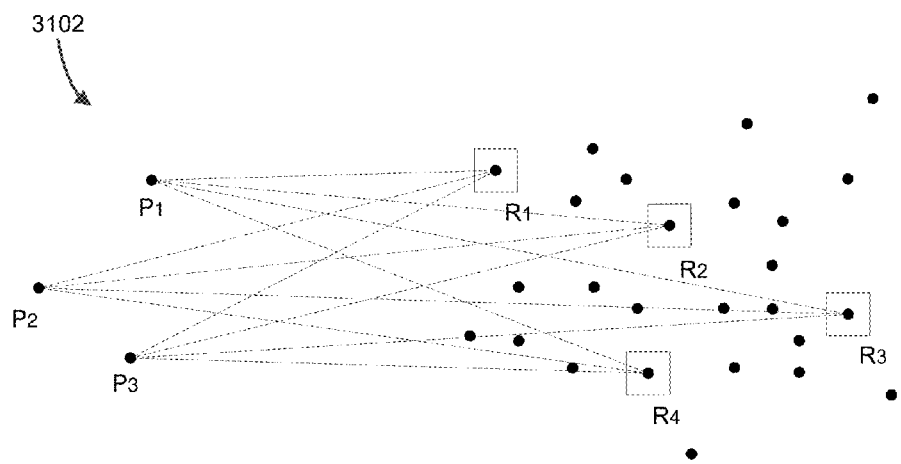
FIG. 31D shows lines corresponding to data point distances to each landmark for three points ($P_1$, $P_2$, and $P_3$)
Figure 32A:
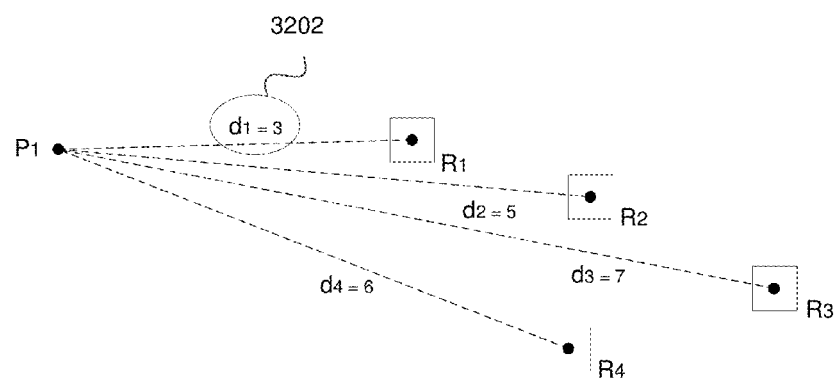
FIG. 32A shows exemplary data point distances between point $P_1$ and random landmarks $R_1$, $R_2$, $R_3$, and $R_4$.
Figures 32B, 32C:
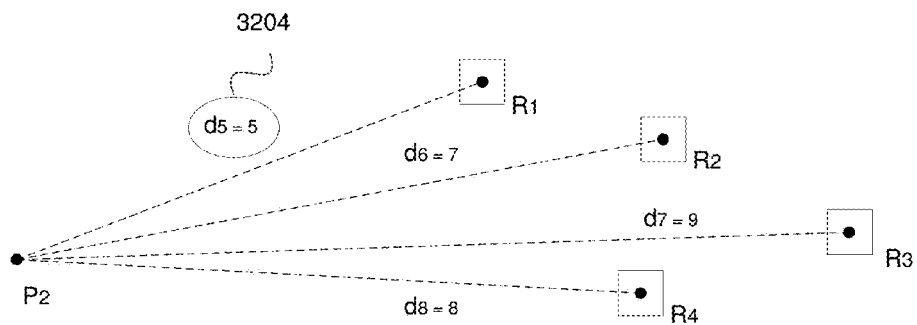
FIG. 32B shows exemplary distances between point $P_2$ and random landmarks $R_1$, $R_2$, $R_3$, and $R_4$.
FIG. 32C shows an exemplary table wherein the distances for each point are stored.

At step 3006, distance calculation module 2904 computes the distances between the random landmarks and all other non-landmark points in metric space 3100. As used herein, the distances between landmark points and individual data points 3204 are referred to as data point distances. Accordingly, FIG. 31D shows lines corresponding to data point distances to each landmark for three points ($P_1$, $P_2$, and $P_3$). It should be appreciated that the data point distances for all other points other than $P_1$, $P_2$, and $P_3$ and the landmarks are also calculated, but of clarity and illustrative purposes, the lines shown in FIG. 31D have only been drawn for $P_1$, $P_2$, and $P_3$. Accordingly, in this example, each distance between $P_i$ and $R_1$, $R_2$, $R_3$, and $R_4$ is calculated, each distance between $P_2$ and $R_1$, $R_2$, $R_3$, and $R_4$ is calculated, etc. until the distances between each non-landmark point and all the landmarks are calculated. FIGS. 32A-32B show this process in more detail.

FIG. 32A shows exemplary data point distances between point $P_1$ and random landmarks $R_1$, $R_2$, $R_3$, and $R_4$. In this example, distance $d_1$ between $P_1$ and $R_1$ is 3, distance $d_2$ between $P_i$ and $R_2$ is 5, distance $d_3$ between $P_1$ and $R_3$ is 7, and distance $d_4$ between $P_1$ and $R_4$ is 6. As used herein, the landmark distance for a respective non-landmark point is defined as the shortest distance to its nearest landmark or the shortest data point distance. Thus, distances $d_1$, $d_2$, $d_3$, and $d_4$ are compared to each other to determine which is the shortest (i.e., shortest distance to a landmark from $P_1$). In this example, distance $d_1$, between $P_1$ and $R_1$, is the shortest distance and, thus, defined as landmark distance 3302 for $P_1$. Accordingly, $R_1$ is the closest landmark to $P_1$ with corresponding landmark distance 3302 (i.e., $d_1=3$).

Similarly, FIG. 32B shows exemplary distances between point $P_2$ and random landmarks $R_1$, $R_2$, $R_3$, and $R_4$. In this example, distance $d_5$ between $P_2$ and $R_1$ is 5, distance $d_6$ between $P_2$ and $R_2$ is 5, distance $d_7$ between $P_2$ and $R_3$ is 9, and distance $d_8$ between $P_2$ and $R_4$ is 8. As above, distances $d_5$, $d_6$, $d_7$, and $d_8$ are compared to each other to determine which is the shortest distance to $P_2$'s nearest landmark, which is distance $d_5$. Accordingly, distance $d_5$ between $P_2$ and $R_1$ is landmark distance 3304. Thus, $R_1$ is also the closest landmark to $P_2$ at landmark distance 3304 (i.e., $d_5=5$), in this example.

Accordingly, the distance calculations described in FIGS. 32A and 32B are, thus, calculated for $P_3$ and every other non-landmark point in metric space 3200 and the distance calculations are stored along the way. For example, FIG. 32C shows an exemplary table 3250 wherein the distances for each point are stored. In this example, only the distances for points $P_1$ and $P_2$ are shown, but it should be appreciated that such a table or array would include distances for each non-landmark point. Thus, in one embodiment, table 3250 stores the distances for each point to each landmark in metric space 3100. From these distances, a landmark distance (e.g., shortest distance to a nearest landmark) for each point is identified and compared to generate a second set of landmark points. This process is discussed further with respect to FIGS. 33A-33D.

Figures 33A, 33B:
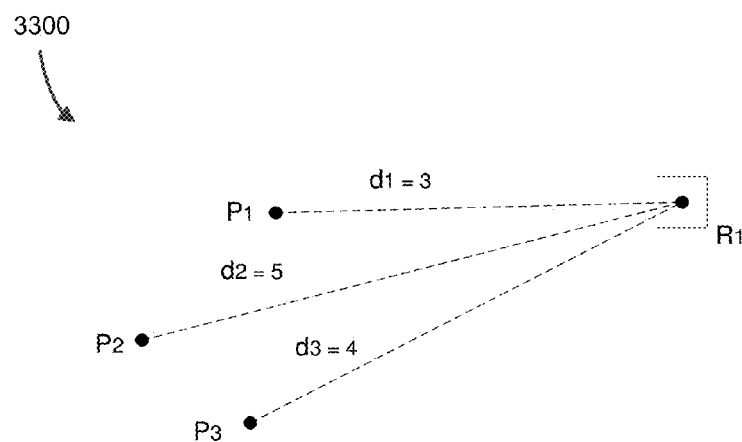
FIG. 33a shows exemplary landmark distances for points $P_1$, $P_2$, and $P_3$ landmark $R_1$ which can be used to demonstrate the selection of additional landmark points.
FIG. 33b shows a table of shortest distance from each non-landmark point to a landmark point (or the distance to the nearest landmark.

At step 3008, landmark distance identification module 2906 identifies the shortest data point distance from among the data point distances stored in table 3250. FIG. 33A shows exemplary landmark distances for points $P_1$, $P_2$, and $P_3$ landmark $R_1$ which can be used to demonstrate the selection of additional landmark points. For example, landmark distance identification module 2906 determines for each point which landmark point is the closest landmark point for that respective point. This may include, for example, comparing the distance values $d_n$ from table 3250 for each point to determine which distance $d_n$ is the shortest. Accordingly, in this example, the shortest distance to a landmark point from $P_1$ is 3 to landmark point $R_1$ and the shortest distance to a landmark point from $P_2$ is 5 also to landmark point $R_1$.

Such an operation may use an indexable state for X (i.e., points such as $P_1$, $P_2$, and $P_3$ in metric space 3100), an indexable array for L (e.g., L[l] is the index in X of the l'th landmark) where each random landmark point $R_n$ and subsequently determined landmark point is in L, and dClosest

[x] which records the shortest distance between X[x] (i.e., $P_1$, $P_2$, $P_3$, etc.) and a respective closest landmark point, and inL[ ] with is true if x is in L.

At step 3010, landmark distance storage module 2908 stores the shortest distance from each non-landmark point to a landmark point (or the distance to the nearest landmark) in an array, such as table 3350 shown in FIG. 33B. At step 3012, landmark distance comparison module 2910 determines a longest landmark distance from among each of the shortest data point distances (or a longest landmark distance) from among each of the landmark distances. For example, returning to FIG. 33A, random landmark point $R_1$ is the landmark nearest to points $P_1$, $P_2$, and $P_3$ and, thus, the landmark distance $l_n$ (i.e., the distance to a nearest landmark) for each of these points is its respective distance to $R_1$, which is stored in table 3350. Thus, in this example, the landmark distance for $P_i$ is $l_1=3$, the landmark distance for $P_2$ is $l_2=5$, and the landmark distance for $P_3$ is $l_3=4$. Accordingly, landmark distance comparison module 2910 compares these distances to identify the longest distance which, in this example, is $l_2=5$ shown circled in FIG. 33B, belonging to point $P_2$.

Figure 33C:
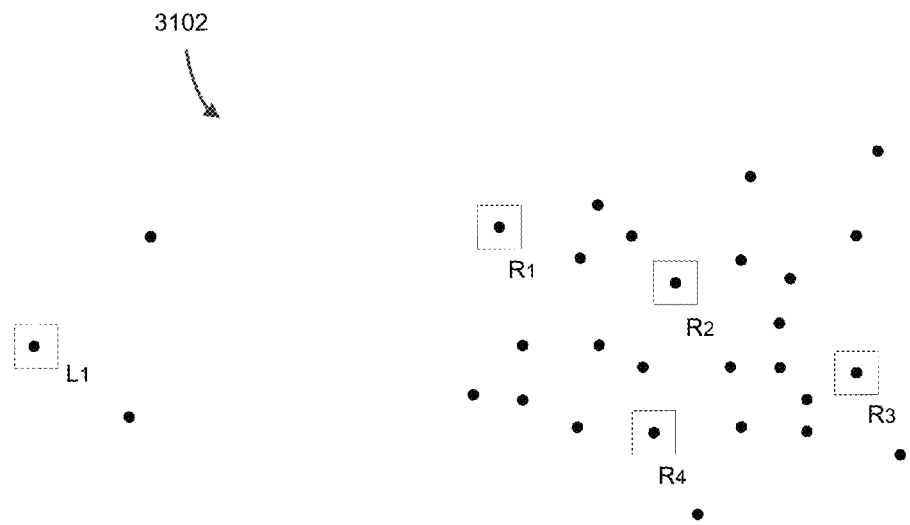
FIG. 33c shows point $P_2$ as new MM landmark point $L_1$.

Thus, with the longest landmark distance, $P_2$ is maximally far away from the random landmarks relative to the other non-landmark points and, at step 3014, landmark assignment module 2912 adds $P_2$ to the set of random landmark points (or seed landmarks) to generate a set of landmark points. Thus, there is an initial set of randomly selected landmark points (R) and max-min landmark points (MM) calculated along the way are subsequently added to R to generate a set of landmarks (L). Accordingly, FIG. 33C shows point $P_2$ as new MM landmark point $L_1$.

Figure 33D:
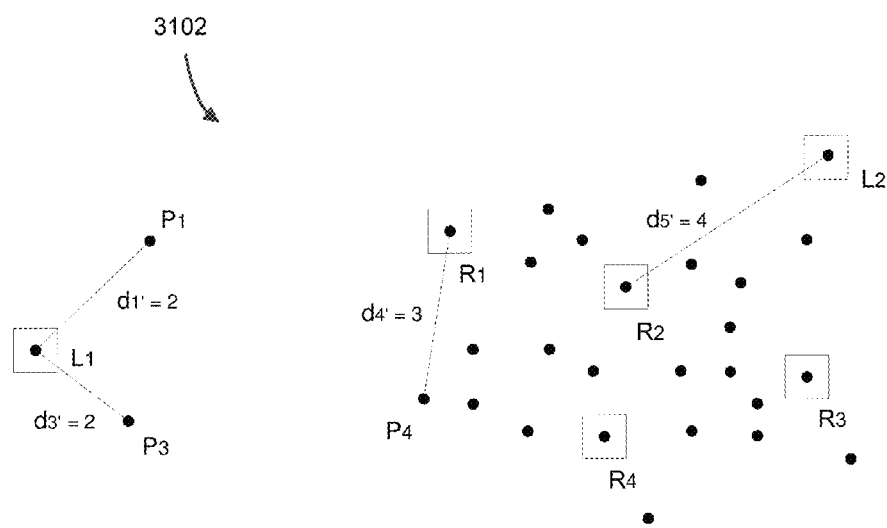
FIG. 33d shows subset with $L_1$ as an existing landmark where the distances between various points have been calculated

In various embodiments, this process starts over to identify and add a second most maximally far away point to the set of landmark points after $L_1$ has been added to the initial set of randomly selected landmark points (R). Thus, steps 3002 to 3014 can be repeated with $L_1$ included into the set of landmark points (L) when determining the landmark distances for each point. Accordingly, FIG. 33D shows subset 3202 with $L_1$ as an existing landmark where the distances between various points have been calculated. In this example, $R_1$ is no longer the closest landmark to points $P_1$ and $P_3$ with the inclusion of $L_1$. For example, $P_1$ is now a distance $d_{1'}=2$ from its nearest landmark $L_1$ and $P_3$, whose nearest landmark is also $L_1$, is now a distance $d_{3'}=2$ from $L_1$. Further shown in FIG. 33D is the distance $d_{4'}=3$ between point $P_4$ and $R_1$ and the distance $d_{5'}=4$ between point $P_4$ and newly added MM landmark point $L_2$ since $d_{5'}$ is larger than $d_{4'}$, $d_{3'}y$, and $d_{1'}$.

In one example, a method for generating a set of landmark points can utilize a process called PROCESS_x_AND_l(X, l), for example, that determines the distances between each point and each landmark point, identifies the closest landmark for each point (dClosest[ ]), and updates an array of dClosest[ ] for each point. Subsequently, a process called FIND_NEXT_L(l) can add a new MM landmark at l to the set of landmarks (L). For example, PROCESS_x_AND_l(x, l) can be implemented as follows:

```
double dist = distance(x, L[l]);
if (dist < dClosest[x]) dClosest[x] = dist;
```

FIND_NEXT_L(l) can be implemented as follows:

```
double closestD = -Double.MAX_VALUE;
for (int x = 0; x < |X|; x++) {
    if (!inL[x] && (dClosest[x] > closestD)) {
        closestD = dClosest[x];
        L[l] = x;
```

Thus, referring back to FIG. 33D, the method for generating a set of landmark points can proceed by first selecting random landmarks $R_1$, $R_2$, $R_3$, and $R_4$ and, thereafter, successively calling PROCESS_x_AND_l(x,l) for each point in metric space 3200 (e.g., each x in X on every l in L). Accordingly, a first portion of a method for generating a set of landmark points can be implemented as follows:

```
for l = 0, l < |R| l++
do
    for x = 0, x < |X|, x++
    do
        PROCESS_x_AND_l(x,l)
```

Once the first portion is completed, the remaining landmark points can be looped over one at a time to find the next MM landmark in a second portion of the method:

```
for l = |R|, l < |L|, l++
do
    FIND_NEXT_L(l)
    for x = 0, x < |X|, x++
    do
        PROCESS_x_AND_l(x,l)
done
```

FIG. 37 is a block diagram of an exemplary digital device 3700. The digital device 3700 comprises a processor 3702, a memory system 3704, a storage system 3706, a communication network interface 3708, an I/O interface 3710, and a display interface 3712 communicatively coupled to a bus 3714. The processor 3702 may be configured to execute executable instructions (e.g., programs). In some embodiments, the processor 3702 comprises circuitry or any processor capable of processing the executable instructions.

The memory system 3704 is any memory configured to store data. Some examples of the memory system 3704 are storage devices, such as RAM or ROM. The memory system 3704 can comprise the ram cache. In various embodiments, data is stored within the memory system 3704. The data within the memory system 3704 may be cleared or ultimately transferred to the storage system 3706.

The storage system 3706 is any storage configured to retrieve and store data. Some examples of the storage system 3706 are flash drives, hard drives, optical drives, and/or magnetic tape. In some embodiments, the digital device 3700 includes a memory system 3704 in the form of RAM and a storage system 3706 in the form of flash data. Both the memory system 3704 and the storage system 3706 comprise computer readable media which may store instructions or programs that are executable by a computer processor including the processor 3702.

The communication network interface (com. network interface) 3708 can be coupled to a data network (e.g., data network 504 or 514) via the link 3716. The communication network interface 3708 may support communication over an Ethernet connection, a serial connection, a parallel connection, or an ATA connection, for example. The communication network interface 3708 may also support wireless communication (e.g., 802.11 a/b/g/n, WiMax). It will be apparent to those skilled in the art that the communication network interface 3708 can support many wired and wireless standards.

The optional input/output (I/O) interface 3710 is any device that receives input from the user and output data. The optional display interface 3712 is any device that may be configured to output graphics and data to a display. In one example, the display interface 3712 is a graphics adapter.

It will be appreciated by those skilled in the art that the hardware elements of the digital device 3700 are not limited to those depicted in FIG. 37. A digital device 3700 may comprise more or less hardware elements than those depicted. Further, hardware elements may share functionality and still be within various embodiments described herein. In one example, encoding and/or decoding may be performed by the processor 3702 and/or a co-processor located on a GPU.

The above-described functions and components can be comprised of instructions that are stored on a storage medium (e.g., a computer readable storage medium). The instructions can be retrieved and executed by a processor. Some examples of instructions are software, program code, and firmware. Some examples of storage medium are memory devices, tape, disks, integrated circuits, and servers. The instructions are operational when executed by the processor (e.g., a data processing device) to direct the processor to operate in accord with embodiments described herein. Those skilled in the art are familiar with instructions, processor(s), and storage medium.

The embodiments described herein has been described above with reference to example embodiments. It will be apparent to those skilled in the art that various modifications may be made and other embodiments can be used without departing from the broader scope of the invention(s). Therefore, these and other variations upon the example embodiments are intended to be covered by the discussion herein.

What is claimed is:

1. A system comprising:
   memory;
   at least one processor;
   an input module configured to control the at least one processor to receive a multidimensional dataset, each data point in the multidimensional dataset having multiple dimensions, each dimension having a value;
   a landmark module configured to control the at least one processor to choose a set of landmarks from the data points, the set of landmarks being a subset of the multidimensional dataset;
   an analysis module configured to control the at least one processor to map each landmark of the set of landmarks into a finite metric space based on the values of the dimensions of each landmark;
   a nearest neighbor module configured to control the at least one processor to compute, for each landmark, a predetermined number of nearest neighbor landmarks in the set of landmarks, distance between every two landmarks being based on dimensions of each of the two landmarks and the finite metric space;
   a graph construction module configured to control the at least one processor to identify at least one pair of landmarks that are nearest neighbors to each other relative to other pairs of landmarks;
   an edge generator module configured to control the at least one processor to add an edge between the at least one pair of landmarks; and
   a non-landmark projection module configured to control the at least one processor to, for each data point in the multidimensional dataset that is not a member of the set of landmarks, determine distances of each of the data points that is not a member of the set of landmarks to the finite metric space to at least one of the landmarks and project each data point that is not a member of the set of landmarks to the finite metric space based on the determined distances, thereby enabling at least one shape to indicate relationships in the data.

2. The system of claim 1 further comprising a filter module configured to control the at least one processor to apply one or more metric functions to the received multidimensional dataset to generate the finite metric space.

3. The system of claim 1 further comprising a visualization module configured to control the at least one processor to generate a visualization of the landmarks, one or more edges, and each data point in the multidimensional dataset that is not a member of the set of landmarks.

4. The system of claim 1 whereby the landmarks, one or more edges, and each data point in the multidimensional dataset that is not a member of the set of landmarks characterize a reference space and the system further comprises a resolution module configured to cluster at least some of the multidimensional dataset based on groupings in the reference space, the groupings being generated by a cover function on the reference space.

5. The system of claim 4 further comprising a visualization module configured to control the at least one processor to generate a visualization depicting nodes, each node associated with a subset of the received multidimensional dataset based on a grouping of the data from the cover function on the reference space, and edges for connecting nodes that share at least some of the same received data.

6. The system of claim 5 wherein the edge generator module is further configured to identify components in the reference space, each component including a subset of landmarks wherein the subset of landmarks of one component do not share any paths with a subset of landmarks of another component.

7. The system of claim 6 wherein the edge generator module is further configured to compute a component strength between a first and second component of the identified components, the strength being based, at least in part, on scoring a number of nearest neighbors of each landmark in the first component, the nearest neighbors residing in the second component, and generate a component pair score using the scoring of the number of nearest neighbors of each landmark in the first component that reside in the second component.

8. The system of claim 7 wherein the edge generator module generates one or more edges between landmarks of components associated with a highest component pair score as compared to other components associated with lower component pair scores.

9. The system of claim 7 wherein the edge generator module is further configured to compute the component strength between the first and second component based, at least in part, on scoring a number of nearest neighbors of each landmark in the second component that reside in the first component, wherein the component pair score is based, at least in part, on the scoring of the number of nearest neighbors of each landmark in the second component that reside in the first component.

10. The system of claim 1 wherein the value is null.

11. The system of claim 1 wherein the landmark module chooses the set of landmarks randomly from the data points.

12. A method comprising:
receiving a multidimensional dataset, each data point in the multidimensional dataset having multiple dimensions, each dimension having a value;
selecting a set of landmarks from the data points, the set of landmarks being a subset of the multidimensional dataset;
mapping each landmark of the set of landmarks into a finite metric space based on the values of the dimensions of each landmark;
computing, for each landmark, a predetermined number of nearest neighbor landmarks in the set of landmarks, distance between every two landmarks being based on dimensions of each of the two landmarks and the finite metric space;
identifying at least one pair of landmarks that are nearest neighbors to each other relative to other pairs of landmarks;
adding an edge between the at least one pair of landmarks; and
for each data point in the multidimensional dataset that is not a member of the set of landmarks:
determining distances of each of the data points that is not a member of the set of landmarks to the finite metric space to at least one of the landmarks, and
projecting each data point that is not a member of the set of landmarks to the finite metric space based on the determined distances, thereby enabling at least one shape to indicate relationships in the data.

13. The method of claim 12 further comprising applying one or more metric functions to the received multidimensional dataset to generate the finite metric space.

14. The method of claim 12 further comprising generating a visualization of the landmarks, one or more edges, and each data point in the multidimensional dataset that is not a member of the set of landmarks.

15. The method of claim 12 whereby the landmarks, one or more edges, and each data point in the multidimensional dataset that is not a member of the set of landmarks characterize a reference space and the method further comprises clustering at least some of the multidimensional dataset based on groupings in the reference space, the groupings being generated by a cover function on the reference space.

16. The method of claim 15 further comprising generating a visualization depicting nodes, each node associated with a subset of the received multidimensional dataset based on a grouping of the data from the cover function on the reference space, and edges for connecting nodes that share at least some of the same received data.

17. The method of claim 16 further comprising identifying components in the reference space, each component including a subset of landmarks wherein the subset of landmarks of one component do not share any paths with a subset of landmarks of another component.

18. The method of claim 17 further comprising computing a component strength between a first and second component of the identified components, the strength being based, at least in part, on scoring a number of nearest neighbors of each landmark in the first component, the nearest neighbors residing in the second component, and generating a component pair score using the scoring of the number of nearest neighbors of each landmark in the first component that reside in the second component.

19. The method of claim 18 further comprising generating one or more edges between landmarks of components associated with a highest component pair score as compared to other components associated with lower component pair scores.

20. The method of claim 18 further comprising computing the component strength between the first and second component based, at least in part, on scoring a number of nearest neighbors of each landmark in the second component that reside in the first component, wherein the component pair score is based, at least in part, on the scoring of the number of nearest neighbors of each landmark in the second component that reside in the first component.

21. A non-transitory computer readable medium, the non-transitory computer readable medium comprising processing instructions executable by a processor to perform a method, the method comprising:
receiving a multidimensional dataset, each data point in the multidimensional dataset having multiple dimensions, each dimension having a value;
selecting a set of landmarks from the data points in a finite metric space, the set of landmarks being a subset of the multidimensional dataset points in the finite metric space;
mapping each landmark of the set of landmarks into a finite metric space based on the values of the dimensions of each landmark;
computing, for each landmark, a predetermined number of nearest neighbor landmarks in the set of landmarks, distance between every two landmarks being based on dimensions of each of the two landmarks and the finite metric space;
identifying at least one pair of landmarks that are nearest neighbors to each other relative to other pairs of landmarks;
adding an edge between the at least one pair of landmarks; and
for each data point in the multidimensional dataset that is not a member of the set of landmarks:
determining distances of each of the data points that is not a member of the set of landmarks to the finite metric space to at least one of the landmarks, and
projecting each data point that is not a member of the set of landmarks to the finite metric space based on the determined distances, thereby enabling at least one shape to indicate relationships in the data.

* * * * *

UNITED STATES PATENT AND TRADEMARK OFFICE
CERTIFICATE OF CORRECTION

| | |
|---|---|
| PATENT NO. | : 10,042,959 B2 |
| APPLICATION NO. | : 14/639954 |
| DATED | : August 7, 2018 |
| INVENTOR(S) | : Harlan Sexton et al. |

Page 1 of 1

It is certified that error appears in the above-identified patent and that said Letters Patent is hereby corrected as shown below:

In the Claims

Claim 21, Column 62, Lines 29-30:
"the data points in a finite metric space, the" should read -- the data points, the --.

Claim 21, Column 62, Lines 31-32:
"multidimensional dataset points in the finite metric space;" should read -- multidimensional dataset; --.

Signed and Sealed this
Twelfth Day of March, 2019

Andrei Iancu
*Director of the United States Patent and Trademark Office*